United States Patent
Vignali et al.

(10) Patent No.: US 9,540,439 B2
(45) Date of Patent: Jan. 10, 2017

(54) THERAPIES BASED ON CONTROL OF REGULATORY T CELL STABILITY AND FUNCTION VIA A NEUROPILIN-1:SEMAPHORIN AXIS

(71) Applicant: ST. JUDE CHILDREN'S RESEARCH HOSPITAL, Memphis, TN (US)

(72) Inventors: Dario A. A. Vignali, Germantown, TN (US); Seng-ryong Woo, Chicago, IL (US); Greg M. Delgoffe, Memphis, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 0 days.

(21) Appl. No.: 14/434,129

(22) PCT Filed: Oct. 8, 2013

(86) PCT No.: PCT/US2013/063934
§ 371 (c)(1),
(2) Date: Apr. 8, 2015

(87) PCT Pub. No.: WO2014/058915
PCT Pub. Date: Apr. 17, 2014

(65) Prior Publication Data
US 2015/0266959 A1 Sep. 24, 2015

Related U.S. Application Data

(60) Provisional application No. 61/711,193, filed on Oct. 8, 2012, provisional application No. 61/712,679, filed on Oct. 11, 2012, provisional application No. 61/784,607, filed on Mar. 14, 2013.

(51) Int. Cl.
| | | |
|---|---|---|
| A61K 39/395 | (2006.01) | |
| C07K 16/28 | (2006.01) | |
| A61K 38/17 | (2006.01) | |
| A61K 31/713 | (2006.01) | |
| C12N 5/0783 | (2010.01) | |
| C12N 15/113 | (2010.01) | |
| A61K 39/00 | (2006.01) | |

(52) U.S. Cl.
CPC ......... *C07K 16/2863* (2013.01); *A61K 31/713* (2013.01); *A61K 38/1709* (2013.01); *C07K 16/2803* (2013.01); *C12N 5/0637* (2013.01); *C12N 15/1138* (2013.01); *A01K 2217/075* (2013.01); *A01K 2227/105* (2013.01); *A01K 2267/0387* (2013.01); *A61K 2039/505* (2013.01); *C07K 2317/73* (2013.01); *C07K 2317/76* (2013.01); *C07K 2319/30* (2013.01); *C07K 2319/32* (2013.01); *C12N 2310/14* (2013.01); *C12N 2501/165* (2013.01)

(58) Field of Classification Search
None
See application file for complete search history.

(56) References Cited

U.S. PATENT DOCUMENTS

| | | |
|---|---|---|
| 7,335,357 B2 | 2/2008 | Klagsbrun et al. |
| 7,696,175 B2 | 4/2010 | Epstein et al. |
| 7,731,959 B2 | 6/2010 | Klagsbrun et al. |
| 7,994,286 B2 | 8/2011 | Watts et al. |
| 8,207,130 B2 | 6/2012 | Epstein et al. |
| 8,211,429 B2 | 7/2012 | Watts et al. |
| 8,268,788 B2 | 9/2012 | Epstein et al. |
| 8,378,080 B2 | 2/2013 | Watts et al. |
| 8,557,248 B2 | 10/2013 | Markham |
| 8,795,660 B2 | 8/2014 | Watts et al. |
| 2004/0052782 A1 | 3/2004 | Kikutani et al. |
| 2004/0248781 A1 | 12/2004 | Kerbel |
| 2006/0024232 A1 | 2/2006 | Schnitzer et al. |
| 2006/0115477 A1 | 6/2006 | Unger et al. |
| 2006/0135459 A1 | 6/2006 | Epstein et al. |
| 2007/0160604 A1 | 7/2007 | Kikutani et al. |
| 2007/0237773 A1 | 10/2007 | Kikutani et al. |
| 2008/0076906 A1 | 3/2008 | Klagsbrun et al. |
| 2008/0213268 A1 | 9/2008 | Watts et al. |
| 2009/0197794 A1 | 8/2009 | Aird et al. |
| 2009/0214533 A1 | 8/2009 | Clynes |

(Continued)

FOREIGN PATENT DOCUMENTS

| | | |
|---|---|---|
| CA | 2 794 123 | 5/2001 |
| EP | 2 497 498 | 9/2012 |
| EP | 2 570 434 | 3/2013 |
| EP | 2 364 166 | 5/2013 |
| WO | WO 03/035100 | 5/2003 |

(Continued)

OTHER PUBLICATIONS

Belkaid et al. "Natural regulatory T cells in infectious disease" Nature Immunology 6(4):353-360 (2005).
Bruder et al. "Neuropilin-1: a surface marker of regulatory T cells" Eur J Immunol 34: 623-630 (2004).
Castro-Rivera, et al. "Semaphorin 3B inhibits the phosphatidylinositol 3-kinase/Akt pathway through neuropilin-1 in lung and breast cancer cells" Cancer Res 68(20): 8295-8303 (2008).

(Continued)

Primary Examiner — Sheela J Huff
(74) Attorney, Agent, or Firm — Fenwick & West LLP

(57) ABSTRACT

The invention is directed to treatment of cancer, infections and various inflammatory and autoimmune conditions by affecting regulatory T cell stability and function via a Neuropilin-1:Semaphorin axis. The present invention satisfies this and other needs by demonstrating that the regulatory T cell (Treg)-restricted neuropilin-1 (Nrp 1) interacts with the cell surface ligand semaphorin-4a (Sema4a) (e.g., on conventional T cells (Tconv), conventional dendritic cells (cDCs), and/or plasmacytoid dendritic cells (pDCs)) to potentiate reg function and enhance their survival at inflammatory sites.

16 Claims, 12 Drawing Sheets

(56) References Cited

U.S. PATENT DOCUMENTS

| | | |
|---|---|---|
| 2010/0008935 A1 | 1/2010 | Borlak et al. |
| 2011/0142839 A1 | 6/2011 | Achen et al. |
| 2011/0256146 A1 | 10/2011 | Watts et al. |
| 2011/0262423 A1 | 10/2011 | Madec et al. |
| 2011/0305689 A1 | 12/2011 | Kim |
| 2012/0058117 A1 | 3/2012 | Unger et al. |
| 2012/0201746 A1 | 8/2012 | Liu et al. |
| 2012/0219614 A1 | 8/2012 | Markham |
| 2012/0245330 A1 | 9/2012 | Watts et al. |
| 2012/0322085 A1 | 12/2012 | Kumanogoh |
| 2013/0041241 A1 | 2/2013 | Felts et al. |
| 2013/0089551 A1 | 4/2013 | Achen et al. |
| 2013/0108652 A1 | 5/2013 | Lee et al. |
| 2013/0115214 A1 | 5/2013 | Watts et al. |
| 2013/0115626 A1 | 5/2013 | Schmidt et al. |
| 2013/0287794 A1 | 10/2013 | Radstake |
| 2014/0004081 A1 | 1/2014 | Cobbold et al. |
| 2014/0010837 A1 | 1/2014 | Markham |
| 2014/0012224 A1 | 1/2014 | Zhang et al. |
| 2014/0099326 A1 | 4/2014 | Schmidt et al. |
| 2014/0349311 A1 | 11/2014 | Kumanogoh |
| 2015/0004178 A1 | 1/2015 | Liu et al. |

FOREIGN PATENT DOCUMENTS

| | | | |
|---|---|---|---|
| WO | WO 2007/056470 A2 | | 5/2007 |
| WO | WO 2007/068487 | | 6/2007 |
| WO | WO 2008/055889 | | 5/2008 |
| WO | WO 2008/055889 A1 | | 5/2008 |
| WO | WO 2008/150868 | | 12/2008 |
| WO | WO 2009/099959 | | 8/2009 |
| WO | WO 2011/143408 | | 11/2011 |
| WO | WO 2011/161217 | | 12/2011 |
| WO | 2012/006503 | * | 1/2012 |
| WO | WO 2012/021558 | | 2/2012 |
| WO | WO 2012/158945 | | 11/2012 |
| WO | WO 2013/007667 | | 1/2013 |
| WO | WO 2013/052772 | | 4/2013 |
| WO | WO 2013/128194 | | 9/2013 |
| WO | WO 2013/170052 | | 11/2013 |
| WO | WO 2014/052792 | | 4/2014 |
| WO | WO 2014/062228 | | 4/2014 |
| WO | WO 2014/064187 | | 5/2014 |

OTHER PUBLICATIONS

Catalano. "The Neuroimmune Semaphorin-3A Reduces Inflammation and Progression of Experimental Autoimmune Arthritis" The Journal of Immunology 185(10):6373-6383 (2010).

Chaturvedi, et al. "Cutting edge: Human regulatory T cells require IL-35 to mediate suppression and infectious tolerance" J Immunol 186:6661-6666 (2011).

Chaudhry et al. "CD4+ regulatory T cells control $T_H17$ responses in a Stat3-dependent manner" Science 326:986-991 (2009).

Chen et al. "Tumor immunogenicity determines the effect of B7 costimulation on T cell-mediated tumor immunity" J. Exp. Med. 179:523-532 (1994).

Collison, et al. "Interleukin-35-mediated induction of a novel regulatory T cell population" Nat Immunol 11(12):1093-1101 (2010).

Collison, et al. "The inhibitory cytokine IL-35 contributes to regulatory T-cell function" Nature 450:566-569 (2007).

Collison, et al. "Regulatory T cell suppression is potentiated by target T cells in a cell contact, IL-35- and IL-10-dependent manner" J Immunol 182(10):6121-6128 (2009).

Crellin, et al. "Altered activation of AKT is required for the suppressive function of human $CD4^+CD25^+$ T regulatory cells" Blood 109(5):2014-2022 (2007).

Delgoffe et al. "Regulatory T cell stability is maintained by a neuropilin-1:semaphorin-4a axis" Nature 501(7466):252-256 (2013).

Evans, et al. "Neuropilin-1 Signaling through $p130^{Cas}$ Tyrosine Phosphorylation is Essential for Growth Factor-Dependent Migration of Glioma and Endothelial Cells" Molecular and Cellular Biology 31(6):1174-1185 (2011).

Finlay, et al. "Phosphoinositide 3-kinase (PI3K) and the nutrient sensing mTOR (mammalian target of rapamycin) pathways control T cell migration" Ann N Y Acad Sci 1183:149-157 (2010).

Fontenot et al. "Foxp3 programs the development and function of $CD4^+CD25^+$regulatory T cells" Nat Immunol 4(4):330-336 (2003).

Francisco et al. "PD-L1 regulates the development, maintenance, and function of induced regulatory T cells" J. Exp. Med. 206(13):3015-3029 (2009).

Fu et al. "A multiple redundant genetic switch locks in the transcriptional signature of regulatory T cells" Nat Immunol. 13(10):972-980 (2012).

Gabhann, et al. "Targeting Neuropilin-1 to Inhibit VEGF Signaling in Cancer: Comparison of Therapeutic Approaches" PLos Computational Biology 2(12-e180):1649-1662, 2006.

Glinka et al. "Neuropilin-1 exerts co-receptor function for TGF-beta-1 on the membrane of cancer cells and enhances responses to both latent and active TGF-beta" Carcinogenesis 32(4):613-621 (2011).

Gorelik, et al. "Abrogation of TGFβ signaling in T cells leads to spontaneous T cell differentiation and autoimmune disease" Immunity 12:171-181 (2000).

Gray et al. "Neuropilin-1 suppresses tumorigenic properties in a human pancreatic adenocarcinoma cell line lacking neuropilin-1 coreceptors" Cancer Res 65(9):3664-3670 (2005).

Gu et al. "Neuropilin-1 conveys semaphorin and VEGF signaling during neural and cardiovascular development" Dev Cell. 5(1):45-57 (2003).

Hansen, et al. "Neuropilin 1 deficiency on $CD4^+Foxp3^+$ regulatory T cells impairs mouse melanoma growth" J. Exp. Med. 209(11):2001-201 (2012).

Haxhinasto, et al. The AKT-mTOR axis regulates de novo differentiation of $CD4^+Foxp3^+$ cells. J Exp Med 205(3):565-574 (2008).

Hill et al. "Foxp3 transcription-factor-dependent and -independent regulation of the regulatory T cell transcriptional signature" Immunity 27:786-800 (2007).

Himmel, et al. "The role of T-regulatory cells and Toll-like receptors in the pathogenesis of human inflammatory bowel disease" Immunology 125:145-153 (2008).

Hori, et al. "Control of regulatory T cell development by the transcription factor Foxp3" Science 299:1057-1061 (2003).

International Search Report and Written Opinion of the International Searching Authority dated Apr. 9, 2014, which issued during prosecution of International Application No. PCT/US2013/063934.

Kerdiles et al. "Foxo transcription factors control regulatory T cell development and function" Immunity 33(6):890-904 (2010).

Kim, et al. "Regulatory T cells prevent catastrophic autoimmunity throughout the lifespan of mice" Nature Immunology 8(2):191-197 (2007).

Kitsukawa et al. "Neuropilin-semaphorin III/D-mediated chemorepulsive signals play a crucial role in peripheral nerve projection in mice" Neuron 19:995-1005 (1997).

Koch et al. "T-bet controls regulatory T cell homeostasis and function during type 1 inflammation" Nat Immunol 10(6):595-602 (2009).

Kolodkin et al. "Neuropilin is a semaphorin III receptor" Cell 90:753-762 (1997).

Lafreniere, et al. "Generation of MC-38 adenocarcinoma tumor-specific tumor infiltrating lymphocytes by murine anti-CD3 antibody and recombinant interleukin-2" Mol Biother 3:26-33 (1991).

Li et al. "Efficient Treg depletion induces T-cell infiltration and rejection of large tumors" Eur. J. Immunol. 40:3325-3335 (2010).

McConnell et al. "Mammalian Krüppel-like factors in health and diseases" Physiol Rev 90:1337-1381 (2010).

Merkenschlager et al. "PI3 kinase signalling blocks Foxp3 expression by sequestering Foxo factors" J. Exp. Med. 207(7):1347-1350 (2010).

Milpied et al. "Neuropilin-1 is not a marker of human $Foxp3^+$ Treg" Eur. J. Immunol. 39:1466-1471 (2009).

(56) References Cited

OTHER PUBLICATIONS

Nishikawa et al. Regulatory T cells in tumor immunity. Int. J. Cancer 127:759-767 (2010).
Nkyimbeng-Takwi, et al. "Biology and function of neuroimmune semaphorins 4A and 4D" Immunol Res. 50(1):10-21 (2011).
Onizuka et al. "Tumor rejection by in vivo administration of anti-CD25 (interleukin-2 receptor α) monoclonal antibody1" Cancer Research 59:3128-3133 (1999).
Ouyang et al. Foxo proteins cooperatively control the differentiation of Foxp3+ regulatory T cells. Nature Immunology 11(7):618-627 (2010).
Pan, et al. "Blocking Neuropilin-1 Function Has an Additive Effect with Anti-VEGF to Inhibit Tumor Growth", Cancer Cell 11:53 (2007).
Parry et al. "CTLA-4 and PD-1 receptors inhibit T-cell activation by distinct mechanisms" Molecular and Cellular Biology 25(21):9543-9553 (2005).
Read et al. "Cytotoxic T lymphocyte-associated antigen 4 plays an essential role in the function of $CD25^+CD4^+$ regulatory cells that control intestinal inflammation" J. Exp. Med. 192(2):295-302 (2000).
Rubtsov et al. "Regulatory T cell-derived interleukin-10 limits inflammation at environmental interfaces" Immunity 28:546-558 (2008).
St. Jude Children's Research Hospital Press Release "Mechanism offers promising new approach for harnessing the immune system to fight cancer" Aug. 4, 2013.
Solomon et al. "Neuropilin-1 attenuates autoreactivity in experimental autoimmune encephalomyelitis" Proc Natl Acad Sci U S A 108(5):2040-2045 (2011).
Stambolic et al. "Negative regulation of PKB/Akt-dependent cell survival by the tumor suppressor PTEN" Cell 95:29-39 (1998).
Toyofuku et al. "Endosomal sorting by Semaphorin 4A in retinal pigment epithelium supports photoreceptor survival" Genes & Development 26:819-829 (2012).
Vignali, et al. "How regulatory T cells work" Nat Rev Immunol. 8(7):523-532 (2008).
Walsh et al. "PTEN inhibits IL-2 receptor-mediated expansion of $CD4^+CD25^+$ Tregs" The Journal of Clinical Investigation 116(9):2521-2531 (2006).
Wang et al. "Tonic ubiquitylation controls T-cell receptor:CD3 complex expression during T-cell development" The EMBO Journal 29(7):1285-1298 (2010).
Wang, et al. "Regulatory T cells and cancer" Current Opinion in Immunology 19:217-223 (2007).
Weiss et al. "Neuropilin 1 is expressed on thymus-derived natural regulatory T cells, but not mucosa-generated induced $Foxp3^+$ T reg cells" J. Exp. Med. 209(10):1723-1742 (2012).
Wilde et al. "Human antitumor $CD8^+$ T cells producing Th1 polycytokines show superior antigen sensitivity and tumor recognition" J Immunol 189:598-605 (2012).
Yadav et al. "Neuropilin-1 distinguishes natural and inducible regulatory T cells among regulatory T cell subsets in vivo" J. Exp. Med. 209(10):1713-1722 (2012).
Zheng et al. "Regulatory T-cell suppressor program co-opts transcription factor IRF4 to control $T_H2$ responses" Nature 458(7236):351-356 (2009).
Zhou et al. "Foxp3 instability leads to the generation of pathogenic memory T cells in vivo" Nat Immunol. 10(9):1000-1007 (2009).
GenBank Accession No. NM_008737 (2014), NCBI Sequence Viewer v2.0, 4 pages, [online] [Retrieved on Jan. 20, 2016] Retrieved from the Internet at <URL: http://www.ncbi.nlm.nih.gov/nuccore/NM_008737>.
GenBank Accession No. NG_030328 (May 4, 2014), NCBI Sequence Viewer v2.0, 25 pages, [online] [Retrieved on Jan. 21, 2016] Retrieved from the Internet at <URL: http://www.ncbi.nlm.nih.gov/nuccore/NG_030328>.
GenBank Accession No. NP_038686 (Feb. 15, 2015), NCBI Sequence Viewer v2.0, 3 pages, [online] [Retrieved on Jan. 20, 2016] Retrieved from the Internet at <URL: http://www.ncbi.nlm.nih.gov/protein/NP_038686>.
Bennett, C.L. et al., "The Immune Dysregulation, Polyendocrinopathy, Enteropathy, X-linked Syndrome (IPEX) is Caused by Mutations of FOXP3," Nature Genetics, Jan. 2001, pp. 20-21, vol. 27.
Bruder, D. et al., "Neuropilin-1: A Surface Marker of Regulatory T Cells," Eur. J. Immunol., 2004, pp. 623-630, vol. 34.
Brunkow, M.E. et al., "Disruption of a New Forkhead/Winged-Helix Protein, Scurfin, Results in the Fatal Lymphoproliferative Disorder of the Scurfy Mouse," Nature Genetics, Jan. 2001, pp. 68-73, vol. 27, No. 1.
Chatila, T.A. et al., "JM2, Encoding a Fork Head-Related Protein, is Mutated in X-Linked Autoimmunity-Allergic Disregulation Syndrome," The Journal of Clinical Investigation, 2000, pp. R75-R81, vol. 106.
Collison, L.W. et al., "In Vitro Treg Suppression Assays," Regulatory T Cells: Methods and Protocols, Methods in Molecular Biology, 2011, Kassiotis, G. et al. (eds.), pp. 21-37, vol. 707.
Delgoffe, G. et al., "Potentiation of Regulatory T Cell Stability and Function via a Neuropilin-1: Semaphorin-4a Axis (P1057)," The Journal of Immunology, May 7, 2013, 1 page, vol. 190.
Delgoffe, G.M. et al., "Regulatory T Cell Stability is Maintained by a Neuropilin-1: Semaphorin-4a Axis," Nature, Sep. 12, 2013, pp. 252-256, vol. 501, No. 7466.
European Extended Search Report, European Application No. 13846146.2. May 9, 2016, 14 pages.
Kim, J.M. et al., "Regulatory T Cells Prevent Catastrophic Autoimmunity Throughout the Lifespan of Mice," Nature Immunology, Feb. 2007, pp. 191-197, vol. 8, No. 2.
Kumanogoh, A. et al., "Class IV Semaphorin Sema4A Enhances T-Cell Activation and Interacts with Tim-2," Nature, Oct. 10, 2002, pp. 529-633, vol. 419.
Milpied, P. et al., "Neuropilin-1 is Not a Marker of Human Foxp3 Treg," European Journal of Immunology, 2009, pp. 1466-1471, vol. 39.
Overacre, A. et al., "Elucidating the Role of Neuropilin-1 in Intra-Tumoral Regulatory T Cell Stability," Journal for ImmunoTherapy of Cancer, Nov. 4, 2015, pp. 1-2, vol. 3, No. 2.
Pan, Q. et al., "Blocking Neuropilin-1 Function Has an Additive Effect with Anti-VEGF to Inhibit Tumor Growth," Cancer Cell, Jan. 2007, pp. 53-67, vol. 11, No. 1.
Parker, M.W. et al., "Structural Basis for Selective Vascular Endothelial Growth Factor-A (VEGF-A) Binding to Neuropilin-1," The Journal of Biological Chemistry, Mar. 30, 2012, pp. 11082-11089, vol. 287, No. 14.
Pellet-Many, C. et al., "Neuropilins: Structure, Function and Role in Disease," Biochem, J., 2008, pp. 211-226, vol. 411.
Powell, J.D. et al., "Regulation of Immune Responses by mTOR," Annu. Rev. Immunol., 2012, pp. 39-68, vol. 30.
Rubtsov, Y.P. et al., "Stability of the Regulatory T Cell Lineage in Vivo," Nature, Sep. 24, 2010, pp. 1667-1671, vol. 329, No. 5999.
Sarris, M. et al., "Neurophilin-1 Expression on Regulatory T Cells Enhances Their Interactions with Dendritic Cells During Antigen Recognition," Immunity, Mar. 2008, pp. 402-413, vol. 28, No. 3.
Satoda, M. et al., "Differential Expression of Two Cell Surface Proteins, Neuropilin and Plexin, in Xenopus Olfactory Axon Subclasses," The Journal of Neuroscience, Jan. 1995, pp. 942-955, vol. 15, No. 1.
Takagi, S. et al., "The A5 Antigen, a Candidate for the Neuronal Recognition Molecule, Has Homologies to Complement Components and Coagulation Factors," Neuron, Aug. 1991, pp. 295-307, vol. 7.
Takamatsu, H. et al. "Diverse Roles for Semaphorin-Plexin Signaling in the Immune System," Trends in Immunology, Mar. 2012, pp. 127-135, vol. 33, No. 3.
Toyofuku, T. et al., "Semaphorin-4A, an Activator for T-Cell-Mediated Immunity, Suppresses Angiogenesis via Plexin-D1," The EMBO Journal, Mar. 2007, pp. 1373-1384, vol. 26, No. 5.

(56) References Cited

OTHER PUBLICATIONS

Wildin, R.S. et al., "X-Linked Neonatal Diabetes Mellitus, Enteropathy and Endocrinopathy Syndrome is the Human Equivalent of Mouse Scurfy," Nature Genetics, Jan. 2001, pp. 18-20, vol. 27, No. 1.

Yadav, M. et al., "Neuropilin-1 Distinguishes Natural and Inducible Regulatory T Cells Among Regulatory T Cell Subsets in Vivo," The Journal of Experimental Medicine, Sep. 10, 2012, pp. 1713-1722, vol. 209, No. 10.

Zhou, X. et al., "Foxp3 Instability Leads to the Generation of Pathogenic Memory T Cells in Vivo," Nature Immunology, Sep. 2009, pp. 1000-1007, vol. 10, No. 9.

* cited by examiner

H

I

D

E

F

G

H

I

US 9,540,439 B2

THERAPIES BASED ON CONTROL OF REGULATORY T CELL STABILITY AND FUNCTION VIA A NEUROPILIN-1:SEMAPHORIN AXIS

CROSS REFERENCE TO RELATED APPLICATIONS

This application is a U.S. National Phase of International Patent Application Number PCT/US2013/063934 and claims the benefit of U.S. Provisional Patent Application No. 61/784,607, filed Mar. 14, 2013, U.S. Provisional Patent Application No. 61/712,679, filed Oct. 11, 2012, and U.S. Provisional Patent Application No. 61/711,193, filed Oct. 8, 2012. The International Application was published on Apr. 17, 2014 as International Publication No. WO 2014/058915 A2 under PCT Article 21(2). The entire contents of all of these applications are hereby incorporated by reference.

STATEMENT AS TO FEDERALLY SPONSORED RESEARCH

The United States Government has certain rights to this invention by virtue of funding reserved from Grant Nos. AI091977, AI039480 and AI098383 from the National Institutes of Health and NCI Comprehensive Cancer Center Support CORE grant CA21765.

FIELD OF THE INVENTION

The present invention is directed to treatment of cancer, infections and various inflammatory and autoimmune conditions by affecting regulatory T cell stability and function via a Neuropilin-1:Semaphorin axis.

BACKGROUND OF THE INVENTION

Regulatory T cells (Tregs) play a crucial role in preventing autoimmunity, limiting immunopathology and maintaining immune homeostasis[1]. However, they also represent a major barrier to effective anti-tumor immunity and sterilizing immunity to chronic viral infections. This highlights the capacity of Tregs to shape and control a wide range of immune responses. Foxp3 is a master transcriptional regulator required for the development, maintenance and stability of Tregs[2,3]. Mice and humans with non-functional Foxp3 lack Tregs and develop a lethal systemic autoimmune condition, referred to as Scurfy in mice and IPEX in humans, highlighting the importance of Tregs in the maintenance of immune homeostasis[2,3]. Furthermore, a transcription factor quintet forms a redundant genetic switch to 'lock-in' the Treg transcriptional signature and enhance their stability[4]. Although some external factors, such as transforming growth factor-β (TGFβ), have been shown to maintain and/or enhance Foxp3 stability and function[5], it is unknown if additional cell-extrinsic pathways or factors exist.

Tissue-resident Tregs are some of the first lymphoid cells to respond to an infection or inflammatory response, thereby limiting immune pathology[6,7]. Some environments, such as tumors and chronic infections, can be highly inflammatory and thus may require additional mechanisms or genetic programs to enhance the stability and function of Tregs in order to limit unintended inflammatory or autoimmune disease. Consequently there is considerable interest in identifying molecular pathways that control Treg stability and function as many immune-mediated diseases are characterized by either exacerbated or limited Treg function, and the adoptive transfer of Tregs for the treatment of a variety of diseases is being actively pursued in the clinic.

Treg stability versus plasticity has been a topic of considerable recent debate. Some studies have defined critical roles for lineage-specific transcription factors, such as T-bet, IRF4 and STAT3, in regulating specific types of T cell responses driven by the same transcription factors[8-10]. In contrast, others have suggested that a demonstrable proportion of Tregs differentiate in inflammatory sites into 'ex-Tregs' and gain effector function[11]. The cell-extrinsic factors and molecular mechanisms by which Tregs alter their transcriptional profile to maintain their stability, regulate immunity in inflammatory sites and control these alternate cell fates remain obscure.

Neuropilin-1 (Nrp1; see, e.g., GenBank Accession Nos. NM_008737 (mouse) and NG_030328 (human) as well as various isoforms) is a membrane-bound coreceptor to a tyrosine kinase receptor for both vascular endothelial growth factor (VEGF) and class III semaphorin Sema3a. Nrp1 plays versatile roles in axon guidance, angiogenesis, cell survival, migration, and invasion[15]. Nrp1 induces axon growth cone collapse, preventing infiltration into privileged tissues and its genetic deletion in mice results in embryonic lethality[16]. Nrp1 has been also shown to interact platelet derived growth factor beta (PDGFβ) and transforming growth factor beta (TGFβ)[17,18]. Nrp1 has been shown to be highly expressed in Tregs[19-21]. Although a role for Nrp1 in T cells has been implicated[22], no role for Nrp1 in Tregs has been identified and it has been suggested that Nrp1 is not expressed on human Tregs[25].

SUMMARY OF THE INVENTION

As specified in the Background Section, there is a great need in the art to identify the molecular pathways that control Treg stability and function and use this understanding to develop novel therapeutics for the treatment of cancer, infections and various inflammatory and autoimmune conditions. The present invention satisfies this and other needs by demonstrating that the regulatory T cell (Treg)-restricted neuropilin-1 (Nrp1) interacts with the cell surface ligand semaphorin-4a (Sema4a) (e.g., on conventional T cells (Tconv), conventional dendritic cells (cDCs), and/or plasmacytoid dendritic cells (pDCs)) to potentiate Treg function and enhance their survival at inflammatory sites.

In one embodiment, the invention provides a method of inhibiting a function or decreasing stability of a regulatory T cell (Treg) comprising exposing said Treg to an inhibitor of neuropilin-1 (Nrp1):semaphorin axis in said Treg. In one embodiment, the inhibitor of Nrp1:semaphorin axis inhibits interaction between a transmembrane semaphorin (e.g., a class IV semaphorin such as, e.g., Sema4a) on a cell expressing such transmembrane semaphorin (e.g., a conventional T cell (Tconv), a conventional dendritic cell (cDC), or a plasmacytoid dendritic cell (pDC)) and Nrp1 on the Treg. In one embodiment, the inhibitor of Nrp1:semaphorin axis does not affect Nrp1-VEGF interaction in said Treg. In one embodiment, said Treg is in a subject (e.g., human) and the inhibitor of Nrp1:semaphorin axis is administered to the subject. In one embodiment, the subject has a cancer (e.g., melanoma or glioblastoma). In another embodiment, the subject has an infection in which Tregs are blocking sterilizing immunity (e.g., a chronic infection). In one embodiment, the inhibitor of Nrp1:semaphorin axis is an antibody (e.g., an antibody which does not affect Nrp1-VEGF interaction in said Treg). In another embodiment, the inhibitor of Nrp1:semaphorin axis is a semaphorin molecule (e.g., a soluble version of a transmembrane semaphorin protein [e.g., a class IV semaphorin such as, e.g., Sema4a] or a fragment or a derivative or an analog thereof [including various fusion molecules such as, e.g., a Sema4a extracellular domain fused to Fc region of IgG1 at the C-terminus], wherein said soluble version of a transmembrane semaphorin protein, fragment, derivative or analog is capable of binding with high affinity and specificity to Nrp1 on Treg without potentiating Nrp1:semaphorin axis in said Treg). In yet another embodiment, the inhibitor of Nrp1:semaphorin axis is a soluble extracellular domain of Nrp1 protein or a fragment or a derivative or an analog thereof, wherein said soluble extracellular domain of Nrp1 protein, fragment, derivative or analog is capable of binding with high affinity and specificity to a transmembrane semaphorin (e.g., a class IV semaphorin such as, e.g., Sema4a) thereby preventing said transmembrane semaphorin from potentiating Nrp1:semaphorin axis in said Treg. In a further embodiment, the inhibitor of Nrp1:semaphorin axis inhibits expression of Nrp1 protein in the Treg (e.g., is an siRNA or an antisense oligonucleotide). In a further embodiment, the inhibitor of Nrp1:semaphorin axis prevents Nrp1 from engaging with its downstream signaling pathway(s). In one specific embodiment, the inhibitor of Nrp1:semaphorin axis inhibits a signaling pathway between the cytoplasmic domain of Nrp1 protein comprising the C-terminal amino acid sequence SEA (C-terminal PDZ domain-binding motif) and PTEN protein; such inhibitor can be, e.g., a peptide or a small molecule or a fragment of Nrp1 protein comprising all or part of its cytoplasmic domain comprising the C-terminal amino acid sequence SEA or a derivative or an analog thereof. In one specific embodiment, the inhibitor of Nrp1:semaphorin axis is a small molecule.

In a separate embodiment, the invention provides a method of enhancing a function or increasing stability of a regulatory T cell (Treg) comprising exposing said Treg to an agonist of neuropilin-1 (Nrp1):semaphorin axis in said Treg. In one embodiment, the agonist of Nrp1:semaphorin axis enhances interaction between a transmembrane semaphorin (e.g., a class IV semaphorin such as, e.g., Sema4a) on a cell expressing such transmembrane semaphorin (e.g., a conventional T cell (Tconv), a conventional dendritic cell (cDC), or a plasmacytoid dendritic cell (pDC)) and Nrp1 on the Treg. In one embodiment, the agonist of Nrp1:semaphorin axis is administered to the Treg in vitro. In one embodiment, the Treg is extracted from a subject (e.g., human), is expanded ex vivo in the presence of the agonist of Nrp1-semaphorin interaction and then (i) is reintroduced back into the subject or (ii) is administered to a different subject. In one embodiment, the subject receiving expanded Tregs has an autoimmune or an inflammatory disease. In another embodiment, the Treg is in a subject (e.g., human) and the agonist of Nrp1:semaphorin axis is administered to the subject. In one embodiment, the subject has an autoimmune or an inflammatory disease. In one embodiment, the agonist of Nrp1:semaphorin axis is a semaphorin molecule (e.g., a multimerized semaphorin molecule and/or a semaphorin molecule immobilized on a surface or a bead). In one embodiment, the semaphorin molecule is a class IV semaphorin (e.g., Sema4a) or a fragment or a derivative or an analog thereof. In one embodiment, the agonist of Nrp1:semaphorin axis is an antibody. In another embodiment, the agonist of Nrp1:semaphorin axis is a small molecule. In yet another embodiment, the agonist of Nrp1:semaphorin axis enhances Nrp1 expression in the Treg. In a further embodiment, the agonist of Nrp1:semaphorin axis enhances Nrp1 engagement with its downstream signaling pathway(s).

In a separate embodiment, the invention provides a method of treating a disease in a subject (e.g., human) in need thereof, the method comprising inhibiting neuropilin-1 (Nrp1):semaphorin axis in regulatory T cells (Tregs) of the subject. In one embodiment, the method comprises inhibiting interaction between a transmembrane semaphorin (e.g., a class IV semaphorin such as, e.g., Sema4a) on cells expressing such transmembrane semaphorin (e.g., conventional T cells (Tconv), conventional dendritic cells (cDCs), and/or plasmacytoid dendritic cells (pDCs)) and Nrp1 on the Tregs of the subject. In one embodiment, the disease is a cancer (e.g., melanoma or glioblastoma). In another embodiment, the disease is an infection in which Tregs are blocking sterilizing immunity (e.g., a chronic infection). In one embodiment, the method comprises administering to the subject a therapeutically effective amount of an inhibitor of neuropilin-1 (Nrp1):semaphorin axis in Tregs of the subject. In one embodiment, the inhibitor of Nrp1:semaphorin axis is an antibody (e.g., an antibody which does not affect Nrp1-VEGF interaction in the Tregs of the subject). In another embodiment, the inhibitor of Nrp1:semaphorin axis is a semaphorin molecule (e.g., a soluble version of a transmembrane semaphorin protein [e.g., a class IV semaphorin such as, e.g., Sema4a] or a fragment or a derivative or an analog thereof [including various fusion molecules such as, e.g., a Sema4a extracellular domain fused to Fc region of IgG1 at the C-terminus], wherein said soluble version of a transmembrane semaphorin protein, fragment, derivative or analog is capable of binding with high affinity and specificity to Nrp1 on Tregs without potentiating Nrp1:semaphorin axis in said Tregs). In yet another embodiment, the inhibitor of Nrp1:semaphorin axis is a soluble extracellular domain of Nrp1 protein or a fragment or a derivative or an analog thereof, wherein said soluble extracellular domain of Nrp1 protein, fragment, derivative or analog is capable of binding with high affinity and specificity to a transmembrane semaphorin (e.g., a class IV semaphorin such as, e.g., Sema4a) thereby preventing said transmembrane semaphorin from potentiating Nrp1:semaphorin axis in the Tregs of the subject. In a further embodiment, the inhibitor of Nrp1:semaphorin axis inhibits expression of Nrp1 protein in the Tregs of the subject (e.g., is an siRNA or an antisense oligonucleotide). In a further embodiment, the inhibitor of Nrp1:semaphorin axis prevents Nrp1 from engaging with its downstream signaling pathway(s). In one specific embodiment, the inhibitor of Nrp1:semaphorin axis inhibits a signaling pathway between the cytoplasmic domain of Nrp1 protein comprising the C-terminal amino acid sequence SEA (C-terminal PDZ domain-binding motif) and PTEN protein; such inhibitor can be, e.g., a peptide or a small molecule or a fragment of Nrp1 protein comprising all or part of its cytoplasmic domain comprising the C-terminal amino acid sequence SEA or a derivative or an analog thereof. In one specific embodiment, the inhibitor of Nrp1:semaphorin axis is a small molecule. In another embodiment, the method further comprises administering to the subject an additional immunomodulatory treatment (e.g., a therapeutic vaccine, a checkpoint inhibitor or an activator). In yet another embodiment, the method further comprises administering to the subject a chemotherapy or a radiation therapy (for treatment of cancers) or administering an antibiotic (for treatment of infections).

In a separate embodiment, the invention provides a method of treating a disease in a subject (e.g., human) in need thereof, the method comprising activating neuropilin-1 (Nrp1):semaphorin axis in regulatory T cells (Tregs) of the subject. In one embodiment, the method comprises enhancing interaction between a transmembrane semaphorin (e.g., a class IV semaphorin such as, e.g., Sema4a) on cells expressing such transmembrane semaphorin (e.g., conventional T cells (Tconv), conventional dendritic cells (cDCs), and/or plasmacytoid dendritic cells (pDCs)) and Nrp1 on the Tregs of the subject. In one embodiment, the subject has an autoimmune or inflammatory disease. In one embodiment, the method comprises administering to the subject a therapeutically effective amount of an agonist of neuropilin-1 (Nrp1):semaphorin axis in Tregs of the subject. In one embodiment, the agonist of Nrp1:semaphorin axis is a semaphorin molecule (e.g., a multimerized semaphorin molecule and/or a semaphorin molecule immobilized on a surface or a bead). In one embodiment, the semaphorin molecule is a class IV semaphorin (e.g., Sema4a) or a fragment or a derivative or an analog thereof. In one embodiment, the agonist of Nrp1:semaphorin axis is an antibody. In another embodiment, the agonist of Nrp1:semaphorin axis is a small molecule. In yet another embodiment, the agonist of Nrp1:semaphorin axis enhances Nrp1 expression in the Tregs of the subject. In a further embodiment, the agonist of Nrp1:semaphorin axis enhances Nrp1 engagement with its downstream signaling pathway(s). In another embodiment, the method further comprises administering to the subject another therapy which enhances Tregs or blocks inflammation.

In a separate embodiment, the invention provides a method for enhancing the efficacy of a vaccine (e.g., a vaccine for treating or preventing cancer or infection) in a subject (e.g., human), the method comprising administering to the subject an effective amount of an inhibitor of neuropilin-1 (Nrp1):semaphorin axis in Tregs of the subject. In one embodiment, the inhibitor of Nrp1:semaphorin axis is an antibody (e.g., an antibody which does not affect Nrp1-VEGF interaction in the Tregs of the subject). In another embodiment, the inhibitor of Nrp1:semaphorin axis is a semaphorin molecule (e.g., a soluble version of a transmembrane semaphorin protein [e.g., a class IV semaphorin such as, e.g., Sema4a] or a fragment or a derivative or an analog thereof [including various fusion molecules such as, e.g., a Sema4a extracellular domain fused to Fc region of IgG1 at the C-terminus], wherein said soluble version of a transmembrane semaphorin protein, fragment, derivative or analog is capable of binding with high affinity and specificity to Nrp1 on Tregs without potentiating Nrp1:semaphorin axis in said Tregs). In yet another embodiment, the inhibitor of Nrp1:semaphorin axis is a soluble extracellular domain of Nrp1 protein or a fragment or a derivative or an analog thereof, wherein said soluble extracellular domain of Nrp1 protein, fragment, derivative or analog is capable of binding with high affinity and specificity to a transmembrane semaphorin (e.g., a class IV semaphorin such as, e.g., Sema4a) thereby preventing said transmembrane semaphorin from potentiating Nrp1:semaphorin axis in the Tregs of the subject. In a further embodiment, the inhibitor of Nrp1:semaphorin axis inhibits expression of Nrp1 protein in the Tregs of the subject (e.g., is an siRNA or an antisense oligonucleotide). In a further embodiment, the inhibitor of Nrp1:semaphorin axis prevents Nrp1 from engaging with its downstream signaling pathway(s). In one specific embodiment, the inhibitor of Nrp1:semaphorin axis inhibits a signaling pathway between the cytoplasmic domain of Nrp1 protein comprising the C-terminal amino acid sequence SEA (C-terminal PDZ domain-binding motif) and PTEN protein; such inhibitor can be, e.g., a peptide or a small molecule or a fragment of Nrp1 protein comprising all or part of its cytoplasmic domain comprising the C-terminal amino acid sequence SEA or a derivative or an analog thereof. In one specific embodiment, the inhibitor of Nrp1:semaphorin axis is a small molecule. In one embodiment of the method, the inhibitor of Nrp1:semaphorin axis is administered to the subject before the vaccine is administered to the subject. In another embodiment of the method, the inhibitor of Nrp1:semaphorin axis is administered to the subject together with the vaccine.

In a separate embodiment, the invention provides an isolated antibody which inhibits neuropilin-1 (Nrp1):semaphorin (e.g., a class IV semaphorin such as, e.g., Sema4a) interaction on a regulatory T cell (Treg).

These and other aspects of the present invention will be apparent to those of ordinary skill in the art in the following description, claims and drawings.

DETAILED DESCRIPTION OF THE INVENTION

Figure 1:
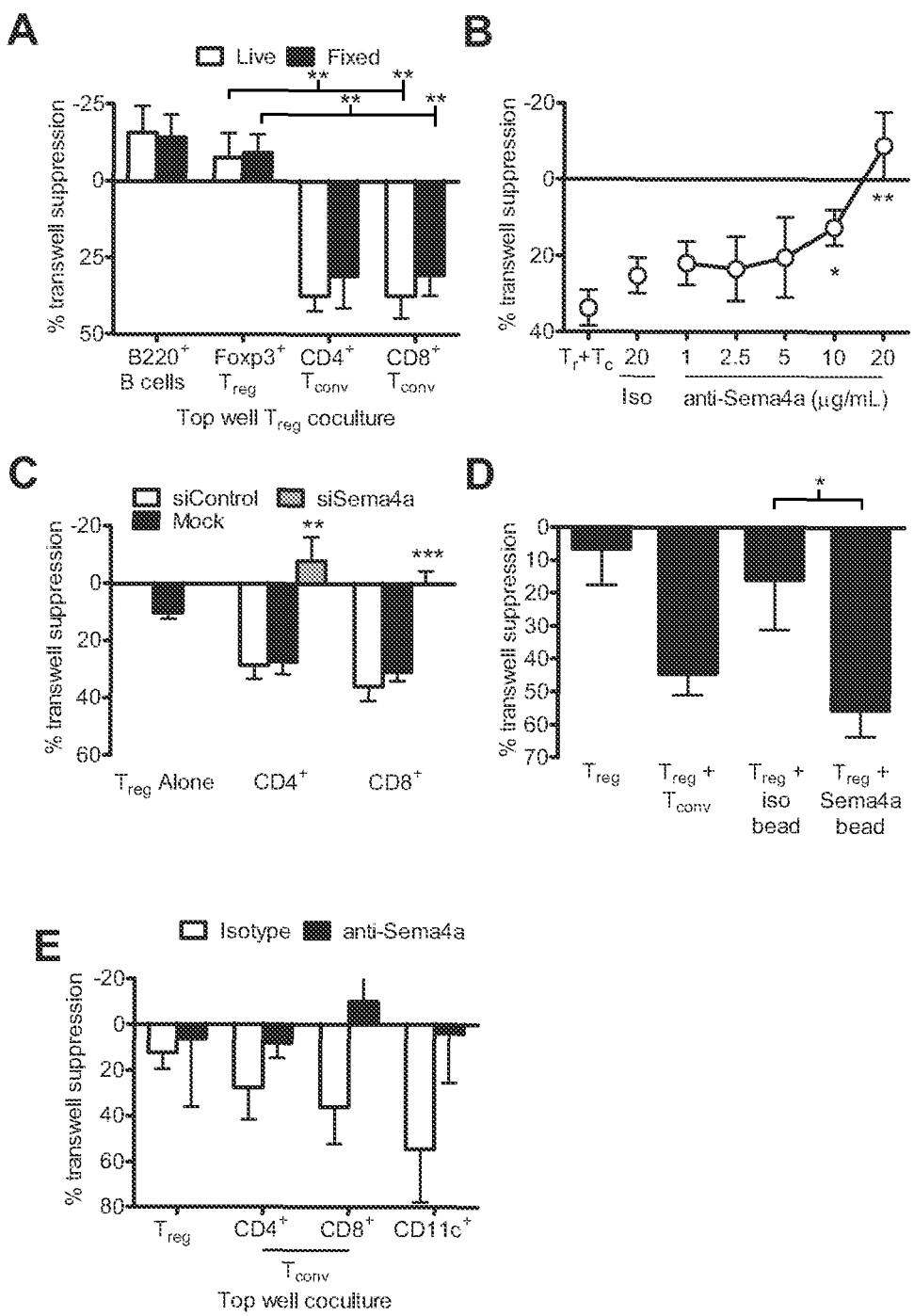
FIGS. 1A-E demonstrate that Semaphorin 4a potentiates regulatory T cell function. A, Transwell suppression assay of Tconv stimulated with anti-CD3/anti-CD28 coated beads in the bottom well when regulatory T cells (Tregs) are stimulated in the top well in the presence of the indicated cell types. For some conditions, the coculture cell population was fixed prior to Treg stimulation. B, Transwell suppression assay in which neutralizing antibodies to semaphorin-4a (Sema4a) were included. C, CD4$^+$ or CD8$^+$ Tconv were mock transfected or transfected with scrambled siRNA or Sema4a siRNA and then boosting potential assessed in a Transwell suppression assay. D, Transwell suppression assay in which Treg monocultures were stimulated with beads coated with mouse IgG1 or Sema4a-Ig in the top well. E, Transwell suppression assay in which fixed dendritic cells sorted direct ex vivo as well as neutralizing antibodies to semaphorin-4a (Sema4a) were included. Results represent the mean of five [A, D] or three [B, C, E] experiments. *, p<0.05, , p<0.01, *, p<0.001 by unpaired t-test.

The present invention is based on an unexpected observation that that the immune cell surface ligand semaphorin-4a (Sema4a) on conventional murine and human T cells and the regulatory T cell (Treg)-restricted receptor neuropilin-1 (Nrp1) interact to potentiate Treg function and enhance their survival. Mice with a Treg-restricted deletion of Nrp1 exhibit limited tumor-induced tolerance, and thus substantial resistance to certain tumors, yet do not develop any autoimmune or inflammatory manifestations. As specified in the Examples section, below, Nrp1 blockade also has therapeutic efficacy against pre-existing tumors. Nrp1 is recruited to the immunological synapse (IS) and represses Akt activity via phosphatase and tensin homolog (PTEN), which facilitate Foxo nuclear translocation. This induces a transcriptional program that promotes Treg stability, survival and function while repressing the induction of lineage-specific transcription factors. Thus, Nrp1 ligation enforces Treg stability and function in highly inflammatory sites but is dispensable for the maintenance of immune homeostasis, highlighting inhibition of Nrp1-semaphorin axis as a immunotherapeutic target in cancer and infections, while its potentiation as a target in treating autoimmunity and inflammation. Blocking Nrp1-semaphorin interaction could limit Treg function in tumors but not elsewhere enhancing anti-tumor activity without adverse side effects. This can provide effective cancer treatment and prevention both at very early stages of tumor development and during late stages, including metastasis. Similar approaches could be efficacious in any other diseases where Tregs pose a barrier (e.g., chronic infections in which Tregs are blocking sterilizing immunity, such as, e.g., HCV, HBV, HIV infections, etc.) and may enhance vaccination. On the other hand, enhancing Nrp1-semaphorin interaction would increase Treg function in diseases where they fail (e.g., autoimmune and inflammatory conditions). In connection with enhancing Nrp1-semaphorin interaction to increase Treg function, also disclosed herein is adoptive therapy approach, wherein patient's Tregs are expanded ex vivo in the presence of an agonist of Nrp 1-semaphorin interaction and then are reintroduced back into the same patient or are administered to a different patient.

Definitions

The terms "Treg" or "regulatory T cell" refer to $CD4^+$ T cells that suppresses $CD4^+CD25^-$ and $CD8^+$ T cell proliferation and/or effector function, or that otherwise downmodulate an immune response. Notably, Treg may downregulate immune responses mediated by Natural Killer cells, Natural Killer T cells as well as other immune cells. In a preferred embodiment, Tregs of the invention are $Foxp3^+$.

The terms "regulatory T cell function" or "a function of Treg" are used interchangeably to refer to any biological function of a Treg that results in a reduction in $CD4^+CD25^-$ or $CD8^+$ T cell proliferation or a reduction in an effector T cell-mediated immune response. Treg function can be measured via techniques established in the art. Non-limiting examples of useful in vitro assays for measuring Treg function include Transwell suppression assay described in the Examples section, below, as well as, more generally, in vitro assays in which the target conventional T cells (Tconv) and Tregs purified from human peripheral blood or umbilical cord blood (or murine spleens or lymph nodes) are optionally activated by anti-$CD3^+$ anti-CD28 coated beads (or antigen-presenting cells (APCs) such as, e.g., irradiated splenocytes or purified dendritic cells (DCs) or irradiated PBMCs) followed by in vitro detection of conventional T cell proliferation (e.g., by measuring incorporation of radioactive nucleotides (such as, e.g., $[^3H]$-thymidine) or fluorescent nucleotides, or by Cayman Chemical MTT Cell Proliferation Assay Kit, or by monitoring the dilution of a green fluorochrome ester CFSE or Seminaphtharhodafluor (SNARF-1) dye by flow cytometry). Other common assays measure T cell cytokine responses. Useful in vivo assays of Treg function include assays in animal models of diseases in which Tregs play an important role, including, e.g., (1) homeostasis model (using naïve homeostatically expanding $CD4^+$ T cells as target cells that are primarily suppressed by Tregs), (2) inflammatory bowel disease (IBD) recovery model (using Th1 T cells (Th17) as target cells that are primarily suppressed by Tregs), (3) experimental autoimmune encephalomyelitis (EAE) model (using Th17 and Th1 T cells as target cells that are primarily suppressed by Tregs), (4) B16 melanoma model (suppression of antitumor immunity) (using $CD8^+$ T cells as target cells that are primarily suppressed by Tregs), (5) suppression of colon inflammation in adoptive transfer colitis where naïve $CD4^+CD45RB^{hi}$ Tconv cells are transferred into $Rag1^{-/-}$ mice, and (6) $Foxp3^-$ rescue model (using lymphocytes as target cells that are primarily suppressed by Tregs). According to one protocol, all of the models require mice for donor T cell populations as well as $Rag1^{-/-}$ or $Foxp3^-$ mice for recipients. For more details on various useful assays see, e.g., Collison and Vignali, In Vitro Treg Suppression Assays, Chapter 2 in *Regulatory T Cells: Methods and Protocols*, Methods in Molecular Biology, Kassiotis and Liston eds., Springer, 2011, 707:21-37; Workman et al., In Vivo Treg Suppression Assays, Chapter 9 in *Regulatory T Cells: Methods and Protocols*, Methods in Molecular Biology, Kassiotis and Liston eds., Springer, 2011, 119-156; Takahashi et al., Int. Immunol., 1998, 10:1969-1980; Thornton et al., J. Exp. Med., 1998, 188:287-296; Collison et al., J. Immunol., 2009, 182:6121-6128; Thornton and Shevach, J. Exp. Med., 1998, 188:287-296; Asseman et al., J. Exp. Med., 1999, 190:995-1004; Dieckmann et al., J. Exp. Med., 2001, 193:1303-1310; Belkaid, Nature Reviews, 2007, 7:875-888; Tang and Bluestone, Nature Immunology, 2008, 9:239-244; Bettini and Vignali, Curr. Opin. Immunol., 2009, 21:612-618; Dannull et al., J Clin Invest, 2005, 115(12):3623-33; Tsaknaridis, et al., J Neurosci Res., 2003, 74:296-308.

The term "neuropilin-1 (Nrp1):semaphorin axis of a regulatory T cell (Treg)" as used herein refers to the signaling pathway initiated by semaphorin (e.g., a semaphorin expressed by a cell such as, e.g., a conventional T cell, or a recombinant semaphorin), ligation of Nrp1, and the subsequent downstream signaling.

The terms "antagonist" or "inhibitor" in connection with Nrp1:semaphorin axis of Tregs are used interchangeably herein and refer to any agent that can (i) interfere with the productive ligation and/or crosslinking of semaphorin:Nrp1 or (ii) inhibit the immediate downstream signaling consequences of Nrp1 in Tregs. The inhibition of Nrp1:semaphorin interaction on Tregs can be assessed by any of the methods known in the art, including Transwell suppression assay described in the Examples section, below.

The terms "agonist" or "potentiator" in connection with Nrp1:semaphorin axis of Tregs are used interchangeably herein and refer to any agent that can (i) enhance interaction of Nrp1:semaphorin, or (ii) mimic semaphorin stimulation and Nrp1 signaling artificially to the Treg, or (iii) activate immediate downstream signaling consequences of Nrp1 in Tregs. The enhancement of Nrp1:semaphorin interaction on Tregs can be assessed by any of the methods known in the art, including the Transwell suppression assay described in the Examples section, below.

For therapeutic applications, the agonists and antagonists of the present invention can be used as pharmaceutical compositions and can be optionally combined with other agonists/antagonists of the invention or other therapeutic molecules.

The term "a semaphorin molecule" as used herein in connection with agonists of the Nrp1:semaphorin axis of Tregs encompasses transmembrane semaphorin molecules involved in interaction with Nrp1 on Tregs (e.g., Sema4a), various surface- and bead-immobilized versions of such molecules, as well as multimers, derivatives, mutants, analogs, and fragments of such molecules which can be used to enhance a function or increase stability of Tregs. Non-limiting examples of such agonist semaphorin molecules are discussed in more detail below and include, for example, IgM-derived semaphorin fusion proteins that assemble multimeric complexes incapable of fixing complement, that crosslink Nrp1 solubly.

The term "a semaphorin molecule" as used herein in connection with inhibitors of the Nrp1:semaphorin axis of Tregs encompasses soluble versions of transmembrane semaphorin molecules involved in interaction with Nrp1 on Tregs (e.g., Sema4a) as well as various derivatives, mutants, analogs, and fragments of such molecules (including various fusion molecules), which can be used to inhibit a function or decrease stability of Tregs. Non-limiting examples of such inhibitory semaphorin molecules are discussed in more detail below and include, for example, various soluble fragments of Sema4a and derivatives or analogs thereof which outcompete endogenous Sema4a for Nrp1 binding. In one specific embodiment, the inhibitory semaphorin molecule is Sema4a-Ig fusion protein, which is a fusion (at the C-terminus) between Sema4a extracellular domain (Met1-His683 fragment of GenBank Accession No. NP_038686) and the Fc region of human or murine IgG1.

The term "analog" refers to a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

The term "inflammation" as used herein refers to any excessive or undesirable immune response. The term "inflammatory disease" as used herein refers to any pathology associated with an excessive or an undesirable immune response.

The term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

In the context of the present invention insofar as it relates to any of the disease conditions recited herein, the terms "treat", "treatment", and the like mean to relieve or alleviate at least one symptom associated with such condition, or to slow or reverse the progression of such condition. Within the meaning of the present invention, the term "treat" also denotes to arrest, delay the onset (i.e., the period prior to clinical manifestation of a disease) and/or reduce the risk of developing or worsening a disease. E.g., in connection with cancer the term "treat" may mean eliminate or reduce a patient's tumor burden, or prevent, delay or inhibit metastasis, etc.

As used herein the term "therapeutically effective" applied to dose or amount refers to that quantity of a compound or pharmaceutical composition that is sufficient to result in a desired activity upon administration to a subject in need thereof. Within the context of the present invention, the term "therapeutically effective" refers to that quantity of a compound (e.g., an antagonist or agonist of Nrp1:semaphorin axis of Tregs) or pharmaceutical composition containing such compound that is sufficient to delay the manifestation, arrest the progression, relieve or alleviate at least one symptom of a disorder treated by the methods of the present invention. Note that when a combination of active ingredients is administered the effective amount of the combination may or may not include amounts of each ingredient that would have been effective if administered individually.

The phrase "pharmaceutically acceptable", as used in connection with compositions of the invention, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

As used herein, the term "subject" refers to any mammal. In a preferred embodiment, the subject is human.

As used in this specification and the appended claims, the singular forms "a," "an," and "the" include plural references unless the context clearly dictates otherwise.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A practical Approach*, Volumes I and II (D. N. Glover ed. 1985); *Oligonucleotide Synthesis* (MJ. Gait ed. 1984); *Nucleic Acid Hybridization* (B. D. Hames & S. J. Higgins eds. (1985>>; *Transcription and Translation* (B. D. Hames & S. J. Higgins, eds. (1984>>; *Animal Cell Culture* (R. I. Freshney, ed. (1986>>; *Immobilized Cells and Enzymes* (IRL Press, (1986>>; B. Perbal, *A practical Guide To Molecular Cloning* (1984); F. M. Ausubel et al. (eds.), *Current Protocols in Molecular Biology*, John Wiley & Sons, Inc. (1994); among others.

Methods of the Invention

In one embodiment, the invention provides a method of inhibiting a function or decreasing stability of a Treg) comprising exposing said Treg to an inhibitor of Nrp1:semaphorin axis in said Treg. In one embodiment, such inhibitor of Nrp1:semaphorin axis inhibits interaction between a transmembrane semaphorin (e.g., class IV semaphorin such as, e.g., Sema4a) on conventional T cell and Nrp1 on the Treg. In one specific embodiment, the inhibitor of Nrp1:semaphorin axis does not affect Nrp1-VEGF interaction in said Treg. The inhibitor of Nrp1:semaphorin axis can be administered directly to a subject (e.g., human), e.g., a subject suffering from a cancer or an infection. In a related embodiment, the invention provides a method of treating a disease (e.g., a cancer or an infection) in a subject (e.g., human) in need thereof, the method comprising selectively inhibiting Nrp1:semaphorin axis in Tregs of the subject.

In one embodiment, the inhibitors of Nrp1:semaphorin axis useful in the methods of the invention are antibodies. In one specific embodiment, such antibodies do not affect Nrp1-VEGF interaction or Nrp1-semaphorin class III interaction in Tregs.

In another embodiment, the inhibitors of Nrp1:semaphorin axis useful in the methods of the invention are semaphorin molecules (e.g., a soluble version of sema4a protein or a fragment or a derivative or an analog thereof).

In yet another embodiment, the inhibitors of Nrp1:semaphorin axis useful in the methods of the invention are small molecules.

The present invention also encompasses inhibitors of Nrp1:semaphorin axis in Tregs which inhibit Nrp1 expression in Tregs, or locally (e.g., in tumors) inhibit transmembrane semaphorin expression on cells expressing such transmembrane semaphorin (e.g., conventional T cells (Tconv), conventional dendritic cells (cDCs), and/or plasmacytoid dendritic cells (pDCs)), or prevent Nrp1 from engaging with its downstream signaling pathway(s).

In a separate embodiment, the invention provides a method of enhancing a function or increasing stability of a Treg comprising exposing said Treg to an agonist of Nrp1: semaphorin axis in said Treg. In one embodiment, such agonist of Nrp1:semaphorin axis enhances interaction between a transmembrane semaphorin (e.g., class IV semaphorin such as, e.g., Sema4a) on conventional T cell and Nrp1 on the Treg. In one embodiment, the agonist of Nrp1:semaphorin axis is administered to the Treg in vitro (e.g., the Treg can be extracted from a subject (e.g., human suffering from an autoimmune or inflammatory disease), expanded ex vivo in the presence of an agonist of Nrp1-semaphorin interaction and then reintroduced back into the same subject or administered to a different subject). In another embodiment, the agonist of Nrp1:semaphorin axis can be administered directly to a subject (e.g., human), e.g., a subject suffering from an autoimmune or inflammatory disease. In a related embodiment, the invention provides a method of treating a disease (e.g., an autoimmune or inflammatory disease) in a subject (e.g., human) in need thereof, the method comprising selectively activating Nrp1:semaphorin axis in Tregs of the subject.

In one embodiment, the agonists of Nrp1:semaphorin axis useful in the methods of the invention are semaphorin molecules (e.g., Sema4a protein or a fragment or a derivative or an analog thereof). Such semaphorin molecules can be, e.g., multimerized and/or immobilized on a surface or a bead.

In another embodiment, the agonists of Nrp1:semaphorin axis useful in the methods of the invention are antibodies.

In yet another embodiment, the agonists of Nrp1:semaphorin axis useful in the methods of the invention are small molecules.

The present invention also encompasses the agonists of Nrp1:semaphorin axis in Tregs which enhance Nrp1 expression in Tregs, or locally (e.g., in pancreatic islets for diabetes) enhance semaphorin expression on cells expressing transmembrane semaphorin (e.g., conventional T cells (Tconv), conventional dendritic cells (cDCs), and/or plasmacytoid dendritic cells (pDCs)), or enhance Nrp1 engagement with its downstream signaling pathway(s).

Additional inhibitors and agonists of Nrp1:semaphorin axis on Treg can be identified using various screening methods known in the art (e.g., using immobilized target molecules or fragments thereof).

The inhibitors or agonists of the invention can be used in therapeutic methods described above or can be administered to a nonhuman mammal for the purposes of obtaining preclinical data. Exemplary nonhuman mammals to be treated include nonhuman primates, dogs, cats, rodents and other mammals in which preclinical studies are performed. Such mammals may be established animal models for a disease to be treated or may be used to study toxicity of the inhibitor or agonist of interest. In each of these embodiments, dose escalation studies may be performed in the mammal.

Non-limiting examples of cancers treatable by the methods of the invention include, for example, carcinomas, lymphomas, sarcomas, blastomas, and leukemias. Non-limiting specific examples, include, for example, breast cancer, pancreatic cancer, liver cancer, lung cancer, prostate cancer, colon cancer, renal cancer, bladder cancer, head and neck carcinoma, thyroid carcinoma, soft tissue sarcoma, ovarian cancer, primary or metastatic melanoma, squamous cell carcinoma, basal cell carcinoma, brain cancer, angiosarcoma, hemangiosarcoma, bone sarcoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, testicular cancer, uterine cancer, cervical cancer, gastrointestinal cancer, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, Waldenstroom's macroglobulinemia, papillary adenocarcinomas, cystadenocarcinoma, bronchogenic carcinoma, bile duct carcinoma, choriocarcinoma, seminoma, embryonal carcinoma, Wilms' tumor, lung carcinoma, epithelial carcinoma, cervical cancer, testicular tumor, glioma, glioblastoma, astrocytoma, medulloblastoma, craniopharyngioma, ependymoma, pinealoma, hemangioblastoma, acoustic neuroma, oligodendroglioma, meningioma, retinoblastoma, leukemia, neuroblastoma, small cell lung carcinoma, bladder carcinoma, lymphoma, multiple myeloma, medullary carcinoma, B cell lymphoma, T cell lymphoma, myeloma, leukemia, chronic myeloid leukemia, acute myeloid leukemia, chronic lymphocytic leukemia, acute lymphocytic leukemia, hematopoietic neoplasias, thymoma, sarcoma, non-Hodgkins lymphoma, Hodgkins lymphoma, uterine cancer, renal cell carcinoma, hepatoma, etc.

The infections treatable by the methods of the present invention include, without limitation, any infections (in particular, chronic infections) in which Tregs are blocking sterilizing immunity and which can be caused by, for example, a bacterium, parasite, virus, fungus, or protozoa.

Non-limiting examples of the inflammatory and autoimmune diseases treatable by the methods of the present invention include, e.g., inflammatory bowel disease (IBD), ulcerative colitis, Crohn's disease, arthritis, diabetes, multiple sclerosis, such as, e.g., inflammatory bowel disease (IBD), ulcerative colitis, Crohn's disease, arthritis, diabetes mellitus type 1, multiple sclerosis, Graves' disease, lupus erythematosus, ankylosing spondylitis, psoriasis, Behcet's disease, autistic enterocolitis, Guillain-Barre Syndrome, myasthenia gravis, pemphigus vulgaris, acute disseminated encephalomyelitis (ADEM), transverse myelitis autoimmune cardiomyopathy, Celiac disease, dermatomyositis, Wegener's granulomatosis, allergy, asthma, contact dermatitis (including any reaction to a man-made chemical), atherosclerosis (or any other inflammatory condition affecting the heart or vascular system), etc.

It is contemplated that when used to treat various diseases, the inhibitors or agonists of the invention can be combined with other therapeutic agents suitable for the same or similar diseases. Also, two or more inhibitors or agonists of the invention may be also co-administered to generate additive or synergistic effects. When co-administered with a second therapeutic agent, the inhibitors or agonists of the invention and the second therapeutic agent may be simultaneously or sequentially (in any order). Suitable therapeutically effective dosages for each agent may be lowered due to the additive action or synergy.

The Nrp1:semaphorin axis agonists of the invention can be combined with other therapies that enhance Tregs (e.g., non-mitogenic anti-CD3), in vivo Treg transfer, or therapies that block inflammation (e.g., via blockage of ILL INFα/β, IL6, TNF, IL13, IL23, etc.).

In one embodiment, the inhibitors of Nrp1:semaphorin axis on Tregs disclosed herein are useful to enhance the efficacy of vaccines directed to infections or tumors. Similarly to vaccines against infections which contain inactivated cells of the infectious agent or a single or several antigens, tumor vaccines typically contain inactivated tumor cells or tumor antigens that stimulate a patient's immune system. The immune system responds to this stimulation by generating immunoresponsive cells that target the infection or neoplasia. As Tregs act to suppress such immune response, the inhibition of their function and stability by the methods of the invention can lead to enhanced immune response to vaccines.

The Treg inhibitors of the invention can be administered to a subject either simultaneously with or before (e.g., 1-14 days before) a reagent that acts to elicit an immune response (e.g., to treat cancer or an infection) is administered to the subject.

The inhibitory compounds of the invention can be also administered in combination with an anti-tumor antibody or an antibody directed at a pathogenic antigen.

The inhibitory treatments of the invention can be combined with other immunomodulatory treatments such as, e.g., therapeutic vaccines (including but not limited to GVAX, DC-based vaccines, etc.), checkpoint inhibitors (including but not limited to agents that block CTLA4, PD1, LAG3, TIM3, etc.) or activators (including but not limited to agents that enhance 41 BB, OX40, etc.). The inhibitory treatments of the invention can be also combined with other treatments that possess the ability to inhibit Treg function or stability. Some non-limiting examples of such additional Treg inhibitors include ONTAK, HuMax-Tac, Zenapax, and MDX-010.

Therapeutic methods of the invention can be combined with additional immunotherapies and therapies. For example, when used for treating cancer, inhibitors of the invention can be used in combination with conventional cancer therapies, such as, e.g., surgery, radiotherapy, chemotherapy or combinations thereof, depending on type of the tumor, patient condition, other health issues, and a variety of factors. In certain aspects, other therapeutic agents useful for combination cancer therapy with the inhibitors of the invention include anti-angiogenic agents. Many anti-angiogenic agents have been identified and are known in the art, including, e.g., TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alpha, soluble KDR and FLT-1 receptors, placental proliferin-related protein, as well as those listed by Carmeliet and Jain (2000). In one embodiment, the inhibitors of the invention can be used in combination with a VEGF antagonist or a VEGF receptor antagonist such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases and any combinations thereof (e.g., anti-hVEGF antibody A4.6.1, bevacizumab or ranibizumab).

Non-limiting examples of chemotherapeutic compounds which can be used in combination treatments of the present invention include, for example, aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramnustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethyhnelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

For treatment of infections, combined therapy of the invention can encompass co-administering Treg inhibitors of the invention with an antibiotic, an anti-fungal drug, an anti-viral drug, an anti-parasitic drug, an anti-protozoal drug, or a combination thereof.

Non-limiting examples of useful antibiotics include lincosamides (clindomycin); chloramphenicols; tetracyclines (such as Tetracycline, Chlortetracycline, Demeclocycline, Methacycline, Doxycycline, Minocycline); aminoglycosides (such as Gentamicin, Tobramycin, Netilmicin, Amikacin, Kanamycin, Streptomycin, Neomycin); beta-lactams (such as penicillins, cephalosporins, Imipenem, Aztreonam); vancomycins; bacitracins; macrolides (erythromycins), amphotericins; sulfonamides (such as Sulfanilamide, Sulfamethoxazole, Sulfacetamide, Sulfadiazine, Sulfisoxazole, Sulfacytine, Sulfadoxine, Mafenide, p-Aminobenzoic Acid, Trimethoprim-Sulfamethoxazole); Methenamin; Nitrofurantoin; Phenazopyridine; trimethoprim; rifampicins; metronidazoles; cefazolins; Lincomycin; Spectinomycin; mupirocins; quinolones (such as Nalidixic Acid, Cinoxacin, Norfloxacin, Ciprofloxacin, Pefloxacin, Ofloxacin, Enoxacin, Fleroxacin, Levofloxacin); novobiocins; polymixins; gramicidins; and antipseudomonals (such as Carbenicillin, Carbenicillin Indanyl, Ticarcillin, Azlocillin, Mezlocillin, Piperacillin) or any salts or variants thereof. See also Physician's Desk Reference, 59.sup.th edition, (2005), Thomson P D R, Montvale N.J.; Gennaro et al., Eds. Remington's The Science and Practice of Pharmacy, 20.sup.th edition, (2000), Lippincott Williams and Wilkins, Baltimore Md.; Braunwald et al., Eds. Harrison's Principles of Internal Medicine, 15.sup.th edition, (2001), McGraw Hill, NY; Berkow et al., Eds. The Merck Manual of Diagnosis and Therapy, (1992), Merck Research Laboratories, Rahway N.J. Such antibiotics can be obtained commercially, e.g., from Daiichi Sankyo, Inc. (Parsipanny, N.J.), Merck (Whitehouse Station, N.J.), Pfizer (New York, N.Y.), Glaxo Smith Kline (Research Triangle Park, N.C.), Johnson & Johnson (New Brunswick, N.J.), AstraZeneca (Wilmington, Del.), Novartis (East Hanover, N.J.), and Sanofi-Aventis (Bridgewater, N.J.). The antibiotic used will depend on the type of bacterial infection.

Non-limiting examples of useful anti-fungal agents include imidazoles (such as griseofulvin, miconazole, terbinafine, fluconazole, ketoconazole, voriconazole, and itraconizole); polyenes (such as amphotericin B and nystatin); Flucytosines; and candicidin or any salts or variants thereof. See also Physician's Desk Reference, 59.sup.th edition, (2005), Thomson P D R, Montvale N.J.; Gennaro et al., Eds. Remington's The Science and Practice of Pharmacy 20.sup.th edition, (2000), Lippincott Williams and Wilkins, Baltimore Md.; Braunwald et al., Eds. Harrison's Principles of Internal Medicine, 15.sup.th edition, (2001), McGraw Hill, NY; Berkow et al., Eds. The Merck Manual of Diagnosis and Therapy, (1992), Merck Research Laboratories, Rahway N.J.

Non-limiting examples of useful anti-viral drugs include interferon alpha, beta or gamma, didanosine, lamivudine, zanamavir, lopanivir, nelfinavir, efavirenz, indinavir, valacyclovir, zidovudine, amantadine, rimantidine, ribavirin, ganciclovir, foscarnet, and acyclovir or any salts or variants thereof. See also Physician's Desk Reference, 59.sup.th edition, (2005), Thomson P D R, Montvale N.J.; Gennaro et al., Eds. Remington's The Science and Practice of Pharmacy 20.sup.th edition, (2000), Lippincott Williams and Wilkins, Baltimore Md.; Braunwald et al., Eds. Harrison's Principles of Internal Medicine, 15.sup.th edition, (2001), McGraw Hill, NY; Berkow et al., Eds. The Merck Manual of Diagnosis and Therapy, (1992), Merck Research Laboratories, Rahway N.J.

Non-limiting examples of useful anti-parasitic agents include chloroquine, mefloquine, quinine, primaquine, atovaquone, sulfasoxine, and pyrimethamine or any salts or variants thereof. See also Physician's Desk Reference, 59.sup.th edition, (2005), Thomson P D R, Montvale N.J.; Gennaro et al., Eds. Remington's The Science and Practice of Pharmacy 20.sup.th edition, (2000), Lippincott Williams and Wilkins, Baltimore Md.; Braunwald et al., Eds. Harrison's Principles of Internal Medicine, 15.sup.th edition, (2001), McGraw Hill, NY; Berkow et al., Eds. The Merck Manual of Diagnosis and Therapy, (1992), Merck Research Laboratories, Rahway N.J.

Non-limiting examples of useful anti-protozoal drugs include metronidazole, diloxanide, iodoquinol, trimethoprim, sufamethoxazole, pentamidine, clindamycin, primaquine, pyrimethamine, and sulfadiazine or any salts or variants thereof. See also Physician's Desk Reference, 59.sup.th edition, (2005), Thomson P D R, Montvale N.J.; Gennaro et al., Eds. Remington's The Science and Practice of Pharmacy 20.sup.th edition, (2000), Lippincott Williams and Wilkins, Baltimore Md.; Braunwald et al., Eds. Harrison's Principles of Internal Medicine, 15.sup.th edition, (2001), McGraw Hill, NY; Berkow et al., Eds. The Merck Manual of Diagnosis and Therapy, (1992), Merck Research Laboratories, Rahway N.J.

Antibody Inhibitors and Agonists of the Invention

In conjunction with the above methods, the invention provides isolated antibodies which inhibit or augment Nrp1: semaphorin interaction on Tregs. In one embodiment, the semaphorin is class IV semaphorin (e.g., Sema4a). In one embodiment, the antibodies do not affect Nrp1-VEGF interaction or Nrp1-semaphorin class III interaction in Tregs.

The invention encompasses both anti-Nrp1 and anti-semaphorin antibodies which interfere with Nrp-1:semaphorin interaction on Tregs. Examples of useful antibodies include, for example, (i) antibodies which specifically target "sema" and "PSI" domains of semaphorin molecules, an evolutionarily conserved region on all semaphorin molecules (see, e.g., Takamatsu and Kumanogoh, Trends Immunol., 2012, 33(3):127-135) as well as (ii) antibodies which target the semaphorin-binding domain on Nrp1 (rather than the VEGF-binding domain) (see, e.g., Parker et al., J. Biol. Chem., 2012, 287(14):11082-11089).

For both inhibitory and potentiating antibodies, the invention also provides bispecific antibodies which, in addition to Nrp1, also recognize a Treg-specific protein and therefore target the antibody specifically to Tregs. For example, such bispecific antibodies, in addition to Nrp1, can target a surface protein of the Tregs, which include, for example, CD25, CD4, CD28, CD38, CD62L (selectin), OX-40 ligand (OX-404 CTLA4, CCR4, CCR8, FOXP3, LAG3, CD103, glucocorticoid-induced TNF receptor (GITR), galectin-1, TNFR2, or TGFβR1.

The antibodies for use in accordance with the present invention may be monoclonal or polyclonal as appropriate. The antibody fragments can be also used and include, for example, Fab, Fab', F(ab)$_2$ or Fv fragments. The antibody may be a single chain antibody. Other suitable modifications and/or agents will be apparent to those skilled in the art. Chimeric and humanized antibodies are also within the scope of the invention. It is expected that chimeric and humanized antibodies would be less immunogenic in a human subject than the corresponding non-chimeric antibody. A variety of approaches for making chimeric antibodies, comprising for example a non-human variable region and a human constant region, have been described. See, for example, Morrison et al., Proc. Natl. Acad. Sci. U.S.A. 81, 6851 (1985); Takeda, et al., Nature 314, 452 (1985), Cabilly et al., U.S. Pat. No. 4,816,567; Boss et al., U.S. Pat. No. 4,816,397; Tanaguchi et al., European Patent Publication EP 171496; European Patent Publication 0173494, United Kingdom Patent GB 2177096B. Additionally, a chimeric antibody can be further "humanized" such that parts of the variable regions, especially the conserved framework regions of the antigen-binding domain, are of human origin and only the hypervariable regions are of non-human origin. Such altered immunoglobulin molecules may be made by any of several techniques known in the art, (e.g., Teng et al., Proc. Natl. Acad. Sci. U.S.A., 80, 7308-7312 (1983); Kozbor et al., Immunology Today, 4, 7279 (1983); Olsson et al., Meth. Enzymol., 92, 3-16 (1982)), and are preferably made according to the teachings of PCT Publication WO92/06193 or EP 0239400. Humanized antibodies can be commercially produced by, for example, Scotgen Limited, 2 Holly Road, Twickenham, Middlesex, Great Britain.

In certain embodiments, anti-idiotypic antibodies are also provided. Anti-idiotypic antibodies recognize antigenic determinants associated with the antigen-binding site of another antibody. Anti-idiotypic antibodies can be prepared against a second antibody by immunizing an animal of the same species, and preferably of the same strain, as the animal used to produce the second antibody. See, e.g., U.S. Pat. No. 4,699,880. In one embodiment, antibodies are raised against Nrp1 or semaphorin or a portion thereof, and these antibodies are used in turn to produce an anti-idiotypic antibody.

The present invention provides antibodies for both intracellular and extracellular targeting. Intracellular targeting can be accomplished through the use of intracellularly expressed antibodies referred to as intrabodies.

To screen for additional antibodies which bind to a particular epitope on the antigen of interest (e.g., Nrp1 or Sema4a), a routine cross-blocking assay such as that described in Antibodies, A Laboratory Manual, Cold Spring Harbor Laboratory, Ed Harlow and David Lane (1988), can be performed. Alternatively, epitope mapping, e.g. as described in Champe et al. (1995) J. Biol. Chem. 270:1388-1394, can be performed to determine whether the antibody binds an epitope of interest.

Additional antibodies useful in the present invention can be also generated and selected using phage display approach as described, e.g. in U.S. Patent Appl. Publ. No. 2008/0213268.

Antibodies of the invention can be further modified to generate antibody mutants with improved physical, chemical and or biological properties over the parent antibody. Where the assay used is a biological activity assay, the antibody mutant preferably has a biological activity in the assay of choice (e.g., measuring a function or stability of a Treg via Transwell suppression assay and upregulation of Bcl2 or Helios) which is at least about 10 fold better, preferably at least about 20 fold better, more preferably at least about 50 fold better, and sometimes at least about 100 fold or 200 fold better, than the biological activity of the parent antibody in that assay.

To generate the antibody mutant, one or more amino acid alterations (e.g. substitutions) can be introduced in one or more of the hypervariable regions of the parent antibody. Alternatively, or in addition, one or more alterations (e.g., substitutions) of framework region residues may be introduced in the parent antibody where these result in an improvement in the binding affinity of the antibody mutant for the antigen from the second mammalian species. Examples of framework region residues to modify include those which non-covalently bind antigen directly (Amit et al. (1986) Science 233:747-753); interact with/effect the conformation of a CDR (Chothia et al. (1987) J. Mol. Biol. 196:901-917); and/or participate in the $V_L$-$V_H$ interface (EP 239400B1). In certain embodiments, modification of one or more of such framework region residues results in an enhancement of the binding affinity of the antibody for the antigen from the second mammalian species. For example, from about one to about five framework residues may be altered in this embodiment of the invention. Sometimes, this may be sufficient to yield an antibody mutant suitable for use in preclinical trials, even where none of the hypervariable region residues have been altered. Normally, however, the antibody mutant will comprise additional hypervariable region alteration(s). The hypervariable region residues which are altered may be changed randomly, especially where the starting binding affinity of the parent antibody is such that such randomly produced antibody mutants can be readily screened.

One useful procedure for generating such antibody mutants is called "alanine scanning mutagenesis" (Cunningham and Wells (1989) Science 244:1081-1085). Here, one or more of the hypervariable region residue(s) are replaced by alanine or polyalanine residue(s) to affect the interaction of the amino acids with the antigen from the second mammalian species. Those hypervariable region residue(s) demonstrating functional sensitivity to the substitutions then are refined by introducing further or other mutations at or for the sites of substitution. The ala-mutants produced this way are screened for their biological activity as described herein.

Antibodies of the invention can be prepared by standard means.

For preparation of immunizing antigen, and polyclonal and monoclonal antibody production see, e.g., Kohler et al., Nature 256:495-497 (1975) and Eur. J. Immunol. 6:511-519 (1976); Milstein et al., Nature 266:550-552 (1977); Koprowski et al., U.S. Pat. No. 4,172,124; Harlow and Lane, "Antibodies: A Laboratory Manual," (Cold Spring Harbor Laboratory: Cold Spring Harbor, N.Y., 1988); and "Current Protocols In Molecular Biology," (Ausubel et al., Eds.; John Wiley & Sons: New York, N.Y., 1991); Kozbar et al., Immunology Today 4:72 (1983)), Cole et al., "Monoclonal Antibodies and Cancer Therapy" (Alan R. Liss, Inc. pp. 77-96 (1985)). Cells which produce antibodies with the desired specificity can be selected by a suitable assay (e.g., ELISA).

The antibodies of the invention can be also produced recombinantly, using well-known techniques. See, e.g., Cabilly et al., U.S. Pat. No. 4,816,567; Winter, U.S. Pat. No. 5,225,539. A nucleic acid encoding a desired antigen can be isolated or synthethized using conventional procedures and inserted into a replicable vector for further cloning or for expression.

When using recombinant techniques, the antibody can be produced intracellularly, in the periplasmic space, or directly secreted into the medium and further isolated and purified using known techniques such as, for example, hydroxylapatite chromatography, gel electrophoresis, dialysis, and affinity chromatography. Protein A affinity chromatography can be used to purify antibodies that are based on human γ1, γ2, or γ4 heavy chains (Lindmark et al. (1983) J. Immunol. Meth. 62:1-13). Protein G affinity chromatography can be used for mouse isotypes and for human γ3 (Guss et al. (1986) EMBO J. 5:15671575).

The various portions of chimeric, humanized, primatized (CDR-grafted) antibodies, or CDR-grafted single chain antibodies, comprising portions derived from different species, antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816, 397; Boss et al., European Patent No. 0,120,694 B1; Neuberger et al., WO 86/01533; Neuberger et al., European Patent No. 0,194,276 B1; Winter, U.S. Pat. No. 5,225,539; and Winter, European Patent No. 0,239,400 B1. See also, Newman et al., *BioTechnology* 10:1455-1460 (1992), regarding primatized antibody and Ladner et al., U.S. Pat. No. 4,946,778 and Bird et al., *Science* 242:423-426 (1988)), regarding single chain antibodies. Nucleic acid (e.g., DNA) sequences coding for humanized variable regions can be constructed using PCR mutagenesis methods to alter DNA sequences encoding a human or humanized chain, such as a DNA template from a previously humanized variable region (see, e.g., Kamman et al., Nucl. Acids Res., 17:5404 (1989)); Sato et al., Cancer Research 53:851-856 (1993); Daugherty et al., Nucleic Acids Res. 19(9):2471-2476 (1991); and Lewis and Crowe, Gene 101:297-302 (1991)). Using these or other suitable methods, variants can also be readily produced. In one embodiment, cloned variable regions can be mutagenized, and sequences encoding variants with the desired specificity can be selected (e.g., from a phage library; see, e.g., Krebber et al., U.S. Pat. No. 5,514,548; and Hoogenboom et al., WO 93/06213).

In addition, functional fragments of antibodies, including fragments of chimeric, humanized, primatized, or single chain antibodies can also be produced. Functional fragments of the subject antibodies retain at least one binding function and/or modulation function of the full-length antibody from which they are derived. Useful antibody fragments include, but are not limited to, Fv, Fab, Fab' and F(ab')$_2$ fragments. Such fragments can be produced by enzymatic cleavage or by recombinant techniques. For instance, papain or pepsin cleavage can generate Fab or F(ab')$_2$ fragments, respectively. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH1 domain and hinge region of the heavy chain.

Other suitable methods of producing or isolating antibodies of the requisite specificity can be used, including, for example, methods which select recombinant antibody from a library, or which rely upon immunization of transgenic animals (e.g., mice) capable of producing a full repertoire of human antibodies. See, e.g., Jakobovits et al., *Proc. Natl. Acad. Sci. USA* 90:2551-2555 (1993); Jakobovits et al., *Nature* 362:255-258 (1993); Lonberg et al., U.S. Pat. No. 5,545,806; Surani et al., U.S. Pat. No. 5,545,807; Cabilly et al., U.S. Pat. No. 4,816,567; Cabilly et al., European Patent No. 0,125,023 B1; Queen et al., European Patent No. 0,451,216 B1; Boss et al., U.S. Pat. No. 4,816,397; Boss et al., European Patent No. 0,120,694 E1; Neuberger et al., WO 86/01533; Neuberger et al., European Patent No. 0,194,276 B1; Winter, U.S. Pat. No. 5,225,539; Winter, European Patent No. 0,239,400 B1; and Padlan et al., European Patent Application No. 0,519,596 A1. See, also, Ladner et al., U.S. Pat. No. 4,946,778; Huston, U.S. Pat. No. 5,476,786; and Bird et al., *Science* 242: 423-426 (1988).

In certain embodiments, the antibodies or antigen binding fragments of the antibodies can be labeled or unlabeled and used for diagnostic purposes. Typically, diagnostic assays entail detecting the formation of a complex resulting from the binding of an antibody to its target. The antibodies can be directly labeled with, for example, a radionuclide, a fluorophore, an enzyme, an enzyme substrate, an enzyme cofactor, an enzyme inhibitor, and a ligand (e.g., biotin or a hapten). Numerous appropriate immunoassays are known to the skilled artisan (see, e.g., U.S. Pat. Nos. 3,817,827; 3,850,752; 3,901,654; and 4,098,876).

Pharmaceutical compositions comprising the antibodies of the invention can be prepared by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The pharmaceutical compositions comprising the antibodies of the invention may also contain one or more additional active compounds as necessary for the particular indication being treated, preferably those with complementary activities that do not adversely affect each other. Various active agents can be present in combination in amounts that are effective for the purpose intended. Non-limiting examples of possible additional active compounds include, e.g., IL2 and TGFβ as well as various agents listed in the discussion of combination treatments, above.

The active ingredients may be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be also prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinyl-alcohol)), polylactides (U.S. Pat. No. 3,773,919), copolymers of L-glutamic acid and .gamma. ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

For the treatment of a disease, the appropriate dosage of antibody of the invention will depend on the type of disease to be treated, the severity and course of the disease, whether the antibody is administered for preventive or therapeutic purposes, previous therapy, the patient's clinical history and response to the antibody, and the discretion of the attending physician. The antibody can be administered to the patient at one time or over a series of treatments. The progress of the therapy of the invention can be easily monitored by conventional techniques and assays.

The administration of antibodies of the invention can be performed by any suitable route, including systemic administration as well as administration directly to the site of the disease (e.g., to primary tumor or chronic infection site).

Protein/Peptide Inhibitors and Agonists of the Invention

As specified above, the inhibitors of Nrp1:semaphorin axis useful in the methods of the invention include various semaphorin molecules, such as, for example, soluble versions of transmembrane semaphorin proteins (e.g., Sema4a) as well as various inhibitory fragments, derivatives, and analogs thereof. Also included within the present invention are soluble extracellular domains of Nrp1 which can function as competitive inhibitors of Nrp1:semaphorin axis as well as various inhibitory fragments, derivatives, and analogs thereof. In one specific embodiment, the inhibitory semaphorin molecule is Sema4a-Ig fusion protein, which is a fusion (at the C-terminus) between Sema4a extracellular domain (Met1-His683 fragment of GenBank Accession No. NP_038686) and the Fc region of human or murine IgG1. In one specific embodiment, the inhibitory semaphorin molecule is a fragment of Nrp1 protein (or a derivative or an analog thereof) comprising all or part of Nrp1 cytoplasmic domain comprising the C-terminal amino acid sequence SEA, which molecule inhibits a signaling pathway between the cytoplasmic domain of Nrp1 protein and PTEN protein.

As further discussed above, the agonists of Nrp1:semaphorin axis useful in the methods of the invention also include various semaphorin molecules, including full-length semaphorin proteins (e.g., Sema4a protein) as well as agonist fragments, derivatives, and analogs thereof. Such agonist semaphorin molecules can be, e.g., multimerized (e.g., using IgM fusion proteins) and/or immobilized on a surface or a bead.

Soluble inhibitory versions of transmembrane semaphorin proteins include, for example, their complete extracellular domains (e.g., the entire extracellular domain of Sema4a) or Nrp1-binding portions of such extracellular domains (e.g., fused to an Fc domain) which are capable of binding with high affinity and specificity to Nrp1 without potentiating Nrp1:semaphorin axis on Tregs. In some embodiments, such inhibitory versions of transmembrane semaphorin proteins do not affect Nrp1-VEGF interaction in Tregs. Soluble inhibitory versions of extracellular domains of Nrp1 include, for example, the entire extracellular domain of Nrp1 or Sema4a-binding portions of such extracellular domain (e.g., fused to an Fc domain) which are capable of binding with high affinity and specificity to Sema4a without potentiating Nrp1:semaphorin axis on Tregs. The effectiveness of semaphorin molecules or fragments or soluble inhibitory versions of extracellular domains of Nrp1 to inhibit Nrp1:semaphorin axis on Tregs can be tested using assays known in the art and those outlined in the Examples section, specifically the Transwell suppression assay.

Semaphorin proteins and fragments can be produced recombinantly from the corresponding fragments of the nucleic acids using various expression systems well known in the art and a variety of host systems are suitable for production, including bacteria (e.g., *E. coli*), yeast (e.g., *Saccharomyces cerevisiae*), insect (e.g., Sf9), and mammalian cells (e.g., CHO, COS-7). Many expression vectors have been developed and are available for each of these hosts. Vectors and procedures for cloning and expression are discussed, for example, in Sambrook et al. (Sambrook et al., Molecular Cloning: A Laboratory Manual, Cold Spring Harbor Laboratory Press, Cold Spring Harbor, N.Y. (1987)) and in Ausubel et al., 1995. Standard expression vectors useful in the current invention are well known in the art and include (but are not limited to) plasmids, cosmids, phage vectors, viral vectors, and yeast artificial chromosomes. The vector sequences may contain a replication origin for propagation in *Escherichia coli* (*E. coli*); the SV40 origin of replication; an ampicillin, neomycin, or puromycin resistance gene for selection in host cells; and/or genes (e.g., dihydrofolate reductase gene) that amplify the dominant selectable marker plus the gene of interest.

In some embodiments, the DNA sequence is cloned into a vector to create a fusion protein. The fusion partner may function to allow the fusion protein to be visualized or detected. For example, the fusion partner may contain an epitope that is recognized by an antibody, a domain that binds to a peptide or nucleic acid, or a peptide that is more readily detectable. Fusion partner include, but are not limited to, HA, myc, $His_6$, Green Fluorescent Protein (GFP), glutathione-S-transferase (GST), protein A from *Staphylococcus aureus*, two synthetic IgG-binding domains (ZZ) of protein A, outer membrane protein F, β-galactosidase (lacZ), and various products of bacteriophage λ and bacteriophage T7. From the teachings provided herein, it is apparent that other proteins may be used as fusion partners. To facilitate isolation of the GNAL sequence from the fusion protein, amino acids susceptible to chemical cleavage (e.g., CNBr) or enzymatic cleavage (e.g., V8 protease, trypsin) may be used to bridge the GNAL protein and the fusion partner.

Preferably, the expression vector of the invention contains a promoter sequence. Suitable promoters, including both constitutive and inducible promoters, are widely available and are well known in the art. Commonly used promoters for expression in bacteria include promoters from T7, T3, T5, and SP6 phages, and the tip, lpp, and lac operons. Hybrid promoters (see, U.S. Pat. No. 4,551,433), such as tac and trc, may also be used. Examples of plasmids for expression in bacteria include the pET expression vectors pET3a, pET 11a, pET 12a-c, and pET 15b (see U.S. Pat. No. 4,952,496; available from Novagen, Madison, Wis.). Low copy number vectors (e.g., pPD100) can be used for efficient overproduction of peptides deleterious to the E. coli host (Dersch et al., FEMS Microbiol. Lett. 123: 19, 1994). Bacterial hosts for the T7 expression vectors may contain chromosomal copies of DNA encoding T7 RNA polymerase operably linked to an inducible promoter (e.g., lacUV promoter; see, U.S. Pat. No. 4,952,496), such as found in the E. coli strains HMS174 (DE3)pLysS, BL21(DE3)pLysS, HMS174(DE3) and BL21 (DE3). T7 RNA polymerase can also be present on plasmids compatible with the T7 expression vector. The polymerase may be under control of a lambda promoter and repressor (e.g., pGP1-2; Tabor and Richardson, Proc. Natl. Acad. Sci. USA (1985) 82: 1074, 1985).

Other promoters that may be used to control expression include, but are not limited to, cytomegalovirus (CMV) promoter (U.S. Pat. Nos. 5,385,839 and 5,168,062), the SV40 early promoter region (Benoist and Chambon, Nature 1981, 290:304-310), the promoter contained in the 3' long terminal repeat of Rous sarcoma virus (Yamamoto, et al., Cell 1980, 22:787-797), the herpes thymidine kinase promoter (Wagner et al., Proc. Natl. Acad. Sci. U.S.A. (1981) 78: 1441-1445), the regulatory sequences of the metallothionein gene (Brinster et al., Nature 1982; 296:39 42); prokaryotic expression vectors such as the β-lactamase promoter (Villa-Komaroff et al., Proc. Natl. Acad. Sci. U.S.A. (1978) 75: 3727-3731), or the tac promoter (DeBoer et al., Proc. Natl. Acad. Sci. U.S.A. 1983; 80:21-25); see also "Useful proteins from recombinant bacteria" in Scientific American 1980; 242:74-94. Still other useful promoters that may be used include promoter elements from yeast or other fungi such as the Gal4 promoter, the ADC (alcohol dehydrogenase) promoter, PGK (phosphoglycerol kinase) promoter, alkaline phosphatase promoter; and transcriptional control regions that exhibit hematopoietic tissue specificity, in particular: beta-globin gene control region which is active in myeloid cells (Mogram et al., Nature 1985; 315:338-340; Kollias et al., Cell 1986; 46:89-94), hematopoietic stem cell differentiation factor promoters, erythropoietin receptor promoter (Maouche et al., Blood 1991; 15:2557), etc.

Other regulatory sequences may also be included in expression vectors of the invention. Such sequences include an enhancer, ribosome binding site, transcription termination signal sequence, secretion signal sequence, origin of replication, selectable marker, and the like. The regulatory sequences are operably linked with one another to allow transcription and subsequent translation.

The presence of a particular codon may have an adverse effect on expression in a particular host; therefore, a nucleic acid sequence may be optimized for a particular host system, such as prokaryotic or eukaryotic cells. Methods for altering nucleotide sequences to alleviate the codon usage problem are well known to those of skill in the art (see, e.g., Kane, Curr. Opin. Biotechnol. (1995) 6: 494; Makrides, Microbiol. Rev. (1996) 60: 512; and Brown (Ed.), Molecular Biology LabFax, BIOS Scientific Publishers, Ltd. (1991), which provides a Codon Usage Table at page 245 through page 253).

Soluble forms of the protein can be obtained by collecting culture fluid, or solubilizing-inclusion bodies, e.g., by treatment with detergent, and if desired sonication or other mechanical processes, as described above. The solubilized or soluble protein can be isolated using various techniques, such as polyacrylamide gel electrophoresis (PAGE), isoelectric focusing, 2 dimensional gel electrophoresis, chromatography (e.g., ion exchange, affinity, immunoaffinity, and sizing column chromatography), centrifugation, differential solubility, immunoprecipitation, or by any other standard technique for the purification of proteins.

Alternatively, semaphorin proteins or fragments of the invention can be chemically synthesized using techniques known in the art such as, e.g., conventional Merrifield solid phase f-Moc or t-Boc chemistry. For methods of peptide synthesis see also Bodansky, "Principles of Peptide Synthesis," (Springer Verlag, Berlin (1993)) and Grant (ed.), "Synthetic Peptides: A User's Guide," (W. H. Freeman and Company, New York (1992)). In addition, automated peptide synthesizers are commercially available (e.g., Advanced ChemTech Model 396; Milligen/Biosearch 9600).

In certain embodiments, the present invention contemplates making functional variants of semaphorin molecules by modifying their structure in order to enhance therapeutic efficacy or stability (e.g., ex vivo shelf life and resistance to proteolytic degradation in vivo). Modified polypeptides can be produced, for instance, by amino acid substitution, deletion, or addition. For example, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. For additional methods, see, e.g., Levin et al., Nature, 2012, 484(7395):529-533.

The present disclosure further contemplates a method of generating sets of combinatorial mutants of the semaphorin polypeptides, as well as truncation mutants and functional variant sequences by screening combinatorial libraries. There are many ways by which a library of potential homologs can be generated from a degenerate oligonucleotide sequence. Chemical synthesis of a degenerate gene sequence can be carried out in an automatic DNA synthesizer, and the synthetic genes can then be ligated into an appropriate gene for expression. A degenerate set of genes provides, in one mixture, all of the sequences encoding the desired set of potential soluble polypeptide sequences. The synthesis of degenerate oligonucleotides is well known in the art (see, e.g., Narang, *Tetrahedron* 39:3 (1983); Itakura et al., "Recombinant DNA," (Proc. 3rd Cleveland Sympos. Macromolecules, ed. A G Walton, Amsterdam: Elsevier pp 273-289 (1981)); Itakura et al., *Annu. Rev. Biochem.* 53:323 (1984); Itakura et al., *Science* 198:1056 (1984); and Ike et al., *Nucleic Acid Res.* 11:477 (1983). Such techniques have been employed in the directed evolution of other proteins (see, e.g., Scott et al., *Science* 249:386-390 (1990); Roberts et al., *Proc. Natl. Acad. Sci. U.S.A.* 89:2429-2433 (1992); Devlin et al., *Science* 249:404-406 (1990); Cwirla et al., *Proc. Natl. Acad. Sci. U.S.A.* 87:6378-6382 (1990); and U.S. Pat. Nos. 5,223,409, 5,198,346, and 5,096,815).

Alternatively, other forms of mutagenesis can be utilized to generate a combinatorial library, including alanine scanning mutagenesis and the like (Ruf et al., *Biochemistry* 33:1565-1572 (1994); Wang et al., *J. Biol. Chem.* 269:3095-3099 (1994); Balint et al., *Gene* 137:109-118 (1993); Grodberg et al., *Eur. J. Biochem.* 218:597-601 (1993); Nagashima et al., *J. Biol. Chem.* 268:2888-2892 (1993); Lowman et al., Biochemistry 30:10832-10838 (1991); and Cunningham et al., *Science* 244:1081-1085 (1989)), linker scanning mutagenesis (Gustin et al., *Virology* 193:653-660 (1993); Brown et al., *Mol. Cell Biol.* 12:2644-2652 (1992); and McKnight et al., *Science* 232:316 (1982)); saturation mutagenesis (Meyers et al., *Science* 232:613 (1986)); by PCR mutagenesis (Leung et al., *Methods Cell. Mol. Biol.* 1:11-19 (1989)); or random mutagenesis, including chemical mutagenesis, (Miller et al., "A Short Course in Bacterial Genetics," (Cold Spring Harbor Laboratory Press, Cold Spring Harbor, N.Y. (1992); and Greener et al., *Strategies in Mol. Biol.* 7:32-34 (1994)). Linker scanning mutagenesis, particularly in a combinatorial setting, is an attractive method for identifying truncated (bioactive) forms of the subject polypeptide.

A wide range of techniques are known in the art for screening gene products of combinatorial libraries made by point mutations and truncations, and for screening cDNA libraries for gene products having a certain property. Such techniques may be adapted for rapid screening of the gene libraries generated by the combinatorial mutagenesis of the subject semaphorin polypeptides. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Some of the illustrative assays described herein (e.g., in the Example section, below) are amenable to high throughput analysis as necessary to screen large numbers of degenerate sequences created by combinatorial mutagenesis techniques.

In certain embodiments, the useful semaphorin molecules of the invention are small molecules such as a peptide and a peptidomimetic. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., *Acta Crystallogr. Section B* 35:2331 (1979)). Where no crystal structure of a target molecule is available, a structure can be generated using, for example, the program CONCORD (Rusinko et al., *J. Chem. Inf. Comput. Sci.* 29:251 (1989)). Another database, the Available Chemicals Directory (Molecular Design Limited, Informations Systems; San Leandro Calif.), contains about 100,000 compounds that are commercially available and also can be searched to identify potential peptidomimetics of the semaphorin polypeptides.

In certain embodiments, the inhibitory and agonist semaphorin polypeptides of the invention may further comprise post-translational modifications. Such modifications include, but are not limited to, acetylation, carboxylation, glycosylation, phosphorylation, lipidation, and acylation. As a result, the modified soluble polypeptides may contain non-amino acid elements, such as polyethylene glycols, lipids, poly- or mono-saccharide, and phosphates. Effects of such non-amino acid elements on the functionality of a polypeptide can be tested using the functional assays described herein.

In certain aspects, functional variants or modified forms of the semaphorin polypeptides of the invention include fusion proteins having at least a portion of the semaphorin polypeptide and one or more fusion domains. Well known examples of such fusion domains include, but are not limited to, polyhistidine, Glu-Glu, glutathione S transferase (GST), thioredoxin, protein A, protein G, and an immunoglobulin heavy chain constant region (Fc), maltose binding protein (MBP), which are particularly useful for isolation of the fusion proteins by affinity chromatography.

For the purpose of affinity purification, relevant matrices for affinity chromatography, such as glutathione-, amylase-, and nickel- or cobalt-conjugated resins can be used. Another fusion domain well known in the art is green fluorescent protein (GFP). Fusion domains also include "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain embodiments, the soluble polypeptides contain one or more modifications that are capable of stabilizing the polypeptides. For example, such modifications enhance the in vivo (e.g., circulatory) half-life of the soluble polypeptides.

In one embodiment, an isolated or purified semaphorin protein can be immobilized on a suitable affinity matrix or solid support by standard techniques, such as chemical crosslinking (e.g., direct or through one or more linker molecules), or via an antibody raised against the protein or an affinity tag or via a ligand for an affinity tag. The solid support can be any suitable solid phase or matrix, such as a bead, the wall of a plate or other suitable surface (e.g., a well of a microtiter plate), column pore glass (CPG) or a pin that can be submerged into a solution, such as in a well. Conveniently the support may be made of e.g. glass, silica, latex, plastic or any polymeric material. The support may also be made from a biodegradable material. The surface of support may be hydrophobic or hydrophilic. The support may suitably have a functionalised surface. See, e.g., U.S. Pat. Nos. 4,336,173; 4,459,378; 4,654,267. A particulate support (e.g. beads or particles) may be substantially spherical. An example of a particulate support is monodisperse particles, i.e. such which are substantially uniform in size (e.g. size having a diameter standard deviation of less than 5%). Such have the advantage that they provide very uniform reproducibility of reaction. Non-magnetic polymer beads may also be applicable. Such are available from a wide range of manufactures, e.g. Dynal Particles AS, Qiagen, Amersham Biosciences, Serotec, Seradyne, Merck, Nippon Paint, Chemagen, Promega, Prolabo, Polysciences, Agowa, and Bangs Laboratories. Another example of a suitable support is magnetic beads or particles. Magnetic beads and particles may suitably be paramagnetic or superparamagnetic. Superparamagnetic beads and particles are e.g. described in EP 0106873. Magnetic beads and particles are available from several manufacturers, e.g. Dynal Biotech ASA.

The semaphorin molecules of the invention (e.g., agonist molecules) can be also attached, covalently or non-covalently, to one or more multimerization domain(s) such as, e.g., IgG or streptavidin. Useful organic molecule-based multimers include functionalized cyclic structures such as benzene rings and dextran. See, e.g., U.S. Pat. No. 5,635, 363, US Patent Appl. Pub. No. 2004209295, PCT Publ. Nos. WO 02/072631 and WO 99/42597. Linkage to multimerization domains can be via covalent or non-covalent bonds, e.g., by chemical reactions between reactive groups of the multimerization domain (e.g. vinyl sulfone functionalities on a dextran polymer) and reactive groups on the semaphorin protein (e.g. amino groups on the protein surface), or by non-covalent interaction between a part of the semaphorin protein (e.g., a biotinylated peptide component) and the multimerization domain (e.g. four binding sites for biotin on the strepavidin tetrameric protein). Appropriate chemical reactions for the covalent coupling of semaphorins and the multimerization domain(s) include nucleophilic substitution by activation of electrophiles (e.g. acylation such as amide formation, pyrazolone formation, isoxazolone formation; alkylation; vinylation; disulfide formation), addition to carbon-hetero multiple bonds (e.g. alkene formation by reaction of phosphonates with aldehydes or ketones; arylation; alkylation of arenes/hetarenes by reaction with alkyl boronates or enolethers), nucleophilic substitution using activation of nucleophiles (e.g. condensations; alkylation of aliphatic halides or tosylates with enolethers or enamines), and cycloadditions. Appropriate molecules, capable of providing non covalent interactions between the one or more multimerization domain and the semaphorin protein, involve the following molecule pairs and molecules: streptavidin/biotin, avidin/biotin, antibody/antigen, DNA/DNA, DNA/PNA, DNA/RNA, PNA/PNA, LNA/DNA, leucine zipper e.g. Fos/Jun, IgG dimeric protein, IgM multivalent protein, acid/base coiled-coil helices, chelate/metal ion-bound chelate, streptavidin (SA) and avidin and derivatives thereof, biotin, immunoglobulins, antibodies (monoclonal, polyclonal, and recombinant), antibody fragments and derivatives thereof, leucine zipper domain of AP-1 (jun and fos), hexa-his (metal chelate moiety), hexa-hat GST (glutathione S-transferase) glutathione affinity, Calmodulin-binding peptide (CBP), Strep-tag, Cellulose Binding Domain, Maltose Binding Protein, S-Peptide Tag, Chitin Binding Tag, Immuno-reactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope, lectins that mediate binding to a diversity of compounds, including carbohydrates, lipids and proteins, e.g. Con A (*Canavalia ensiformis*) or WGA (wheat germ agglutinin) and tetranectin or Protein A or G (antibody affinity). Combinations of such binding entities are also comprised. In particular, when the MHC complex is tagged, the multimerization domain(s) can be an "anti-tag". By "anti-tag" is meant an antibody binding to the tag and any other molecule capable of binding to such tag. For multimerization techniques, see also Mekhaiel et al., Scientific Reports, 2011, 1:124.

Small Molecule Inhibitors and Agonists of the Invention

The present invention also encompasses small molecule inhibitors and agonists of Nrp1:semaphorin axis on Tregs. Small molecules are a diverse group of synthetic and natural substances generally having low molecular weights (preferably less than about 2000 Daltons, less than about 1000 Daltons, or less than about 500 Daltons). Small molecules, without limitation, may be, for example, nucleic acids, peptides, polypeptides, peptide nucleic acids, peptidomimetics, carbohydrates, lipids, or other organic (carbon containing) or inorganic molecules and may be synthetic or naturally occurring or optionally derivatized. Such small molecules may be a therapeutically deliverable substance or may be further derivatized to facilitate delivery or targeting. They can be isolated from natural sources (for example, plants, fungi, microbes and the like) or isolated from random or combinatorial chemical libraries of synthetic or natural compounds, or synthesized. See Werner et al., (2006) Brief Funct. Genomic Proteomic 5(1):32-6. Many random or combinatorial libraries are known in the art that can be used. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (N.C.), or are readily producible. Additionally, natural and synthetically produced libraries and compounds are readily modified through conventional chemical, physical, and biochemical means (Blondelle et al., (1996) Tib Tech 14:60).

Methods for preparing libraries of molecules are well known in the art and many libraries are commercially available. Libraries of interest in the invention include peptide libraries, randomized oligonucleotide libraries, synthetic organic combinatorial libraries, and the like. Degenerate peptide libraries can be readily prepared in solution, in immobilized form as bacterial flagella peptide display libraries or as phage display libraries. Peptide ligands can be selected from combinatorial libraries of peptides containing at least one amino acid. Libraries can be synthesized of peptoids and non-peptide synthetic moieties. Such libraries can further be synthesized which contain non-peptide synthetic moieties, which are less subject to enzymatic degradation compared to their naturally-occurring counterparts. Libraries are also meant to include for example but are not limited to peptide-on-plasmid libraries, polysome libraries, aptamer libraries, synthetic peptide libraries, synthetic small molecule libraries and chemical libraries. The libraries can also comprise cyclic carbon or heterocyclic structure and/or aromatic or polyaromatic structures substituted with one or more of the above-identified functional groups.

Examples of chemically synthesized libraries are described in Fodor et al., (1991) Science 251:767-773; Houghten et al., (1991) Nature 354:84-86; Lam et al., (1991) Nature 354:82-84; Medynski, (1994) BioTechnology 12:709-710; Gallop et al., (1994) J. Medicinal Chemistry 37(9):1233-1251; Ohlmeyer et al., (1993) Proc. Natl. Acad. Sci. USA 90:10922-10926; Erb et al., (1994) Proc. Natl. Acad. Sci. USA 91:11422-11426; Houghten et al., (1992) Biotechniques 13:412; Jayawickreme et al., (1994) Proc. Natl. Acad. Sci. USA 91:1614-1618; Salmon et al., (1993) Proc. Natl. Acad. Sci. USA 90:11708-11712; PCT Publication No. WO 93/20242, dated Oct. 14, 1993; and Brenner et al., (1992) Proc. Natl. Acad. Sci. USA 89:5381-5383.

Examples of phage display libraries are described in Scott et al., (1990) Science 249:386-390; Devlin et al., (1990) Science, 249:404-406; Christian, et al., (1992) J. Mol. Biol. 227:711-718; Lenstra, (1992) J. Immunol. Meth. 152:149-157; Kay et al., (1993) Gene 128:59-65; and PCT Publication No. WO 94/18318.

Screening the libraries can be accomplished by any variety of commonly known methods. See, for example, the following references, which disclose screening of peptide libraries: Parmley and Smith, (1989) Adv. Exp. Med. Biol.

251:215-218; Scott and Smith, (1990) Science 249:386-390; Fowlkes et al., (1992) BioTechniques 13:422-427; Oldenburg et al., (1992) Proc. Natl. Acad. Sci. USA 89:5393-5397; Yu et al., (1994) Cell 76:933-945; Staudt et al., (1988) Science 241:577-580; Bock et al., (1992) Nature 355:564-566; Tuerk et al., (1992) Proc. Natl. Acad. Sci. USA 89:6988-6992; Ellington et al., (1992) Nature 355:850-852; U.S. Pat. Nos. 5,096,815; 5,223,409; and 5,198,346, all to Ladner et al.; Rebar et al., (1993) Science 263:671-673; and PCT Pub. WO 94/18318.

Identification and screening of agonists and antagonists of Nrp1:semaphorin axis can be further facilitated by determining structural features of the involved proteins, e.g., using X-ray crystallography, neutron diffraction, nuclear magnetic resonance spectrometry, and other techniques for structure determination. These techniques provide for the rational design or identification of agonists and antagonists.

Compounds Affecting Nrp1 or Semaphorin Expression or the Downstream Molecular Events in Tregs As specified above, the present invention also encompasses inhibitors of Nrp1:semaphorin axis in Tregs which inhibit Nrp1 expression in Tregs, or locally (e.g., in tumors) inhibit semaphorin expression on conventional T cells, or prevent Nrp1 from engaging with its downstream signaling pathway(s).

The present invention also encompasses the agonists of Nrp1:semaphorin axis in Tregs which enhance Nrp1 expression in Tregs, or locally (e.g., in pancreatic islets for diabetes) enhance semaphorin expression on conventional T cells, or enhance Nrp1 engagement with its downstream signaling pathway(s).

Non-limiting examples of useful expression inhibitors include, e.g., interfering RNA (e.g., siRNA), dsRNA, RNA polymerase III transcribed DNAs, ribozymes, and antisense nucleic acids. Non-limiting examples of expression enhancement include, e.g., retroviral gene transfer, lentiviral gene transfer, overexpression using plasmids and transfection.

Antisense oligonucleotides, including antisense DNA, RNA, and DNA/RNA molecules, act to directly block the translation of mRNA by binding to targeted mRNA and preventing protein translation. For example, antisense oligonucleotides of at least about 15 bases and complementary to unique regions of the target DNA sequence can be synthesized, e.g., by conventional phosphodiester techniques (Dallas et al., (2006) Med. Sci. Monit. 12(4):RA67-74; Kalota et al., (2006) Handb. Exp. Pharmacol. 173:173-96; Lutzelburger et al., (2006) Handb. Exp. Pharmacol. 173:243-59).

siRNA comprises a double stranded structure typically containing 15 to 50 base pairs and preferably 21 to 25 base pairs and having a nucleotide sequence identical or nearly identical to an expressed target gene or RNA within the cell. Antisense polynucleotides include, but are not limited to: morpholinos, 2'-O-methyl polynucleotides, DNA, RNA and the like.

RNA polymerase III transcribed DNAs contain promoters, such as the U6 promoter. These DNAs can be transcribed to produce small hairpin RNAs in the cell that can function as siRNA or linear RNAs that can function as antisense RNA. The inhibitor may be polymerized in vitro, recombinant RNA, contain chimeric sequences, or derivatives of these groups. The inhibitor may contain ribonucleotides, deoxyribonucleotides, synthetic nucleotides, or any suitable combination such that the target RNA and/or gene is inhibited. In addition, these forms of nucleic acid may be single, double, triple, or quadruple stranded. (see for example Bass (2001) Nature, 411, 428 429; Elbashir et al., (2001) Nature, 411, 494 498; and PCT Publication Nos. WO 00/44895, WO 01/36646, WO 99/32619, WO 00/01846, WO 01/29058, WO 99/07409, WO 00/44914).

Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hammerhead motif ribozyme molecules that specifically and efficiently catalyze endonucleolytic cleavage of mRNA sequences are also within the scope of the present invention. Scanning the target molecules for ribozyme cleavage sites that include the following sequences, GUA, GUU, and GUC initially identifies specific ribozyme cleavage sites within any potential RNA target. Once identified, short RNA sequences of between about 15 and 20 ribonucleotides corresponding to the region of the target gene containing the cleavage site can be evaluated for predicted structural features such as secondary structure that may render the oligonucleotide sequence unsuitable. The suitability of candidate targets can also be evaluated by testing their accessibility to hybridization with complementary oligonucleotides using, e.g., ribonuclease protection assays.

Expression inhibitors of the present invention can be prepared by known methods. These include techniques for chemical synthesis such as, e.g., by solid phase phosphoamite chemical synthesis. Alternatively, antisense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. See, e.g., Weintraub, H. et al., Antisense RNA as a molecular tool for genetic analysis, Reviews—Trends in Genetics, Vol. 1 (1) 1986.

Various modifications to the oligonucleotides of the present invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Aptamers nucleic acid sequences are readily made that bind to a wide variety of target molecules. The aptamer nucleic acid sequences of the invention can be comprised entirely of RNA or partially of RNA, or entirely or partially of DNA and/or other nucleotide analogs. Aptamers are typically developed to bind particular ligands by employing known in vivo or in vitro (most typically, in vitro) selection techniques known as SELEX (Systematic Evolution of Ligands by Exponential Enrichment). Methods of making aptamers are described in, for example, Ellington and Szostak (1990) Nature 346:818, Tuerk and Gold (1990) Science 249:505, U.S. Pat. No. 5,582,981; PCT Publication No. WO 00/20040; U.S. Pat. No. 5,270,163; Lorsch and Szostak (1994) Biochem. 33:973; Mannironi et al., (1997) Biochem. 36:9726; Blind (1999) Proc. Nat'l. Acad. Sci. USA 96:3606-3610; Huizenga and Szostak (1995) Biochem. 34:656-665; PCT Publication Nos. WO 99/54506, WO 99/27133, and WO 97/42317; and U.S. Pat. No. 5,756,291.

In one specific embodiment, the inhibitor of Nrp1:semaphorin axis inhibits a signaling pathway between the cytoplasmic domain of Nrp1 protein comprising the C-terminal amino acid sequence SEA (C-terminal PDZ domain-binding motif) and PTEN protein; such inhibitor can be, e.g., a peptide or a small molecule or a fragment of Nrp1 protein comprising all or part of its cytoplasmic domain comprising the C-terminal amino acid sequence SEA or a derivative or an analog thereof.

Methods for Administering Compositions
Comprising Inhibitors or Agonists of the Invention In certain embodiments, the inhibitors and agonists of the invention are formulated in pharmaceutical compositions with a pharmaceutically acceptable carrier or excipient. The compounds can be formulated for administration in any convenient way for use in human or veterinary medicine. Wetting agents, emulsifiers and lubricants, such as sodium lauryl sulfate and magnesium stearate, as well as coloring agents, release agents, coating agents, preservatives and antioxidants can also be present in the compositions.

The formulations may conveniently be presented in unit dosage form and may be prepared by any methods well known in the art. The amount of active ingredients that can be combined with a carrier material to produce a single dosage form will vary depending upon the host being treated and the particular mode of administration. The amount of active ingredients that can be combined with a carrier material to produce a single dosage form will generally be that amount of the compound which produces a therapeutic effect.

In general, the formulations can be prepared with a liquid carrier, or a finely divided solid carrier, or both, and then, if necessary, shaping the product.

Formulations for oral administration may be in the form of capsules, cachets, pills, tablets, powders, granules, or as a solution or a suspension in an aqueous or non-aqueous liquid, or as an oil-in-water or water-in-oil liquid emulsion, and the like, each containing a predetermined amount of one or more active ingredients.

In solid dosage forms for oral administration (capsules, tablets, pills, dragees, powders, granules, and the like), one or more active ingredients can be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Suspensions, in addition to one or more active ingredients, can contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

Compositions of the invention can be also administered topically, either to skin or to mucosal membranes. This offers the greatest opportunity for direct delivery with the lowest chance of inducing side effects. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The subject therapeutic agents may be mixed under sterile conditions with a pharmaceutically acceptable carrier, and with any preservatives, buffers, or propellants which may be required. The ointments, pastes, creams and gels may contain, in addition to a subject polypeptide agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to one or more active ingredients, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

Pharmaceutical compositions suitable for parenteral administration may comprise one or more active ingredients in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

Injectable depot forms can be made by forming microencapsule matrices of one or more active ingredients in biodegradable polymers such as polylactide-polyglycolide. Depending on the ratio of active ingredient to polymer, and the nature of the particular polymer employed, the rate of antagonist release can be controlled. Examples of other biodegradable polymers include poly(orthoesters) and poly (anhydrides). Depot injectable formulations are also prepared by entrapping the antagonists in liposomes or microemulsions which are compatible with body tissue.

Formulations for intravaginal or rectal administration may be presented as a suppository, which may be prepared by mixing one or more active ingredients with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1

Materials and Methods

Mice.

C57/BL6 and dnTGFβRII mice were purchased from the Jackson Laboratories. Foxp3$^{YFP-iCre}$, Foxp3$^-$ and Foxp3$^{DTR-gfp}$ mice were obtained from A. Y. Rudensky (HHMI/Washington University; see Rubtsov et al., Immunity, 2008, 28:546-558; Fontenot et al., Nat Immunol., 2003, 4(4):330-336; Kim et al., Nat Immunol., 2007, 8(2):191-197). Il10$^{-/-}$ mice were obtained from T. Geiger (St. Jude Children's Research Hospital; see Selvaraj and Geiger, J Immunol., 2008, 180(5):2830-2838). Nrp1$^{f/f}$ mice were obtained from D. Cheresh (UCSD; see Acevedo et al., Blood, 2008, 111(5):2674-2680). Foxp3$^-$×CD45.1 mice were bred from heterozygous crosses. Animal experiments were performed in American Association for the Accreditation of Laboratory Animal Care-accredited, specific-pathogen-free facilities in the St. Jude Animal Resource Center. Animal protocols were approved by the St Jude Animal Care and Use Committee.

Nrp1 and Semaphorin Antibodies.

Mouse Sema-3a, mouse Nrp1 and human Sema4a-Ig were purchased from R&D Biosystems. Two different Nrp1 blocking antibodies were used in the experiments: (i) R&D AF566 are anti-Nrp1 mouse/rat affinity purified polyclonal antibodies (Goat IgG), and (ii) anti-Nrp1 monoclonal antibodies (Rat IgG2a), provided by R&D Biosystems (R&D Systems, clone 761704, MAB59941). The following antibodies to semaphorin-4a (Sema4a) were used: clone 5E3 from MBL International and monoclonal antibodies from R&D Biosystems (clone 757129) (see, e.g., FIGS. 1E, 2H, 4I). Sema4a staining antibody was purchased from MBL International (clone 5E3), and conjugated to biotin or Alexa Fluor 647 in-house. Most flow cytometric antibodies were purchased from BioLegend. Anti-Foxp3 and anti-Eomes were purchased from eBioscience. KLF2 antibody was purchased from Millipore. Phospho-Akt (S473), phospho-S6K1 (T421/S424), Foxo3a, and pan Akt antibodies were purchased from Cell Signaling Technologies. PTEN-HRP antibody was purchased from Santa Cruz Biotechnology.

RNA Interference.

Control siRNA (Catalog #4390843) and pools of Sema4a (Catalog #4390771, siRNA# s73547) siRNA were purchased from Life Technologies and resuspended per the manufacturer's instructions. CD4$^+$ and CD8$^+$ conventional T cells were sorted magnetically by negative selection and transfected by Amaxa (Lonza) with 300 pMol siRNA and 2 µg of pMaxGFP control plasmid, rested overnight in Amaxa nucleofector media. Cells were then sorted based on GFP, CD25, and CD45RB expression and cocultured with Treg cells in the top well of a transwell suppression assay.

Plasmids.

Nrp1.mCherry was obtained from Addgene and used as a template to generate retroviral overexpresion constructs. Nrp1$^{WT}$ was generated by adding the native signal sequence and cloned into pMlCherry. Nrp1$^{\Delta SEA}$ was generated from the WT construct, deleting the terminal SEA motif by mutation of the serine codon to a stop codon. Akt$^{WT}$, Akt$^{DN}$ (dominant-negative kinase dead K179M as described by Franke et al., Cell, 1995, 81:727-736), and pBabe empty vector were obtained from D. R. Green (described in Morgenstern J P, Land H., 1990, Nucleic Acids Research 18(12): 3587-96).

Human T Cell Populations.

Human umbilical cord samples were provided by B. Triplett, M. Howard and M. McKenna at the St. Louis Cord Blood Bank, and were obtained from the umbilical vein immediately after vaginal delivery with the informed consent of the mother and approved by St. Louis Cord Blood Bank Institutional Review Board (IRB). Research use approved by the St. Jude IRB.

Transwell Suppression.

1.25×10$^4$ Treg purified by FACS (CD45RB$^{lo}$ Foxp3$^{YFP-iCre+}$) were stimulated in the top chamber of a Millipore Millicell 96 (0.4 µm pore size) in the presence of sorted Tconv (CD45RB$^{hi}$ CD25$^-$CD4$^+$ or CD8$^+$), B cells (B220$^+$), or Treg at a 1:4 ratio, Sema4a-Ig or IgG-conjugated latex beads (1:1 ratio), anti-CD3 (145.2C11) and anti-CD28 (37.51) (obtained from BioLegend) conjugated latex beads (purchased from Life Technologies) (1:1 ratio), and/or neutralizing antibodies. In some experiments, the top well co-cultured cells were fixed with 2% PFA for 15 minutes and washed extensively before co-culture with Treg. 2.5×10$^4$ purified Treg were stimulated in the bottom well with anti-CD3/anti-CD28 beads at a 1:1 ratio. Cells were cultured for 72 hours and pulsed with $^3$[H]-thymidine for the final 8 hours. The bottom chambers were harvested and read with a beta counter.

For human studies, sorted umbilical cord blood Tconv (CD4$^+$CD25) and Treg (CD4$^+$CD25$^+$) were activated with 3 µg/mL plate-bound anti-CD3 (clone OKT3, Biolegend), 2 µg/mL soluble anti-CD28 (clone CD28.1, Biolegend), and 100 U/mL rhIL-2 (St. Jude Pharmacy) for 7-9 days. After harvesting and washing, Treg were stimulated at a 1:200 ratio with fixed autologous Tconv or IgG/Sema4a-Ig coated latex beads in the top well of a transwell plate. 2.5×10$^4$ Tconv were stimulated in the bottom well at a 1:1 ratio with OKT3/CD28.1 coated latex beads. Cells were cultured for 5 days and pulsed with $^3$[H]-thymidine for the final 8 hours. The bottom chambers were harvested and read with a beta counter.

"Percent transwell suppression" is defined as 100−100× [(CPM of a particular well)/(Average CPM of unsuppressed cells)] to normalize across experiments.

Fusion Proteins.

The sequence encoding the extracellular domains of Sema4a or Nrp1 was cloned in-frame to pX-Ig to create a Sema4a- or Nrp1-mouse IgG1-Fc fusion protein construct (Sema4a-Ig or Nrp1-Ig). J558L B cells were electroporated with this construct, and high producing clones were selected by single-cell sorting. High producing clones were seeded into Sartorious Bioreactors and harvested for protein G purification and concentration. Sulfate latex 4 µm beads (Life Technologies) were conjugated with isotype control (mouse IgG1, MOPC21, R&D Biosystems) or Sema4a-Ig overnight with 3 pg protein per bead, blocked with 10% FBS, and stored in media. Mouse Sema-3a-Fc, Sema4a-Fc, mouse Nrp1, and human Sema4a-Fc were purchased from R&D Systems.

Binding Assays.

High protein binding plates were coated with 500 ng/mL recombinant murine Nrp1 (R&D Systems) overnight in PBS. After a 1-2 h block in 1% BSA in PBS at room temperature, coated plates were incubated with various concentrations of Sema4a-Ig or mouse IgG1 for 2-4 hours in the presence of anti-Sema4a, anti-Nrp1, or isotype control antibodies. Plates were then washed with PBS+0.05% TWEEN-20 10 times and incubated with 500 ng/mL biotinylated anti-mouse IgG1 antibody (BD Biosciences) to bind the fusion protein (or mouse IgG1 control). After 7 washes, Streptavidin-HRP (GE Healthcare) was added at 500 ng/mL to detect the biotinylated antibody. After another 7 washes, TMB substrate (Thermo Scientific) was added and stopped with 1N $H_2SO_4$.

For VEGF binding, the same protocol was followed, except rather than Sema4a-Ig being used, VEGF165 (R&D Systems) was used at 50 ng/mL in PBS and detected with 500 ng/mL anti-VEGF-biotin (R&D Systems) followed by SA-HRP for detection. For comparisons across Sema family members, plates were coated with varying concentrations of Sema3a-Fc, Sema4d-Fc, Sema4a-Ig, or isotype control overnight. Biotinylated Nrp1-Ig was added and incubated for 3 hours, and SA-HRP was used for detection.

mRNA Analysis.

RNA was extracted from cells lysed in TRIzol reagent (Life Technologies) and reverse transcribed with the High Capacity Reverse Transcription kit (Applied Biosystems). Real-time PCR was performed using primers and probes and TaqMan master mix or SYBR green chemistry (Applied Biosystems).

Rescue of Foxp3-Deficient Autoimmunity.

CD45.1×Foxp3$^{+/-}$ female mice were bred to CD45.1 male mice in timed breedings. Male progeny were genotyped at birth for Foxp3$^-$ status. 1×10$^6$ purified Foxp3$^{Cre}$ or Nrp1$^{f/f}$Foxp3$^{Cre}$ CD45.2$^+$ Tregs, purified by flow cytometry, were injected intraperitoneally into Foxp3$^-$ male pups within 3 days of birth. Mice were monitored for the scurfy phenotype (scaly skin, eye inflammation, runted phenotype, and lack of mobility). For some experiments, all mice were sacrificed at 5 weeks for histological analysis of the ear pinna, liver, and lung.

Tumor Models.

Foxp3$^{Cre}$, Nrp1$^{f/f}$Foxp3$^{Cre}$, or Foxp3$^{DTR-gfp}$ mice were injected with B16.F10 melanoma (1.25×10$^5$ cells i.d.), EL4 thymoma (1.25×10$^5$ cells i.d.), or MC38 colon carcinoma (2.5×10$^5$ cells s.c.). Tumors were measured regularly with digital calipers and tumor volume calculated. Tumors and lymph nodes were harvested for analysis. TILs were prepared using a Percoll gradient from tumor samples after mechanical disruption. For metastasis studies, B16.F10 was injected intravenously at various doses. After 17-20 days, lungs were harvested, inflated with $H_2O_2$, and metastases were counted. Therapeutic B16 experiments were conducted by injecting 1.25×10$^5$ B16 melanoma cells i.d. and waiting until tumors were palpable (5 days). On day 5, mice began receiving intraperitoneal injections of either rat IgG2a or anti-Nrp1 (R&D Systems, clone 761704) (400 µg initial dose and 200 µg every three days).

Experimental Colitis.

6-to-8 week old RAG2$^{-/-}$ mice were injected intraperitoneally with 4×10$^5$ congenitally marked CD45RB$^{hi}$ CD25$^-$ Tconv cells. 21 to 28 days later (when the majority of the mice had lost 5% body weight and had colitis symptoms), 1×10$^6$ Foxp3$^{Cre}$ or Nrp1$^{f/f}$Foxp3$^{Cre}$ Treg were injected intraperitoneally. Body weight was measured daily, and 28 days after Treg rescue, sections were stained for histology.

Signaling Analysis.

For flow cytometry, Treg were stimulated with anti-CD3e/anti-CD28 coated beads and either purified conventional T cells or Sema4a-Ig beads for various times, then fixed with 1% PFA for 15 minutes at 37° C. Cells were then permeabilized in ice-cold 90% MeOH for 20 min at −20° C. After extensive washing in PBS, cells were blocked with 10% normal mouse serum in PBS for 10 minutes at RT. Cells were then stained with antibodies in 1% BSA in PBS (pAkt (T308), pAkt (S473)) for 1 hour at RT in the dark. Finally, cells were stained with appropriate secondary antibodies for 30 minutes at RT in the dark, then washed and analyzed. For immunoblot analysis, Treg were expanded with 1 ng/mL phorbol-13-myristol acetate and 10 ng/mL ionomycin with 500 U rhIL-2 for 3 days, then washed extensively with media, and expanded to 10× volume in 500 U rhIL-2. After an overnight rest with no IL-2, Treg were stimulated with plate-bound anti-CD3, soluble anti-CD28 and bead-bound Sema4a-Ig for 3 hours, then lysed in whole cell lysis buffer (1% NP40, 5 mM EDTA, 5 mM EGTA, TWEEN-20) for 15 min on ice. In some experiments, 3×10$^6$ Treg were lysed in a larger volume, and cleared lysates were incubated with Protein G beads for 3 hours to "preclear" the lysate. Nrp1 was immunoprecipitated using a polyclonal anti-Nrp1 antibody (R&D AF566) overnight followed by a 3 hour incubation with Protein G beads. Beads were washed with lysis buffer before elution and reduction prior to immunoblotting. Briefly, precipitates or input lysates were incubated at 100° C. with 2-mercapto-ethanol and 4×LDS sample buffer (Life Technologies), then loaded into 4-12% Bis-Tris NuPAGE gels (Life Technologies), and run for 1 hour at 200V. Separated gels were electrotransferred to PVDF membranes using the Criterion Gel Blotting System (Biorad), and blocked for 1 hour at room temperature with 3% BSA in TBS supplemented with 0.1% TWEEN20. Blocked membranes were incubated overnight with anti-PTEN directly conjugated to HRP, washed three times with TBS-TWEEN, and imaged using Western Lightning ECL.

Retroviral Transduction.

293T cells were transfected with pPAM-EQ and pVSV-G packaging plasmids with various retroviral constructs to transduce GPE86 retroviral producer cells. Treg cells were purified flow cytometrically. Treg were activated and cycled with PMA and ionomycin in the presence of 500 U/mL rhIL-2 for 24 h in 96 well flat bottom plates at 5×104 per well in 100 µL. Viral supernatants were concentrated using 100 kDa MWCO concentrators (Millipore) 10 fold and added in equal volume to cycling Treg cells in the presence of 500 U/mL rhIL-2 and 6 μg/mL polybrene and centrifuged at 2500 rpm for 60 min at 37 deg, then incubated for 24 h. The spinduction process was repeated twice every 24 h, removing 100 μL of supernatant from the cultured Treg each day to keep the culture volume at 200 μL per well. Treg cells were then washed in media and sorted based on fluorescent protein expression or selected with 1 μg/mL puromycin and expanded further in IL-2. Fluorescent protein or intracellular epitope staining (anti-HA, Sigma) was confirmed prior to use. Functional assays were performed after a 24 h rest without IL-2.

Microscopy.

TIRF illumination of IS activation was performed as previously described[50]. Briefly, lipid bilayers containing anti-TCR and an anti-mouse IgG1 capture antibody loaded with Sema4a-Ig or isotype control were prepared. Treg cells were stimulated on the bilayer for 20 minutes, then fixed, permeabilized, and stained for phospho-Akt (S473), global phosphotyrosine (4G10), or Nrp1. "Percentage of pAkt+ TCR clusters" represents the ratio of phosphorylated Akt (S473) positive synapses to the total number of synapses formed as read-out by TCR clustering. Foxo3a was performed on freshly isolated Treg left unstimulated in media overnight or stimulated with immobilized anti-CD3/anti-CD28 in the presence or absence of immobilized Sema4a-Ig or its isotype control. Cells were harvested, fixed in 1% PFA, and permeabilized with 0.1% Triton X-100 in TBS. After blocking with normal mouse serum, cells were stained with anti-Foxo3a (Cell Signaling Technologies) overnight in Tris-buffered 1% BSA. After several washes, cells were stained with Alexa Fluor 647 conjugated anti-rabbit IgG (Life Technologies), and then washed several times. Cells were then loaded with DAPI and phalloidin-Alexa Fluor 546 or 488 prior to microscopy. Random fields of 10-30 cells were visualized using spinning-disc laser scanning confocal microscopy. Blinded masks were generated using phalloidin and DAPI staining to determine cytoplasmic and nuclear volume, respectively, and only then was the Foxo3a staining visualized. The nuclear and cytoplasmic volumes of Foxo3a fluorescence of 20-30 stacks were calculated using Slidebook (3i, Inc.) software in arbitrary fluorescence units and analyzed in Graphpad Prism.

Affymetrix Array and Analysis.

Foxp3$^{Cre}$ or Nrp1$^{f/f}$Foxp3$^{Cre}$ Treg were flow cytometrically sorted to 99.0% purity from 6-8 week old mice, and stimulated 48 hours with plate-bound anti-CD3, anti-CD28, 100 U/mL rhIL-2, and either isotype or Sema4a-Ig coated latex beads. Cells were harvested, washed three times with PBS, and lysed in TRIzol reagent (Life Technologies). Quality was confirmed by UV spectrophotometry and by analysis on an Agilent 2100 Bioanalyzer (Agilent Technologies, Santa Clara, Calif.). Total RNA (100 ng) was processed and labeled in the Hartwell Center for Biotechnology & Bioinformatics according to the Affymetrix 3' IVT Express protocol and arrayed on a mouse high throughput 430 PM GeneChip array. Signal data was RMA summarized, visualized, quality checked by principal component analysis (PCA) (Partek Genomics Suite 6.6 St Louis Mo., USA). Batch correction was applied as needed to correct differences in completely replicated experiments scanned on distinct dates. To compare Tconv cells to resting Tregs and unequal variance t test was applied to each probeset and the log 2 ratio calculated. This same analysis was used to compare T conv cells to activated Treg cells. To compare the effect of Sema4a treatment in wild-type Treg cells to the effect of sema treatment in Nrp1-deficient cells a two factor ANOVA interaction of treatment and genotype was applied to each probeset and the Storey q value was found to correct for multiple comparisons. The categorical mean of each probeset was found, transformed to a Z-score, hierarchically clustered and visualized by heat-map in Spotfire Decision-Site 9.1 (Tibco, Somerville Mass., USA) (FIG. 1A). The heat map in FIG. 11B was composed of the top named genes that had the passed p value interaction FDR at 10%, had a minimum mean expression of 6 in one class and a minimum absolute value logratio difference of at least 0.5. The volcano plots were generated using STATA/SE 11.1 (College Station Tex., USA). For all volcano plots genes without official symbols or names were removed. In these plot score refers to the –log base 10 transformed p value. For the interaction volcano plot genes a metric for distance from the origin was applied to color code the graph |(score/10+|log ratio difference|)/2|>0.5. Statistical tests and multiple comparison corrections were performed using Partek Genomics Suite 6.6 (St Louis Mo., USA). Sequences were retrieved for probesets that had at least a 3 fold difference between Tconv and activated Treg cells and a p value of 0.01 and these sequences were then tested with SignalP 3.0 software to identify transmembrane domains.

Results

Semaphorin 4a is a Tconv-Expressed Ligand that Stimulates Treg Activity

The present inventors and co-workers have previously suggested that the transcriptional and functional profile of Tregs stimulated in the presence or absence of co-cultured conventional CD4$^+$ T cells (Tconv) is markedly different[12,13]. Tregs can only suppress Tconv across a permeable Transwell membrane when in direct contact with Tconv placed in the top chamber (referred to herein as Transwell suppression), suggesting a contact-dependent mechanism that enhances Treg function[12]. The present inventors sought to determine the signals that induce this distinct Treg activity and transcriptional profile. They hypothesized that Tregs could not 'self-boost' suggesting that the ligand that mediates this activity may be expressed by Tconv but not by Tregs. Indeed, Treg stimulated alone or in co-cultured with additional live or fixed Foxp3$^+$ Tregs or B220$^+$ B cells could not mediate suppression across a Transwell membrane in a Transwell suppression assay of Tconv stimulated with anti-CD3/anti-CD28 coated beads in the bottom well when regulatory T cells (Tregs) were stimulated in the top well (FIG. 1A). In contrast, Tregs co-cultured with fixed CD4$^+$ or CD8$^+$ T cells could potentiate Transwell suppression, suggesting that the ligand was cell-surface expressed[12]. Gene expression was compared between resting and activated Treg and CD4$^+$ Tconv cells using Affymetrix analyses of Tconv and Treg populations sorted from Foxp3.GFP mice and incubated together or separately with irradiated APC in the presence or absence of anti-CD3 antibody (after 48 hours, RNA extracted from cells re-sorted based on CD4 and GFP expression was subjected to Affymetrix analysis). This list was curated to focus on gene encoding cell surface-expressed proteins that were predominantly expressed by Tconv. From this list, the top three genes, Sema4a (semaphorin-4a), Tgfbr3 (transforming growth factor, beta receptor III) and Itgb3 (integrin beta 3; CD61), were selected for further study based on previous studies implicating their roles in immunoregulation and confirmation of their differential expression in CD4$^+$ Tconv cells versus Tregs and B220$^+$ B cells by qPCR. Whereas Sema4a and Tgfbr3 were also enhanced in CD8+ T cells, Itgb3 was not. The inventors then sought to identify a cell line that could be used to assess the capacity of these molecules to potentiate Treg function. It was found that 3T3 fibroblasts expressed high amounts of Tgfbr3 and Itgb3 but could not mediate Treg boosting. In contrast 3T3 cells did not express Sema4a. Taken together, these data suggested that Sema4a, which has been shown to modulate axon activity and immune regulation[14], warranted further investigation.

Four approaches were used to determine if Sema4a was required and sufficient to potentiate Treg function.

First, dose-dependent inhibition of Treg boosting by Tconv in a Transwell suppression assay was observed with a Sema4a blocking mAb (clone 5E3, MBL International) (FIG. 1B). Second, siRNA knockdown of Sema4a expression in CD4+ and CD8+ Tconv cells limited their ability to boost Treg suppression. This was determined (i) in a Transwell suppression assay after CD4+ or CD8+ Tconv were mock transfected or transfected with scrambled siRNA or Sema4a siRNA and (ii) after CD4+ and CD8+ T cells enriched using negative magnetic separation and nucleofected with 200 pM scrambled (siControl) or a pool of 3 Sema4a-targeting (Life Technologies Catalog #4390771, siRNA# s73547) (siSema4a) siRNA were resorted and stimulated 16 hours after transfection with anti-CD3 and anti-CD28 for 24 hours followed by RNA extraction and performing qPCR for Sema4a mRNA (FIG. 1C).

Figure 4:
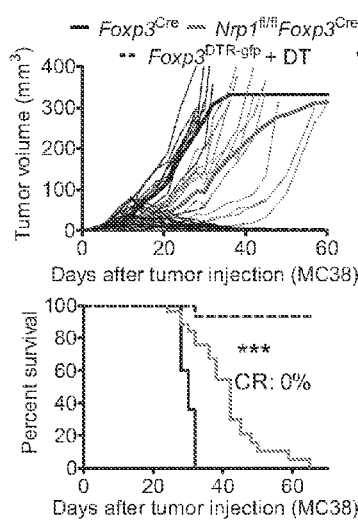
FIGS. 4A-J demonstrate that Nrp1-deficient Tregs fail to suppress anti-tumor responses or highly inflammatory colitis. A, Tumor growth curve (top) and survival plot (bottom) of Foxp3$^{Cre}$ and Nrp1$^{f/f}$Foxp3$^{Cre}$ mice receiving 1.25×10⁵ MC38 melanoma cells s.c. B, As in A, but mice received 1.25×10⁵ EL4 thymoma i.d. C, As in A, but mice received 1.25×10⁵ B16 melanoma i.d. D, Lung metastasis counts from Foxp3$^{Cre}$ or Nrp1$^{f/f}$Foxp3$^{Cre}$ mice injected with 2.5-10×10⁵ B16 cells i.v. 17-20 days earlier. E, Tabulation of flow cytometric analysis of tumor-infiltrating lymphocytes from Foxp3$^{Cre}$ or Nrp1$^{f/f}$Foxp3$^{Cre}$ mice injected i.d. with B16 18 days earlier. F, Tumor growth curve of C57/BL6 mice receiving 1.25×10⁵ B16 melanoma i.d. When tumors were palpable (day 5, indicated by arrow), mice began receiving injections of anti-Nrp1 or its isotype control (400 μg initial dose, 200 μg every 3 days). G, Histology of large intestine of Rag2$^{−/−}$ mice that had or had not received 4×10⁵ CD4⁺CD45RB⁺CD25⁻ cells to induce colitis, then PBS or 1×10⁶ Tregs from Foxp3$^{Cre}$ or Nrp1$^{f/f}$Foxp3$^{Cre}$ mice after colitis was detected. H, Sema4a expression of various immune cells in ndLN, dLN, or TIL. I, Tumor growth curve of C57/BL6 mice receiving 1.25×10⁵ B16 melanoma i.d. concomitant with injections of isotype control, anti-Sema4a, or anti-Nrp1 (100 μg) twice weekly. J, Tumor growth curve as in g except mice received Sema4a-Ig twice weekly. Results represent the mean of five (A-C, I-J n=10-25 mice), three (D, E, F, H n=8-17 mice), or four (G) experiments. *, p<0.05, , p<0.01, *, p<0.001, by (A-C, I-J) one-way ANOVA or (D-F, H) unpaired t-test.
Figure 4:
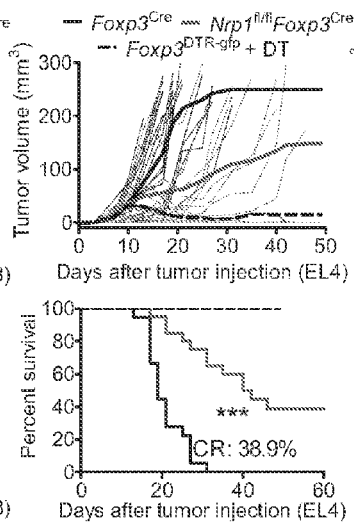
Figure 4:
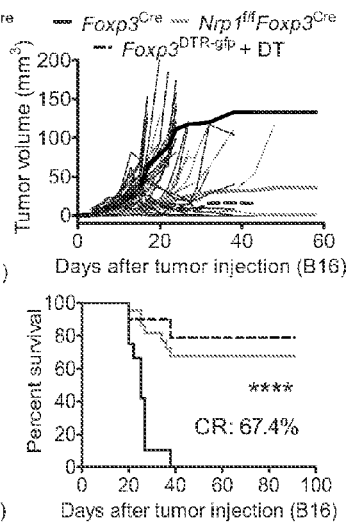
Figure 4:
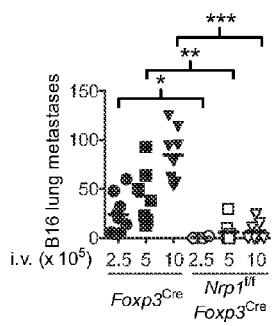
Figure 4:
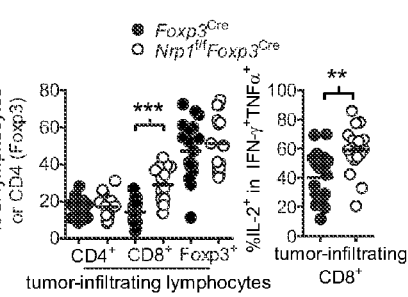
Figure 4:
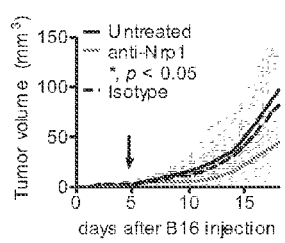
Figure 4:
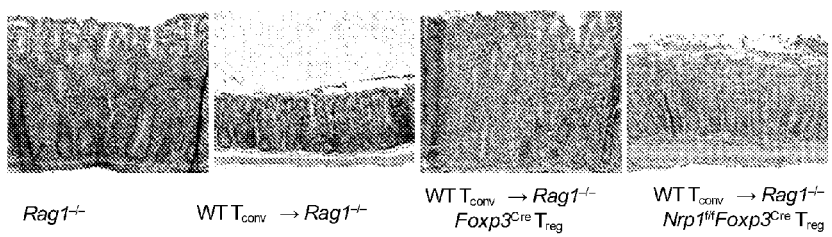
Figure 4:
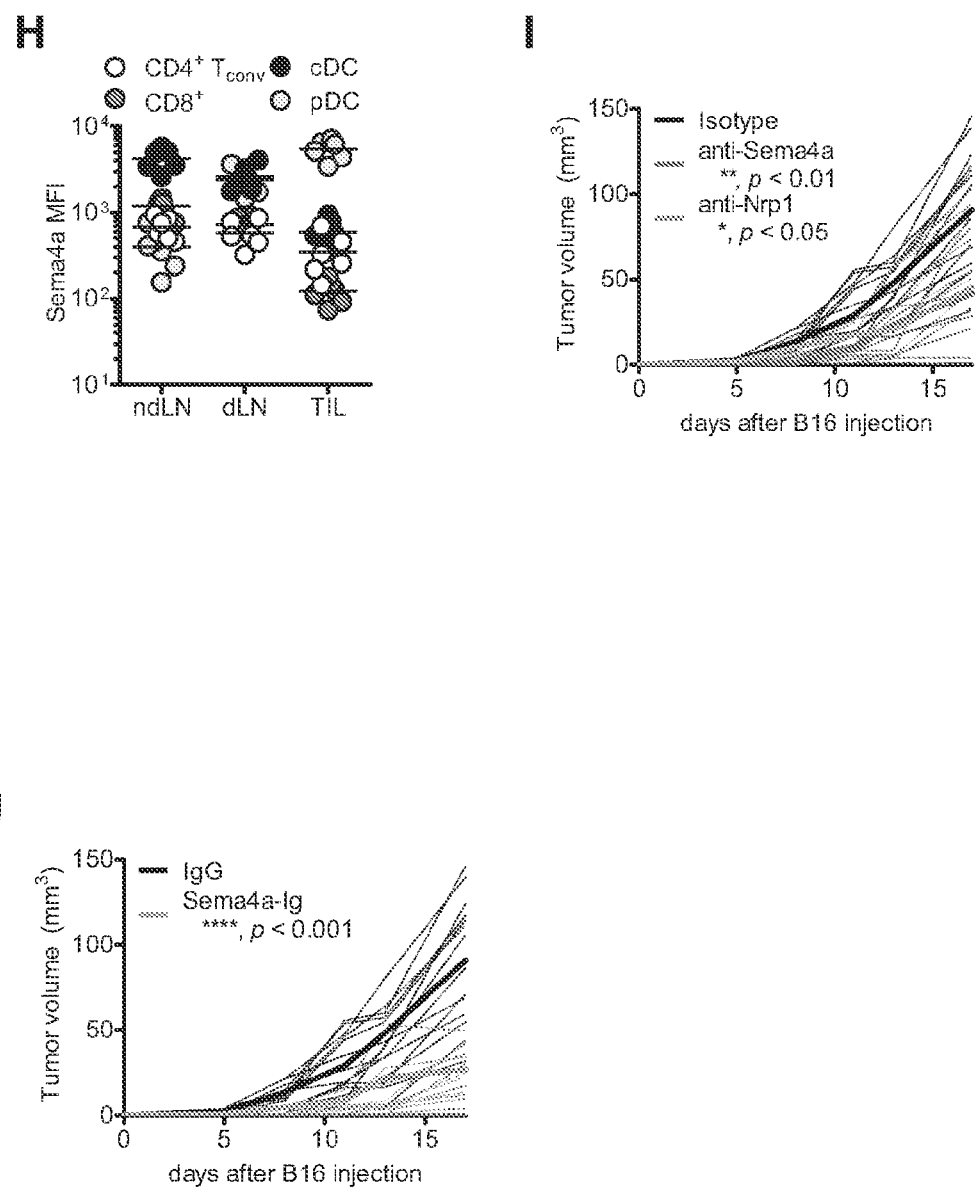

Third, whereas Sema4a loss variants of the 3A9 T cell hybridoma failed to boost Treg function in a Transwell assay, Sema4a+ clones or Sema4a transfectants of the Sema4a loss variant potentiated Treg suppression (FIG. 4). Sema4a 3T3-transfectants (transduced with a retrovirus expressing a Sema4a overexpression construct), but not empty vector control cells, also potentiated Treg Transwell suppression.

Fourth, a murine Sema4a-Ig fusion protein, but not an IgG1 isotype control, coated on to beads was sufficient to induce potent Transwell suppression to an extent equivalent to Tconv cells (FIG. 1D).

In addition, an anti-Sema4a antibody showed dose-dependent inhibition of $T_{reg}$ potentiation (FIG. 1E). It was then assessed if other immune cells expressed Sema4a. While CD4+ and CD8+ T cells displayed low but demonstrable Sema4a expression, lymph node CD11c+ dendritic cells (DCs) and DX5+ natural killer cells appeared to express high levels of Sema4a (as determined in peripheral spleen/lymph node preparations stained with anti-Sema4a and analyzed flow cytometrically). Interestingly, lymph node CD11c+ DCs could potentiate $T_{reg}$ suppression in Sema4a-dependent manner (FIG. 1E).

It was next determined if Sema4a was sufficient to potentiate $T_{reg}$ function. Sema4a 3T3-transfectants, but not empty vector control cells, could potentiated $T_{reg}$ Transwell suppression. Importantly, a murine Sema4a-Ig fusion protein, but not an IgG1 isotype control, coated onto beads was sufficient to induce Transwell suppression to an extent equivalent to $T_{conv}$ cells (FIG. 1D).

Collectively, these data suggest that Sema4a is required and sufficient to potentiate Treg function in vitro.

Nrp-1 is aSema4a Receptor Required to Boost Treg Function and Survival

Neuropilin-1 (Nrp1) is a co-receptor for a class III semaphorin, Sema3a, with key roles in controlling axonal guidance[15]. Nrp1 induces axon growth cone collapse, preventing infiltration into privileged tissues and genetic deletion in mice results in embryonic lethality[16]. Nrp1 has also been shown to interact with vascular-endothelial growth factor (VEGF), platelet derived growth factor beta (PDGFβ) and transforming growth factor beta (TGFβ)[17,18]. Nrp1 has been shown to be highly expressed in Tregs and is a useful marker, especially in thymically derived "natural" Treg (as determined by flow cytometric analysis of Foxp3 and neuropilin expression in CD4+ T cells in Foxp3$^{Cre}$ and Nrp1$^{f/f}$Foxp3$^{Cre}$ mice)[19-21]. Although a role for Nrp1 in T cells has been implicated[22], no role for Nrp1 in Tregs has been identified.

Figure 2:
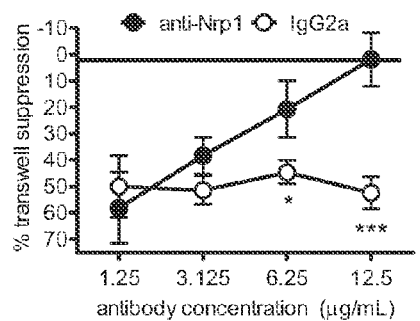
FIGS. 2A-I demonstrate that Nrp1 acts as the ligand for Semaphorin-4a on Tregs. A, Transwell suppression assay in which Tconv:Treg cocultures were stimulated in the presence of an neutralizing anti-Nrp1 antibody or its isotype control. B, Transwell suppression assay with Foxp3$^{Cre}$ or Nrp1$^{f/f}$ Foxp3$^{Cre}$ Tregs. C, Transwell suppression assay using WT, IL-10$^{-/-}$, or Ebi3$^{-/-}$ Treg in the top well cocultured with Sema4a-Ig beads and WT or dnTGFbRII Tconv in the bottom well. D, Transwell suppression assay using Tregs cultured with Sema4a-Ig beads in the presence or absence of neutralizing antibodies to IL-10 and IL-35. E, Tabulation of flow cytometric analysis of Annexin V and 7-AAD staining in Treg 48 hours after stimulation with anti-CD3/CD28 coated beads, IL-2, and either isotype or Sema4a-Ig coated beads. F, NRP-1 expression on human Tconv or Treg cells sorted from umbilical cord blood and culture with anti-CD3, anti-CD28, and IL-2 for the indicated times. G, Transwell suppression assay in which 8-day-expanded human Treg were cultured with either IgG or hSema4a-Ig coated beads, or with fixed autologous human Teff in the presence or absence of blocking antibodies to NRP1. H, ELISA-based binding assay in which plates coated with recombinant mNrp1 were incubated with Sema4a-Ig or mouse IgG1, in the presence of isotype controls, anti-Nrp1, or anti-Sema4a. Sema4a-Ig or mouse IgG1 was detected using an anti-isotype antibody. I, Transwell suppression assay in which Tconv:Treg cocultures were stimulated in the presence of an neutralizing anti-Nrp1 antibody or its isotype control. Results represent the mean of three [A, D-F, H, I] or five [B, C, G] experiments. *, p<0.05, , p<0.01, *, p<0.001 by unpaired t-test.
Figure 2:
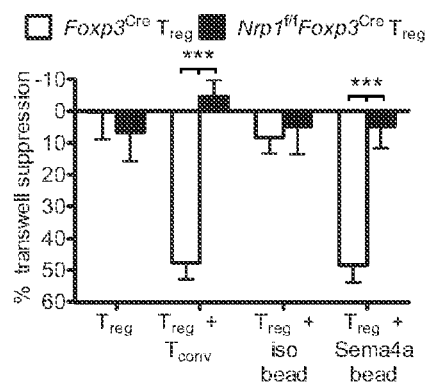
Figure 2:
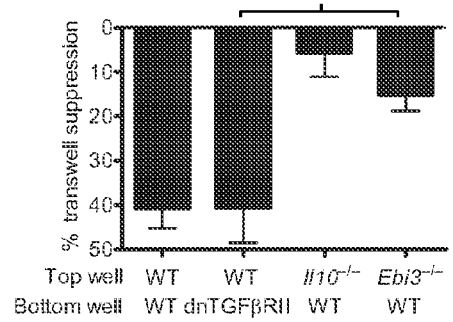
Figure 2:
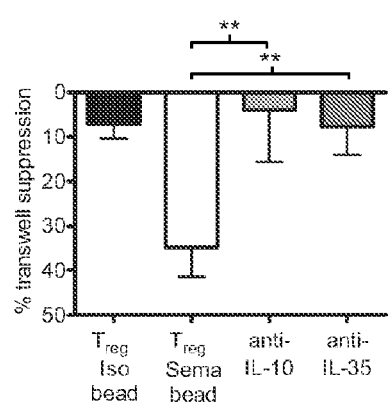
Figure 2:
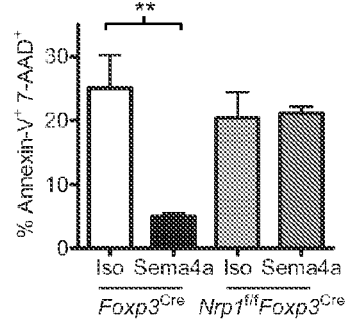
Figure 2:
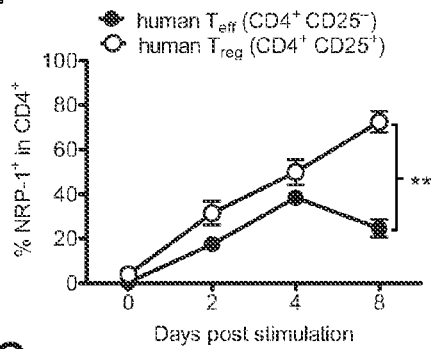
Figure 2:
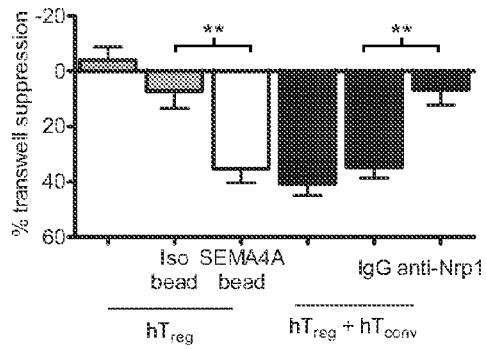
Figure 2:
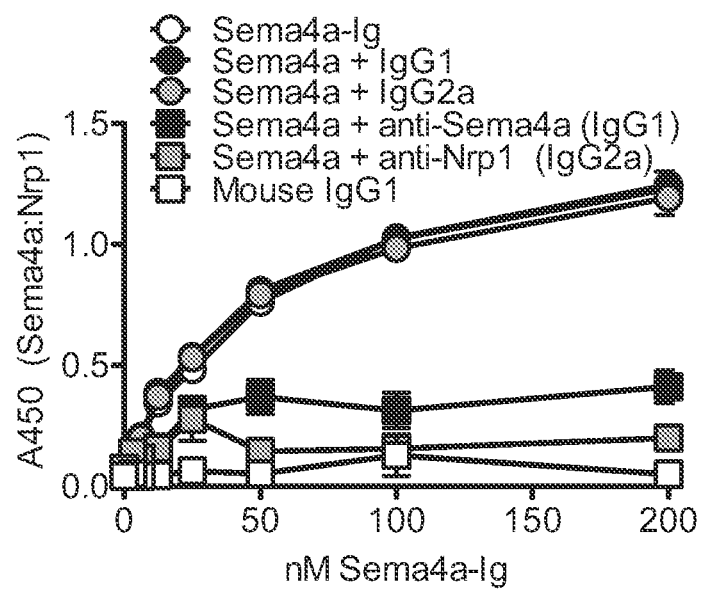
Figure 2:
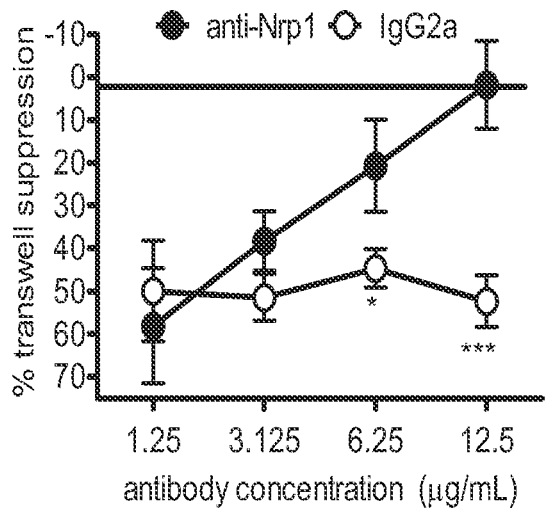

The present inventors postulated that Nrp1 may be the receptor for Sema4a that mediates Treg functional potentiation. First, an Nrp1-specific mAb could block Treg boosting in vitro (FIG. 2A). Direct interaction between Sema4a and Nrp1 was verified in an ELISA assay with purified, recombinant Nrp1 and Sema4a (FIG. 2H). Importantly, dose-dependent inhibition was observed with Nrp1 and Sema4a mAbs that disrupt Nrp1:Sema, but not Nrp1:VEGF, interaction (FIG. 2H). Second, Nrp1-deficient Tregs, generated by crossing Nrp1$^{f/f}$ and Foxp3$^{Cre}$ mice (herein referred to as Nrp1$^{f/f}$Foxp3$^{Cre}$)[17,23], lacked cell surface Nrp1 expression and failed to mediate Transwell suppression following co-culture with Tconv cells or Sema4a-Ig-coated beads (FIG. 2B). However, Nrp1-deficient Tregs retained the capacity to mediate contact-dependent suppression (as determined by classical suppression assay in which wild-type or neuropilin-deficient Tregs were cocultured different concentrations in the presence of anti-CD3/anti-CD28 coated beads). Importantly, direct interaction between Sema4a and Nrp1 was verified by flow cytometric staining of Foxp3$^{Cre}$, but not Nrp1$^{f/f}$Foxp3$^{Cre}$, Tregs with fluorochrome-labeled Sema4a-Ig and in an ELISA assay with purified, recombinant Nrp1 and Sema4a, which appeared equivalent to its known ligand Sema3a. While these data clearly demonstrate that Sema4a can bind to Nrp1 and boost Treg function, it is possible that other semaphorin family members could also serve this function. Second, an Nrp1-specific mAb blocked Treg Transwell suppression in vitro (FIG. 2I).

The present inventors and co-workers have previously shown that Tregs mediate Transwell suppression via IL-10 and IL-35 but not TGFβ[12]. Herein, two experimental approaches were used to determine if the mechanisms used by Tconv cell- and Sema4a-boosted Tregs to suppress were synonymous. First, Tregs stimulated in the presence of Sema4a-Ig-coated beads in the top chamber of a Transwell plate were equally capable of suppressing wild-type (WT) and dnTGFβRII Tconv cells, which are insensitive to TGFβ[24], in the bottom chamber suggesting that TGFβ is not required (FIG. 2C). In contrast, Il10$^{-/-}$ and Ebi3$^{-/-}$ Tregs, which are unable to secrete IL-10 and IL-35 respectively, were unable to suppress WT Tconv across a Transwell (FIG. 2C). Second, IL-10 and IL-35 neutralizing mAbs prevented Transwell suppression mediated by WT Tregs (FIG. 2D). Although Sema4a:Nrp1 ligation appeared to enhance Treg function, the inventors reasoned that it might also enhance Treg survival and/or stability in vitro. Indeed, Sema4a stimulation reduced the amount of cell death as determined by Annexin V and 7-AAD staining in an Nrp1-dependent manner (FIG. 2E). Subsequent qPCR analysis of wild-type and Nrp1-deficient Tregs cultured in the presence of isotype or Sema4a-Ig for 72 h with anti-CD3, anti-CD28, and IL-2 and intracellular cytokine staining for IL-10 of cells stimulated in the presence of isotype or Sema4a-Ig for 72 h with anti-CD3, anti-CD28, and IL-2 (Brefeldin A added for the last 8 hours of stimulation) revealed that IL-10 mRNA levels were not increased by Sema4a-Nrp1 ligation and the percentage of IL-10+ Tregs by ICS was not increased. Nevertheless, as determined by IL-10 ELISA and IL-35 IP/IB from supernatants of cells, both IL-10 and IL-35 were elevated in cultures when wild type but not Nrp1-deficient Tregs were stimulated with anti-CD3, anti-CD28 and Sema4a-Ig. Taken together, these data suggest that Nrp1 ligation by Sema4a potentiates IL-10/IL-35-dependent suppression and enhanced Treg survival and longevity in vitro.

Although it has been suggested that NRP1 is not expressed on human Tregs[25], this has not been rigorously assessed on activated or functionally suppressive Tregs. As human Tregs can require activation in order to gain maximal suppressive function[12,26], the present inventors reasoned that NRP1 may only be expressed on functionally suppressive Tregs. Consistent with previous studies[25], resting umbilical cord blood Tregs and Tconv cells did not express NRP1 (FIG. 2F). Although activation with anti-CD3, anti-CD28 and IL-2 induced early NRP1 expression by both T cell populations, Tregs exhibited long-term stable expression of NRP1. It was then assessed whether an NRP1-SEMA4A axis could potentiate human Treg function. As previously shown[26], Tconv can potentiate human Treg suppression across a permeable Transwell membrane (FIG. 2G). Importantly, this suppressive activity was blocked by anti-NRP1 mAbs, while immobilized human SEMA4A was sufficient to potentiate human Treg function in the absence of Tconv (FIG. 2G). These data support the possibility that the same pathway is active in murine and human Tregs.

Nrp1-Deficient Tregs Maintain Immune Homeostasis

Given that disruption of the Nrp1:Sema4a axis diminishes Treg activity in vitro, the present inventors posited that Treg function might be compromised in vivo, particularly at highly inflammatory sites. Foxp3-deficient mice develop a strong autoimmune condition, reminiscent of the human disease IPEX. This is characterized my massive immune infiltration and tissue inflammation which is lethal by 3-6 weeks[2,27]. Thus disruption of Treg function in vivo could lead to the development of an inflammatory disease. Nrp1$^{f/f}$Foxp3$^{Cre}$ mice and their age- and sex-matched littermate Foxp3$^{Cre}$ controls were observed for 10 months and a detailed histological analysis of all organs typically targeted in Treg-deficient mice was performed. Blinded analysis demonstrated that Nrp1$^{f/f}$Foxp3$^{Cre}$ mice were within normal limits in all respects including outward appearance, and histological analysis of skin, lung, liver, intestines, pancreas, kidney, salivary glands and spleen. No alterations in the size, percentage or phenotype of T cell subpopulations, as determined by flow cytometric analysis, were observed. Thus, no alteration in immune homeostasis, development of inflammatory disease or autoimmunity could be detected in aged mice with a restricted deletion of Nrp1 on Tregs.

Figure 3:
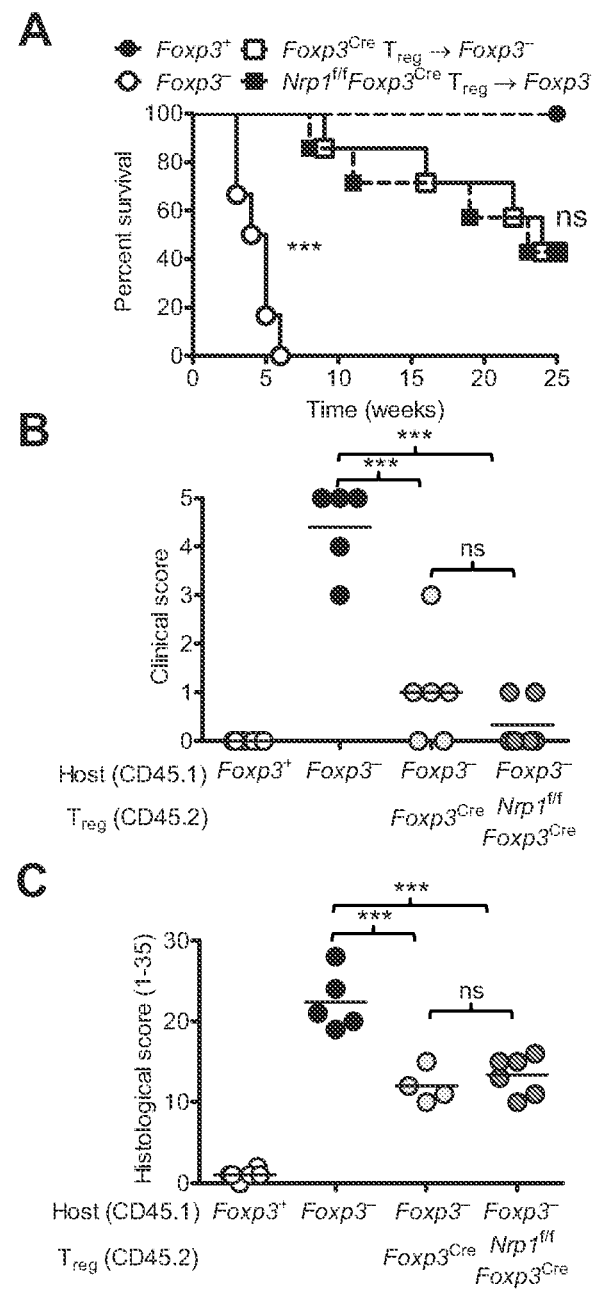
FIGS. 3A-C demonstrate that Nrp1-deficient Tregs prevent the autoimmune disease of Foxp3-deficient animals. A, Survival curve of Foxp3− male mice that received no injection or 1×10⁶ Foxp3$^{Cre}$ or Nrp1$^{f/f}$Foxp3$^{Cre}$ Treg at 1-2 days of age. B, Clinical scores at 5 weeks of mice treated as in A. C, Histological scores of liver, lung, and ear pinna (combined) from mice treated as in a. Results represent three independent experiments. , p<0.01 by one-way ANOVA [A], , p<0.001 by unpaired t-test [B-C], ns, not significant, p>0.05.

The autoimmune phenotype of Foxp3-deficient mice can be substantially delayed by the adoptive transfer of Tregs into 2 day old mice, which can persist for several months before the mice succumb to the disease[2,27]. Disease onset, prevalence, clinical and histological scores (of liver, lung, and ear pinna) were all identical between Foxp3$^{Cre}$ and Nrp1$^{f/f}$Foxp3$^{Cre}$ Treg recipients (FIG. 3). Collectively, these data indicate that expression of Nrp1 on Tregs is dispensable for the maintenance of immune homeostasis and the prevention of inflammatory and autoimmune disease that would normally develop in the absence of Tregs.

Nrp1-Deficient Tregs Fail in Inflammatory Environments

Tregs represent a major barrier to effective anti-tumor immunity in many cancers[28,29]. Treg depletion, via anti-CD25 treatment or use of Foxp3$^{DTR-gfp}$ mice (in which Foxp3$^+$ Treg express the diphtheria toxin receptor, allowing for their conditional depletion by DT administration), has been shown to greatly enhance anti-tumor immunity[30,31]. However, depletion of Tregs also results in massive lymphoproliferation and autoimmune disease similar to that seen in Foxp3-deficient mice[32]. As tumors represent a highly inflammatory environment, the capacity of Nrp1-deficient Tregs to mediate tumor-induced tolerance and prevent effective anti-tumor immunity was assessed. Three transplantable tumor models were used: MC38 (an immunogenic colon carcinoma line), EL4 (a moderately immunogenic thymoma), and B16 (a poorly immunogenic melanoma)[33,34]. Although complete Treg loss by DT treatment of tumor-inoculated Foxp3$^{DTR-gfp}$ mice resulted in tumor clearance, mice succumb to autoimmune-mediated lethality around three weeks post-DT treatment (FIG. 4A-C).

Tumor growth in Nrp1$^{f/f}$Foxp3$^{Cre}$ mice and their Foxp3$^{Cre}$ littermate controls was then assessed. Significantly delayed MC38 tumor growth was observed in Nrp1$^{f/f}$Foxp3$^{Cre}$ mice, despite the absence of any complete remission (CR) (FIG. 4A). In contrast, CR was observed in ~40% of EL4-inoculated Nrp1$^{f/f}$Foxp3$^{Cre}$ mice with greatly reduced tumor growth in almost all mice (FIG. 4B). Strikingly, CR was observed in two-thirds of the B16-inoculated Nrp1$^{f/f}$Foxp3$^{Cre}$ mice, with reduced tumor growth in the remaining mice (FIG. 4C). Using a lung metastatic B16 model, Foxp3$^{Cre}$ animals developed a dose-dependent increase in the number of metastases while Nrp1$^{f/f}$Foxp3$^{Cre}$ mice exhibited almost complete clearance, even at high tumor doses (FIG. 4D). Analysis of B16 tumor-infiltrating lymphocytes (TILs) in the skin showed that while both Treg populations can infiltrate tumors, Nrp1-deficient Tregs have a limited ability to suppress effector CD8$^+$ T cell proliferation and cytokine production, particularly in the highly tumoricidal IFNγ$^+$TNFα$^+$IL-2$^+$ subset (FIG. 4E)[35]. Thus, the program driven by Nrp1 signaling in Tregs is critically important for suppressing anti-tumor immunity.

The present inventors also sought to determine what cells expressed Sema4a in the tumor microenvironment. Surprisingly, conventional DCs (cDCs), CD8$^+$ T$_{conv}$ cells, NK cells, and to a lesser degree CD4$^+$ T$_{conv}$ cells downregulate Sema4a surface expression in the TIL compared to the draining and nondraining lymph nodes (FIG. 4H). Instead, the majority of Sema4a$^{hi}$ tumor-infiltrating cells (~57%) were PDCA1$^+$B220$^+$CD11c$^+$ plasmacytoid dendritic cells (pDCs) (FIG. 4H). While surprising, this finding was consistent with previous literature suggesting that pDCs can be tolerogenic, and that depletion of pDCs resulted in increased antitumor immunity (Demoulin et al., J Leukoc Biol 93, 343-352 (2013); Faget et al., Cancer Res 72, 6130-6141 (2012); Sawant et al., J Immunol 189, 4258-4265, (2012)). Indeed, in Transwell suppression assays using Treg cocultured with pDCs sorted from spleen and lymph node preparations, activated overnight with CpG oligonucleotides, and fixed briefly in 1% PFA followed by extensive washing, pDCs could potentiate T$_{reg}$ function in Transwell suppression assays in a Sema4a-dependent manner.

Previous studies have shown the Nrp1 domains that bind semaphorins are district from those that bind VEGF[40]. In order to provide further support for a Sema4a-Nrp1 axis mediating T$_{reg}$-induced tumor tolerance, the present inventors utilized Sema4a and Nrp1-specific mAbs that disrupt Nrp1-Sema4a but not Nrp1-VEGF interaction. Specifically, ELISA-based binding assays were performed using plates coated with 500 ng/mL recombinant mNrp1 incubated with either (i) anti-Nrp1 or mouse IgG1 in the presence of 50 ng/mL VEGF165 (detected using anti-VEGF biotin) or (ii) Sema4a-Ig or mouse IgG1, in the presence of isotype controls, anti-Nrp1, or anti-Sema4a (Sema4a-Ig or mouse IgG1 were detected using an anti-isotype antibody). Wild-type C57/BL6 mice inoculated with B16 melanoma and given twice-weekly injections of Nrp1 or Sema4a blocking mAbs (100 µg; R&D Systems, clone 757129) exhibited significantly reduced tumor growth compared to those given isotype control (FIG. 4I). Importantly, the effect of the Nrp1 and Sema4a blocking mAbs was essentially identical. Furthermore, utilization of Sema4a-Ig as a soluble antagonist in vivo also resulted in significantly reduced tumor growth (FIG. 4J), associated with similar increases in CD8+ T cell tumor infiltration. To determine whether Nrp1 blockade could have therapeutic utility, B16 tumor-bearing C57/BL6 mice were treated with higher doses (400 µg initial dose, 200 µg twice weekly) of Nrp1 blocking mAb. Remarkably, tumor growth was reduced with this single modality treatment, with CR in some mice (FIG. 4F).

Nrp1-dependent Treg function could also be broadly important in suppressing responses in other established, highly inflammatory environments. Adoptive transfer of naïve CD4+CD45RB$^{hi}$ Tconv cells into Rag1$^{-/-}$ mice induces highly inflammatory colitis, similar to human inflammatory bowel disease (IBD), that can be rescued by subsequent transfer of purified Tregs[13,36]. Indeed, injection of Tconv cells into Rag1$^{-/-}$ mice resulted in significant weight loss and immune pathology, which could be rescued by Foxp3$^{Cre}$ Treg (FIG. 4G). However, Nrp1-deficient Tregs failed to ameliorate colitis, resulting in significant weight loss and immune pathology. Thus, Nrp1-mediated Treg function is required for curing an established inflammatory disease, such as colitis.

Figure 5:
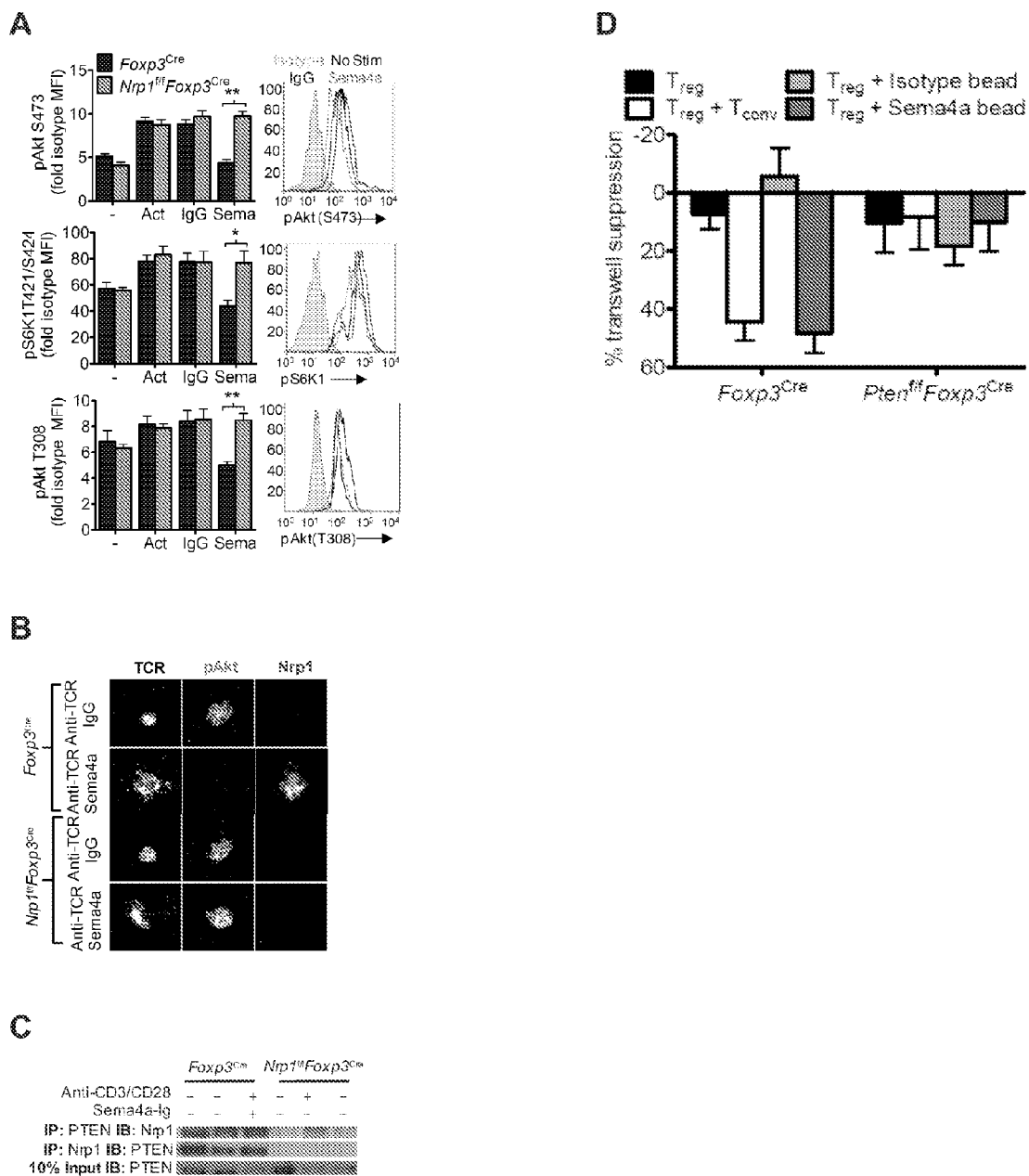
FIGS. 5A-D demonstrate that ligation of Nrp1 by Sema4a promotes Treg stability through the modulation of Akt-mTOR signaling. A, Flow cytometric analysis of Akt signaling in Foxp3$^{Cre}$ or Nrp1$^{f/f}$Foxp3$^{Cre}$ Tregs. Flow cytometrically-purified Tregs were left resting or stimulated with anti-CD3/anti-CD28 beads overnight in the presence of beads coated with Sema4a-Ig or isotype control. B, TIRF microscopic analysis of Akt activation in immunologic synapses (IS) of Tregs stimulated 20 min on a lipid bilayer coated with anti-TCR antibodies in the presence or absence of Sema4a-Ig. C, Immunoprecipitation analysis of Nrp1 using Tregs expanded with PMA and ionomycin for 3 days, followed by a 5-7 day expansion in 500 U/mL rhIL-2, serum starved for 3 h, then stimulated as indicated for 3 hours prior to IP. D, Transwell suppression assay using Foxp3$^{Cre}$ or Pten$^{f/f}$Foxp3$^{Cre}$ Tregs. Results are the mean of three (A, B, D) or represent at least three experiments (C). *, p<0.05, ** p<0.01 by unpaired t-test.
Figure 6:
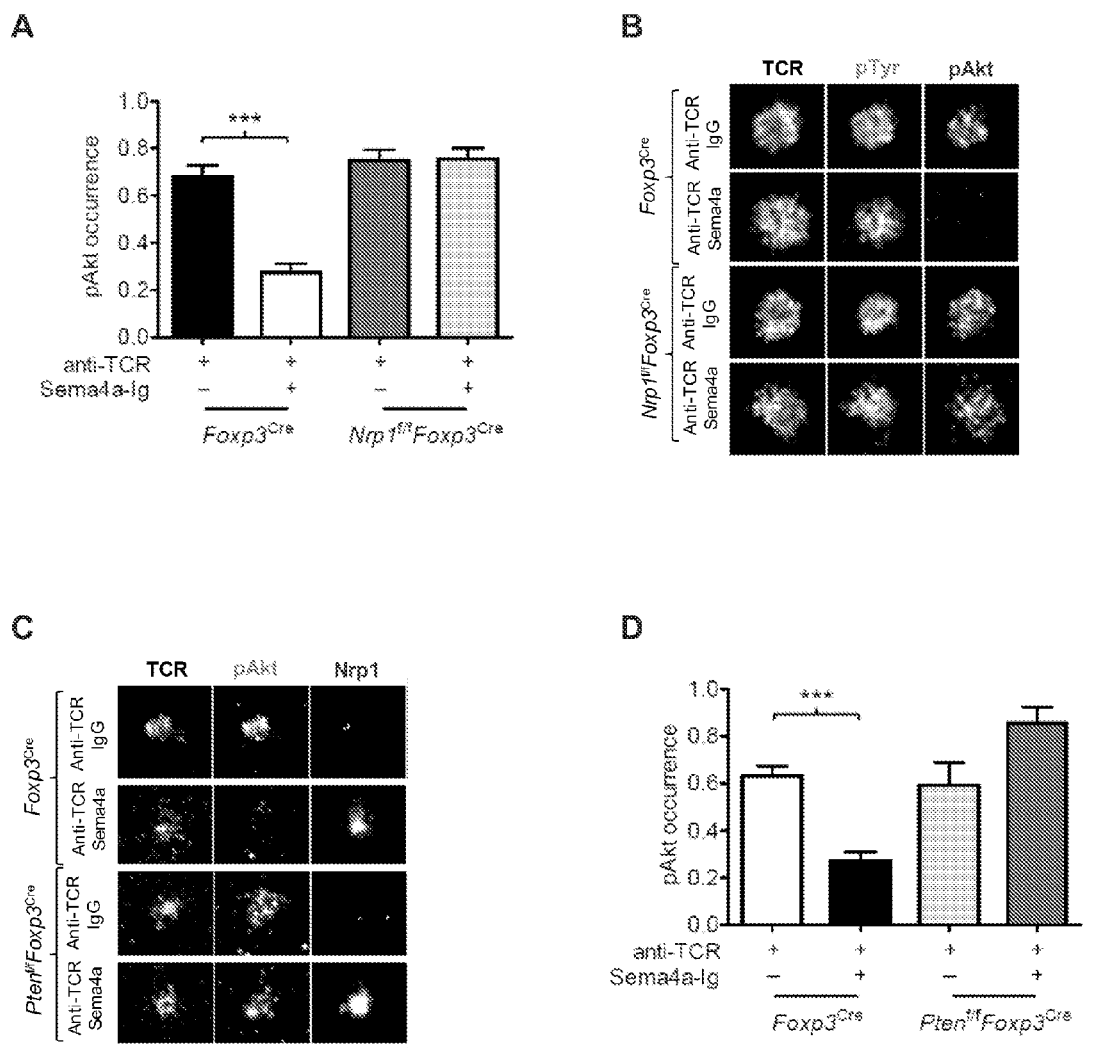
FIGS. 6A-D demonstrate that neuropilin restrains IS Akt activation via PTEN. A, Tabulation of pAkt occurrence in IS from FIG. 5B. B, TIRF microscopy of IS activation of Akt and pTyr in Foxp3$^{Cre}$ or Nrp1$^{f/f}$ Foxp3$^{Cre}$ Treg purified flow cytometrically and then stimulated on a lipid bilayer containing anti-TCR and either IgG or Sema4a-Ig. C, TIRF microscopy of IS recruitment of neuropilin and activation of Akt in Foxp3$^{Cre}$ or Pten$^{f/f}$Foxp3$^{Cre}$ Treg purified flow cytometrically and then stimulated for 20 minutes on a lipid bilayer containing anti-TCR and either IgG or Sema4a-Ig. D, Tabulation of pAkt occurrence in IS from C. Results are representative of three [A-B] or two [C-D] independent experiments. *** p<0.001 by one-way ANOVA.

Nrp1 Ligation Restrains Akt-mTOR Via PTEN to Initiate Foxo-Mediated Treg Stabilization Although signaling downstream of Nrp1 in tumor lines, neurons and endothelium has been studied following ligation by VEGF or class III semaphorins[15,17], the Nrp1 signaling pathway induced by a class IV semaphorins in Tregs has been unknown. Interestingly, Nrp1 has been shown to modulate Akt (protein kinase B) activity in some systems[37,38]. As Akt-mTOR activity has been shown to be detrimental to Treg function[39,40], the present inventors hypothesized that Nrp1 ligation might inhibit Akt activation. Foxp3$^{Cre}$ and Nrp1$^{f/f}$Foxp3$^{Cre}$ Tregs were stimulated in the presence of Sema4a-Ig- or IgG-coated beads and Akt-mTOR activation assessed by flow cytometry. Nrp1 ligation limited phosphorylation of Akt S473 as well as phosphorylation of S6K1 T389 in Tregs, which are required for its activation (FIG. 5A). Akt phosphorylation was also examined at the immunologic synapse (IS) using total internal reflection fluorescent (TIRF) microscopy. Foxp3$^{Cre}$ and Nrp1$^{f/f}$Foxp3$^{Cre}$ Tregs were stimulated with a lipid bilayer containing anti-TCR mAb and either Sema4a-Ig or an IgG isotype control. Robust recruitment of Nrp1 to the IS was observed when Sema4a was present which coincided with an Nrp1-dependent loss of Akt activity despite equivalent global phosphotyrosine staining at the IS (FIGS. 5B and 6A-B).

To determine whether Akt inactivation was sufficient for Treg potentiation, Tregs were transduced with retrovirus encoding either wild-type (WT) or dominant negative kinase-dead (DN) Akt. Tregs transduced with DN, but not WT, Akt could mediate Transwell suppression to an extent comparable to that induced by Sema4a-Ig, suggesting that repressed Akt-mTOR activity downstream of Nrp1 is the dominant pathway driving Treg potentiation.

Nrp1 has a small cytoplasmic domain with a C-terminal PDZ domain-binding motif (amino acid sequence: SEA) (Pellet-Many et al., Biochem J 411, 211-226 (2008)). The present inventors hypothesized that this domain is required for Sema4a-dependent loss of pAkt at the IS. Neuropilin-deficient Tregs were transduced with retrovirus encoding WT Nrp1 or a PDZ domain binding motif-deficient Nrp1 mutant. Interestingly, loss of the PDZ domain binding motif completely abrogated the ability of Nrp1 to inhibit Akt activation at the IS following Sema4a ligation (Fig.), suggesting that this motif is recruiting a molecular inhibitor of Akt signaling.

Phosphatase and tensin homolog (PTEN) has been shown to inhibit Akt activation[41]. While PTEN appears to be dispensable for contact-dependent Treg suppression[42], the present inventors hypothesized that PTEN may contribute to Nrp1-mediated inactivation of Akt. Low level, constitutive PTEN association with Nrp1 was observed in resting and activated Tregs, which was substantially enhanced by Sema4a ligation (FIG. 5C). In addition, PTEN-deficient Treg were unable to mediate Tconv and Sema4a-Ig induced Transwell suppression (FIG. 5D). Lastly, PTEN-deficient Tregs failed to inhibit Akt activation at the IS despite robust Nrp1 recruitment by Sema4a (as determined by TIRF microscopy of IS recruitment of neuropilin and activation of Akt in Foxp3$^{Cre}$ or Pten$^{f/f}$Foxp3$^{Cre}$ Treg purified flow cytometrically and then stimulated for 20 minutes on a lipid bilayer containing anti-TCR and either IgG or Sema4a-Ig; see FIG. 6C-D). These data suggest that PTEN is required for Nrp1-mediated repression of Akt activation at the IS and Treg functional potentiation.

Akt activity can hamper the Treg suppressive program in part by regulating the nuclear localization of Foxo transcription factor family members, as Akt-mediated phosphorylation promotes their nuclear exclusion via 14-3-3 binding[43-45]. Foxos play a key role in controlling Treg development and function by regulating Foxp3 expression, promoting a cohort of Treg-associated genes and limiting the expression of T cell-lineage specific transcription factors and effector molecules. As expected, unstimulated Treg show nuclear Foxo staining, while activated Treg exclude Foxo from the nucleus. In contrast, inclusion of Sema4a-Ig inhibited Foxo nuclear exclusion.

To determine the transcriptional program that promotes Nrp1-mediated Treg potentiation, gene expression profiling was conducted on Foxp3$^{Cre}$ and Nrp1$^{f/f}$Foxp3$^{Cre}$ Tregs stimulated in the presence of Sema4a-Ig- or IgG1-coated beads in vitro. Specifically, Foxp3$^{Cre}$ and Nrp1$^{f/f}$Foxp3$^{Cre}$ CD45Rb$^{lo}$ Foxp3 (YFP)+ CD4+ T cells were stimulated for 48 hours with anti-CD3, anti-CD28, 100 U/mL rhIL-2, and immobilized IgG1 or Sema4a-Ig. RNA extracted from these cells was subjected to Affymetrix gene profiling analysis. Microarray data was then subjected to Gene Set Enrichment Analysis (GSEA) analysis using MSigDB providing enrichment score (ES), normalized enrichment score (NES) and False Discovery Rate (FDR) for given gene sets. Also, Gene Ontology DAVID analysis was performed for genes affected by Sema4a in Foxp3$^{Cre}$ Treg but not Nrp1$^{f/f}$Foxp3$^{Cre}$ Treg.

In general, the transcriptional changes associated with Nrp1 ligation in Tregs are consistent with enhanced phenotypic stability. Gene Set Enrichment Analysis (GSEA) and DAVID Gene Ontology analysis revealed several pathways upregulated by Sema4a ligation, including T cell homeostasis and IL-7 signaling, IL-2 downregulated genes, CD28 reactive genes, genes related to T cell differentiation, and several gene sets associated with disease phenotypes (Tables 1 and 3). Statistical analysis of the most upregulated genes revealed those associated with homeostasis, especially the Foxo target Klf2[46], as well as several transcription factors, cell surface molecules, and the anti-apoptotic Bcl2 (Table 3).

In addition, by comparing gene expression profiles from freshly isolated $T_{conv}$ and $T_{regs}$ from Foxp3$^{Cre}$ mice, an internally-controlled $T_{reg}$ signature was obtained which was consistent with those previously reported[5]. Several $T_{reg}$ signature genes were upregulated, including Helios (Ikzf2), Gpr83, Nt5e and Socs2. A subset was confirmed by qPCR (Ikzf2, Socs2, Bcl2, Nt5e, Klf2, Gpr83) and flow cytometry (KLF2, Helios, Bcl2, CD62L, CD127, CD73).

Interestingly, Nrp1 signaling induces the downregulation of several T cell lineage-specific transcription factors (Irf4, Rorg, Eomes) and their targets (Il4, Il5, Il17a) (Table 3). In addition, some regulators of cell signaling (Nedd4, Rgs16, Serpine2) and the checkpoint inhibitor Lag3 were also downregulated. The downregulation of Irf4, Irf8, Rorc, and Rgs16 was confirmed by qPCR. Overall, the transcriptional profile induced by Nrp1 signaling may promote Treg stability, quiescence and survival, while inhibiting programs that would drive or promote Treg terminal differentiation. It is also notable that there appears to be considerable overlap between the transcriptional program mediated by Nrp1 and the Foxos[45].

Foxo proteins can promote the transcription of several genes, which were also upregulated by Sema4a stimulation (Table 3)[45,47]. A gene of particular interest is Klf2, which was upregulated in response to Nrp1 and promotes expression of genes associated with T cell survival, longevity and memory, such as CD62L (Sell) and CD127/IL-7Rα (Il7rα)[47]. Indeed, Treg stimulation in the presence of Sema4a limited their activation-induced downregulation suggesting that the Foxo/KLF2 axis is active in Treg stimulated via Nrp1.

Nrp1 signaling also induces the downregulation of several gene subsets defined by GSEA, including IRF4 targets, cytokine transcripts (Il4, Il5, Il17a), Foxp3 downregulated genes, and IL-2 upregulated genes, among others (Table 2). Target genes validated by qPCR or protein analysis include several T cell lineage-specific transcription factors (Irf4, Rorc, Eomes), regulators of cell signaling (Rgs16) and the inhibitory receptor Lag3. Overall, the transcriptional profile induced by Nrp1 signaling may promote $T_{reg}$ stability, quiescence and survival, while inhibiting programs that would drive or promote $T_{reg}$ terminal differentiation and apoptosis.

Figure 7:
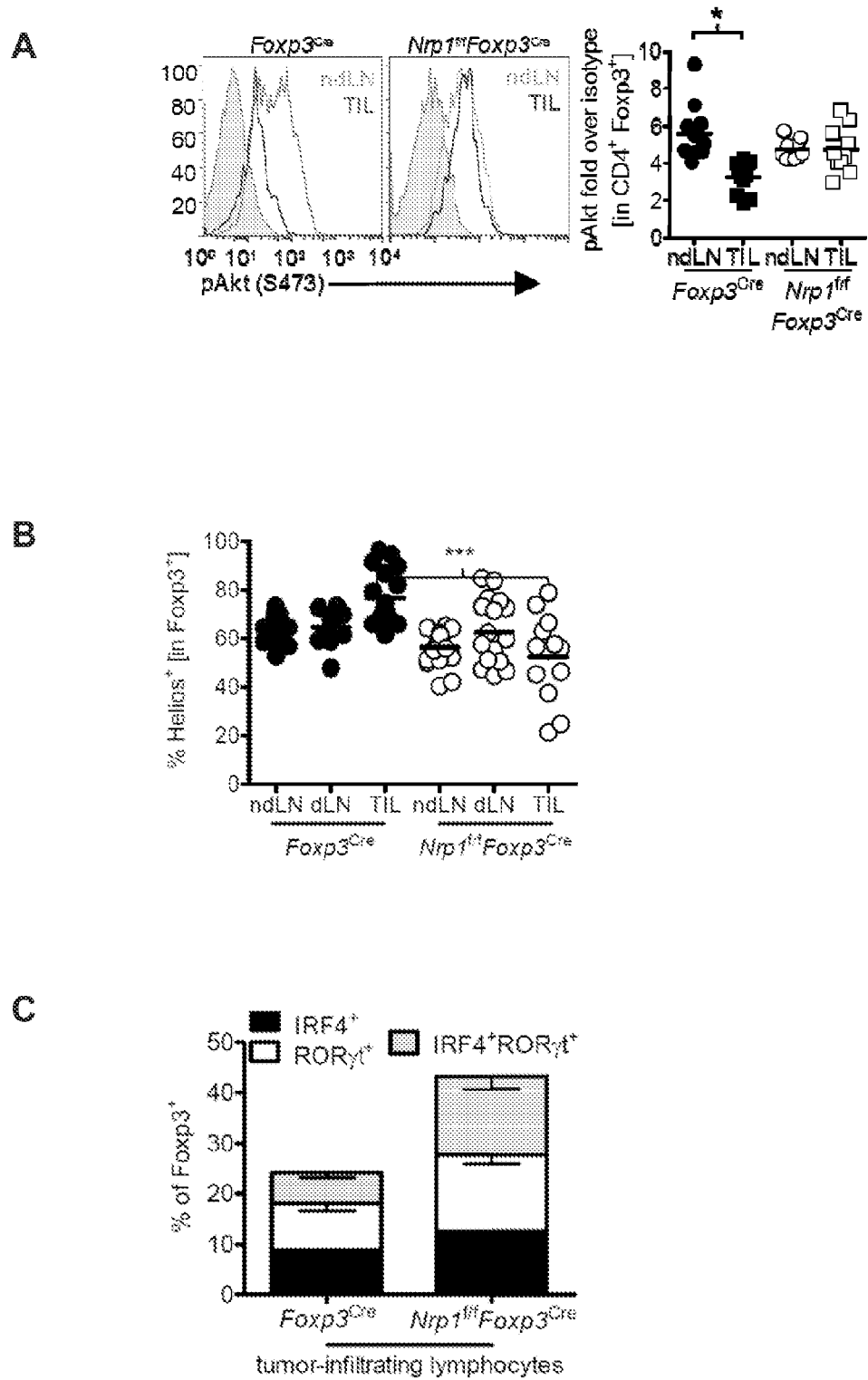
FIGS. 7A-I demonstrate that tumor-infiltrating Treg bear a signature similar to Sema4a:Nrp1 ligation. A, Akt activation of tumor-infiltrating Treg. Tumor bearing Foxp3$^{Cre}$ or Nrp1f/fFoxp3Cre mice were sacrificed on day 12 and ndLN and TIL were harvested. After gradient centrifugation cells were immediately fixed and stained for Akt activation. Shaded histogram indicates isotype control. Results are tabulated beneath normalized to isotype control staining Helios (B), IRF4/RORγt (C), Ki67/BrdU (D), cleaved caspase-3 (E) Bcl2 (F) IL-10 (G) CD73 (H) and LAG-3 (I) staining from ndLN, dLN, or TIL from tumor-bearing Foxp3Cre or Nrp1f/fFoxp3Cre mice. For Ki67/BrdU analysis, animals were injected with BrdU 14 h prior to harvest. For IL-10 staining, cells were restimulated with PMA and ionomycin for 16 h in the presence of a protein transport inhibitor. Results represent the mean of three independent experiments. * p<0.05,  p<0.01, * p<0.001 by paired t-test [A, n=7] or unpaired t-test [B-I, n=8-25].
Figure 7:
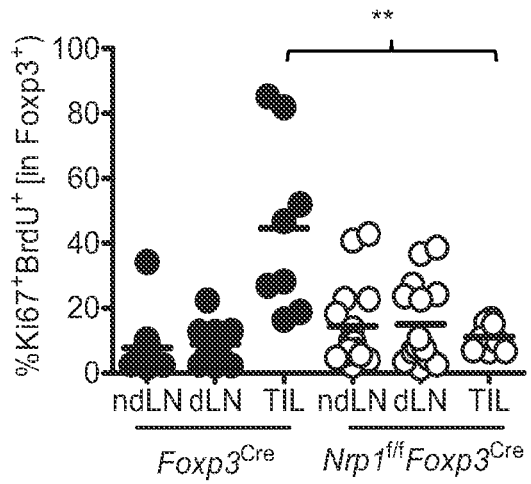
Figure 7:
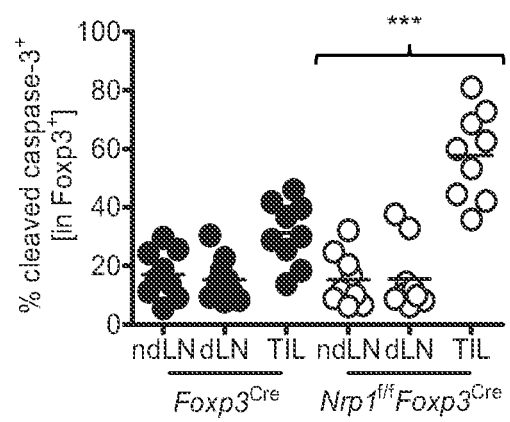
Figure 7:
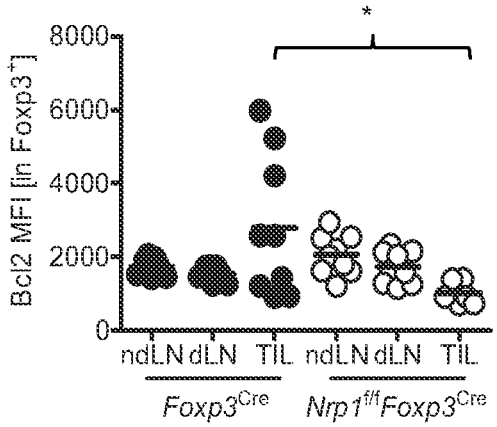
Figure 7:
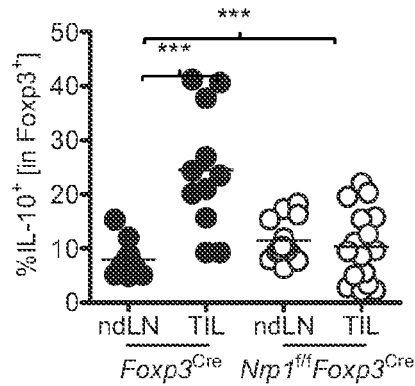
Figure 7:
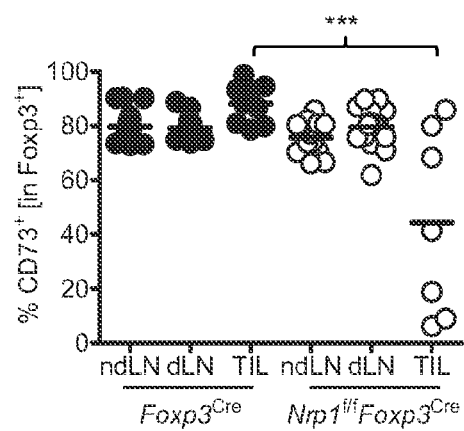
Figure 7:
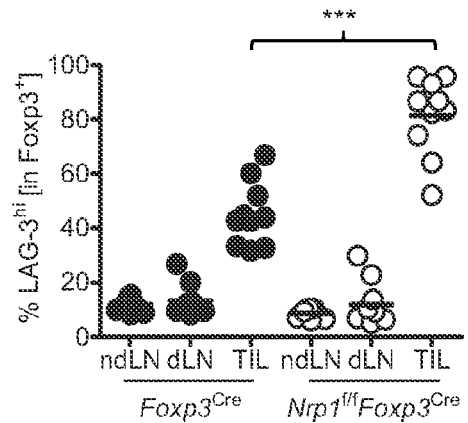

In order to determine if the signaling and transcriptional events observed in vitro were physiologically relevant, key observations were assessed in tumor-infiltrating Tregs. However, it should be noted that only a subset of Nrp1$^{f/f}$Foxp3$^{Cre}$ mice develop tumors following B16 injection and thus the tumors sampled would represent those where the consequence of Nrp1 loss on Tregs was less substantive. First, non-draining lymph nodes and TIL were harvested from tumor-bearing Foxp3$^{Cre}$ and Nrp1$^{f/f}$Foxp3$^{Cre}$ mice and assayed for Akt activation ex vivo. Whereas non-draining LN showed relatively high Akt activation in Treg, tumor-infiltrating Foxp3$^{Cre}$ Treg displayed lower Akt activation (FIG. 7A). Importantly, the modulation of Akt activity in the tumor microenvironment was lost in Nrp1$^{f/f}$Foxp3$^{Cre}$ Tregs supporting Nrp1-driven modulation of Tregs in vivo. Second, protein targets of Nrp1 signaling in TIL were examined, compared to other lymphoid compartments, and found that Helios was upregulated intratumor Tregs, while IRF4 and RORγt were downregulated in vivo in an Nrp1-dependent manner (FIG. 7B-C). Thirdly, this Nrp1-driven program resulted in increased intra-tumoral Treg proliferation and reduced apoptosis, as assessed by Ki67 expression and BrdU incorporation (FIG. 7E), and enhanced cleaved caspase 3 staining (FIG. 7D-E). The enhanced Nrp1-dependent $T_{reg}$ survival observed correlated with enhanced expression of the anti-apoptotic factor Bcl2 (FIG. 7F). Finally, the impact of these changes on intratumoral $T_{reg}$ suppressive mechanisms was examined. Although mRNA levels of IL-10 were not altered, there was an Nrp1-dependent enhancement of intratumoral IL-10$^+$ $T_{regs}$ (FIG. 7G). Furthermore, there was also an Nrp1-dependent maintenance of the extracellular adenosine producing molecule CD73 and the checkpoint inhibitor LAG-3 (FIG. 7H). Thus, Nrp1 signaling provides a critical switch that enforces Treg stability in inflammatory environments.

DISCUSSION

Figure 8:
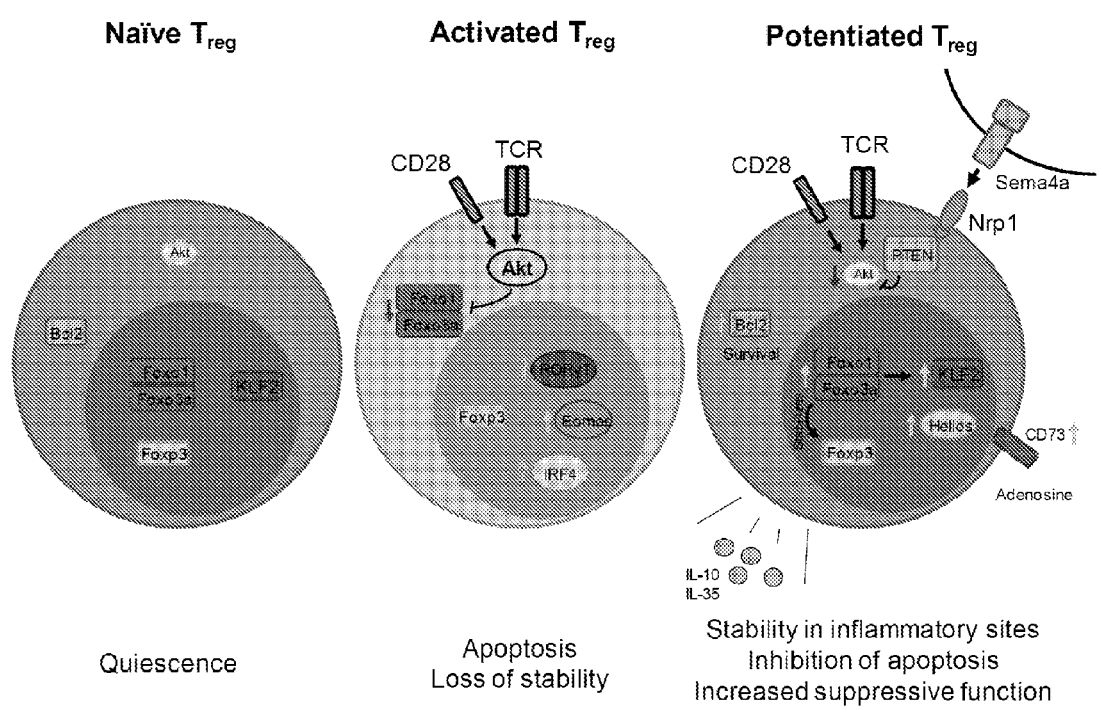
FIG. 8 shows schematically how neuropilin maintains Treg stability. Naïve Treg maintain low Akt activation, which promotes their quiescence through the activity of factors like Foxos and KLF2 (left). Upon activation, Tregs stimulated in the absence of Sema4a:Nrp1 have high activation of Akt, which promotes the nuclear exclusion of Foxos, leading to loss of Treg stability (center). Nrp1 ligation via Sema4a restrains Akt activation via recruitment of PTEN, inhibiting the nuclear exclusion of Foxos (right). This promotes a genetic program associated with stability and increased Treg function.

The data provided herein demonstrate that cell contact-dependent potentiation of Treg function is mediated via Sema4a-mediated Nrp1 ligation via a PTEN:Akt:Foxo axis (FIG. 8). Notably, Nrp1 appears to be one of a limited number of cell surface receptors (e.g., PD-1[48] and CTLA-4[49]) that has been suggested to limit Akt activity in T cells. While Nrp1 under certain circumstances can modulate or even activate Akt signaling (Banerjee et al., Biochemistry 47, 3345-3351 (2008); Cao et al., Cancer Res 68, 8667-8672 (2008); Fukasawa et al., Cancer Biol Ther 6, 1173-1180 (2007); Kim et al., J Immunol 177, 5727-5735 (2006)), the specific context in which Nrp1 functions in $T_{regs}$ (e.g., recruitment to the IS, unique cell type, transmembrane vs soluble ligand) may provide a distinct environment that facilitates PTEN recruitment and loss of Akt activity. This pathway enhances Treg function indirectly by enforcing stability and promoting survival, which is most evident in inflammatory sites such as in tumors and colitic intestinal mucosa. The issue of Treg stability/plasticity has been highly contentious, and the cell-extrinsic stimuli and mechanisms which maintain Treg stability remain elusive[8-11]. Given that Foxo family members enhance Foxp3 function and promote Treg homeostasis and function[45], it is noteworthy that Nrp1 signaling counteracts the negative impact of Akt on Foxo nuclear localization. Indeed, there is substantial overlap between the transcriptional profiles induced by Foxo and Nrp1 signaling[45]. It is also interesting that Nrp1 signaling modulates the expression of several KLFs (Klf2, Klf1), which are known to be involved in cell quiescence[46]. A transcription factor quintet has also recently been shown to 'lock-in' the Treg transcriptional signature[4]. Interestingly, some of these transcription factors are modulated by Nrp1 signaling (e.g., Ikzf2, Irf4, Gata1), suggesting that Sema4a-mediated Nrp1 ligation may constitute a cell-extrinsic regulator of this program. Collectively, the observations provided herein suggest that the Sema4a:Nrp1 axis is required to maintain Treg stability at inflammatory sites. Furthermore, it is possible that the Nrp1:Sema4a pathway may be perturbed under certain pathological or genetic circumstances which could also provide a basis for the seemingly contradictory perceptions of Treg stability versus plasticity in a variety of normal and diseased states. Given that memory CD4$^+$ and CD8$^+$ T cells have been shown to express Nrp1, it is possible that restrained Akt-mTOR activation may facilitate maintenance of the memory T cell phenotype (Powell et al., Annu Rev Immunol 30, 39-68 (2012)).

As Tregs represent a major barrier to effective anti-tumor immunity in many cancers[28,29], a prevailing question of clinical importance is whether it is possible to limit Treg function in tumors while preventing inflammatory or auto-immune adverse events. It is also intriguing that a dominant source of Sema4a in the tumor studies described herein was the plasmacytoid DC. The present identification of the Nrp1:Sema4a axis as a pivotal pathway required for Treg stability at tumoral inflammatory sites but not for peripheral homeostatic maintenance suggests, for the first time, that Sema4a:Nrp1 blockade via antibodies or soluble antagonists might be a viable therapeutic strategy to limit tumor-induced tolerance without evoking autoimmunity.

REFERENCES

1. Vignali, D. A., Collison, L. W. & Workman, C. J. How regulatory T cells work. Nat Rev Immunol 8, 523-532 (2008).
2. Fontenot, J. D., Gavin, M. A. & Rudensky, A. Y. Foxp3 programs the development and function of CD4+CD25+ regulatory T cells. Nat Immunol 4, 330-336 (2003).
3. Hori, S., Nomura, T. & Sakaguchi, S. Control of regulatory T cell development by the transcription factor Foxp3. Science 299, 1057-1061 (2003).
4. Fu, W. et al. A multiply redundant genetic switch 'locks in' the transcriptional signature of regulatory T cells. Nat Immunol (2012).
5. Hill, J. A. et al. Foxp3 transcription-factor-dependent and -independent regulation of the regulatory T cell transcriptional signature. Immunity 27, 786-800 (2007).
6. Belkaid, Y. & Rouse, B. T. Natural regulatory T cells in infectious disease. Nat Immunol 6, 353-360 (2005).
7. Himmel, M. E., Hardenberg, G., Piccirillo, C. A., Steiner, T. S. & Levings, M. K. The role of Tregulatory cells and Toll-like receptors in the pathogenesis of human inflammatory bowel disease. Immunology 125, 145-153 (2008).
8. Zheng, Y. et al. Regulatory T-cell suppressor program co-opts transcription factor IRF4 to control T(H)2 responses. Nature 458, 351-356 (2009).
9. Koch, M. A. et al. The transcription factor T-bet controls regulatory T cell homeostasis and function during type 1 inflammation. Nat Immunol 10, 595-602 (2009).
10. Chaudhry, A. et al. CD4+ regulatory T cells control TH17 responses in a Stat3-dependent manner. Science 326, 986-991 (2009).
11. Zhou, X. et al. Instability of the transcription factor Foxp3 leads to the generation of pathogenic memory T cells in vivo. Nat Immunol 10, 1000-1007 (2009).
12. Collison, L. W., Pillai, M. R., Chaturvedi, V. & Vignali, D. A. Regulatory T cell suppression is potentiated by target T cells in a cell contact, IL-35- and IL-10-dependent manner. J Immunol 182, 6121-6128 (2009).
13. Collison, L. W. et al. The inhibitory cytokine IL-35 contributes to regulatory T-cell function. Nature 450, 566-569 (2007).
14. Nkyimbeng-Takwi, E. & Chapoval, S. P. Biology and function of neuroimmune semaphorins 4A and 4D. Immunol Res 50, 10-21 (2011).
15. Kolodkin, A. L. et al. Neuropilin is a semaphorin III receptor. Cell 90, 753-762 (1997).
16. Kitsukawa, T. et al. Neuropilin-semaphorin III/D-mediated chemorepulsive signals play a crucial role in peripheral nerve projection in mice. Neuron 19, 995-1005 (1997).
17. Gu, C. et al. Neuropilin-1 conveys semaphorin and VEGF signaling during neural and cardiovascular development. Dev Cell 5, 45-57 (2003).
18. Glinka, Y., Stoilova, S., Mohammed, N. & Prud'homme, G. J. Neuropilin-1 exerts co-receptor function for TGF-beta-1 on the membrane of cancer cells and enhances responses to both latent and active TGF-beta. Carcinogenesis 32, 613-621 (2011).
19. Bruder, D. et al. Neuropilin-1: a surface marker of regulatory T cells. Eur J Immunol 34, 623-630 (2004).
20. Weiss, J. M. et al. Neuropilin 1 is expressed on thymus-derived natural regulatory T cells, but not mucosa-generated induced Foxp3+ T reg cells. J Exp Med (2012).
21. Yadav, M. et al. Neuropilin-1 distinguishes natural and inducible regulatory T cells among regulatory T cell subsets in vivo. J Exp Med (2012).
22. Solomon, B. D., Mueller, C., Chae, W. J., Alabanza, L. M. & Bynoe, M. S. Neuropilin-1 attenuates autoreactivity in experimental autoimmune encephalomyelitis. Proc Natl Acad Sci USA 108, 2040-2045 (2011).
23. Rubtsov, Y. P. et al. Regulatory T cell-derived interleukin-10 limits inflammation at environmental interfaces. Immunity 28, 546-558 (2008).
24. Gorelik, L. & Flavell, R. A. Abrogation of TGFbeta signaling in T cells leads to spontaneous T cell differentiation and autoimmune disease. Immunity 12, 171-181 (2000).
25. Milpied, P. et al. Neuropilin-1 is not a marker of human Foxp3+ Treg. Eur J Immunol 39, 1466-1471 (2009).
26. Chaturvedi, V., Collison, L. W., Guy, C. S., Workman, C. J. & Vignali, D. A. Cutting edge: Human regulatory T cells require IL-35 to mediate suppression and infectious tolerance. J Immunol 186, 6661-6666 (2011).
27. Collison, L. W. et al. IL-35-mediated induction of a potent regulatory T cell population. Nat Immunol 11, 1093-1101 (2010).
28. Nishikawa, H. & Sakaguchi, S. Regulatory T cells in tumor immunity. Int J Cancer 127, 759-767 (2010).
29. Wang, H. Y. & Wang, R. F. Regulatory T cells and cancer. Curr Opin Immunol 19, 217-223 (2007).
30. Onizuka, S. et al. Tumor rejection by in vivo administration of anti-CD25 (interleukin-2 receptor alpha) monoclonal antibody. Cancer Res 59, 3128-3133 (1999).
31. Li, X., Kostareli, E., Sufiher, J., Garbi, N. & Hammerling, G. J. Efficient Treg depletion induces Tcell infiltration and rejection of large tumors. Eur J Immunol 40, 3325-3335 (2010).
32. Kim, J. M., Rasmussen, J. P. & Rudensky, A. Y. Regulatory T cells prevent catastrophic autoimmunity throughout the lifespan of mice. Nat Immunol 8, 191-197 (2007).
33. Chen, L. et al. Tumor immunogenicity determines the effect of B7 costimulation on T cell mediated tumor immunity. J Exp Med 179, 523-532 (1994).
34. Lafreniere, R., Borkenhagen, K. & Bryant, L. D. Generation of MC-38 adenocarcinoma tumor specific tumor infiltrating lymphocytes by murine anti-CD3 antibody and recombinant interleukin-2 Mol Biother 3, 26-33 (1991).
35. Wilde, S. et al. Human antitumor CD8+ T cells producing Th1 polycytokines show superior antigen sensitivity and tumor recognition. J Immunol 189, 598-605 (2012).
36. Read, S., Malmstrom, V. & Powrie, F. Cytotoxic T lymphocyte-associated antigen 4 plays an essential role in the function of CD25(+)CD4(+) regulatory cells that control intestinal inflammation. J Exp Med 192, 295-302 (2000).
37. Castro-Rivera, E., Ran, S., Brekken, R. A. & Minna, J. D. Semaphorin 3B inhibits the phosphatidylinositol 3-kinase/Akt pathway through neuropilin-1 in lung and breast cancer cells. Cancer Res 68, 8295-8303 (2008).
38. Gray, M. J. et al. Neuropilin-1 suppresses tumorigenic properties in a human pancreatic adenocarcinoma cell line lacking neuropilin-1 coreceptors. Cancer Res 65, 3664-3670 (2005).

39. Haxhinasto, S., Mathis, D. & Benoist, C. The AKT-mTOR axis regulates de novo differentiation of CD4+ Foxp3+ cells. J Exp Med 205, 565-574 (2008).
40. Crellin, N. K., Garcia, R. V. & Levings, M. K. Altered activation of AKT is required for the suppressive function of human CD4+CD25+ T regulatory cells. Blood 109, 2014-2022 (2007).
41. Stambolic, V. et al. Negative regulation of PKB/Akt-dependent cell survival by the tumor suppressor PTEN. Cell 95, 29-39 (1998).
42. Walsh, P. T. et al. PTEN inhibits IL-2 receptor-mediated expansion of CD4+CD25+ Tregs. J Clin Invest 116, 2521-2531 (2006).
43. Kerdiles, Y. M. et al. Foxo transcription factors control regulatory T cell development and function. Immunity 33, 890-904 (2010).
44. Merkenschlager, M. & von Boehmer, H. PI3 kinase signalling blocks Foxp3 expression by sequestering Foxo factors. J Exp Med 207, 1347-1350 (2010).
45. Ouyang, W. et al. Foxo proteins cooperatively control the differentiation of Foxp3+ regulatory T cells. Nat Immunol 11, 618-627 (2010).
46. McConnell, B. B. & Yang, V. W. Mammalian Kruppel-like factors in health and diseases. Physiol Rev 90, 1337-1381 (2010).
47. Finlay, D. & Cantrell, D. Phosphoinositide 3-kinase and the mammalian target of rapamycin pathways control T cell migration. Ann N Y Acad Sci 1183, 149-157 (2010).
48. Francisco, L. M. et al. PD-L1 regulates the development, maintenance, and function of induced regulatory T cells. J Exp Med 206, 3015-3029 (2009).
49. Parry, R. V. et al. CTLA-4 and PD-1 receptors inhibit T-cell activation by distinct mechanisms. Mol Cell Biol 25, 9543-9553 (2005).
50. Wang, H. et al. Tonic ubiquitylation controls T-cell receptor:CD3 complex expression during T-cell development. EMBO J 29, 1285-1298 (2010).

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

TABLE 1

| NAME | SIZE | ES | NES | NOM p-val | FDR q-val | FWER p-val | RANK AT MAX | LEADING EDGE |
|---|---|---|---|---|---|---|---|---|
| MOSERLE_IFNA_RESPONSE | 20 | 0.780182 | 2.287744 | 0 | 0 | 0 | 3771 | tags = 80%, list = 17%, signal = 97% |
| BASSO_CD40_SIGNALING_DN | 57 | 0.582034 | 2.177623 | 0 | 0.001544 | 0.005 | 4626 | tags = 54%, list = 21%, signal = 69% |
| TAKEDA_TARGETS_OF_NUP98_HOXA9_FUSION_3D_UP | 123 | 0.503057 | 2.161499 | 0 | 0.001646 | 0.008 | 4687 | tags = 45%, list = 21%, signal = 57% |
| ZHAN_V1_LATE_DIFFERENTIATION_GENES_UP | 29 | 0.604006 | 1.993054 | 0 | 0.027944 | 0.163 | 2268 | tags = 34%, list = 10%, signal = 38% |
| BOYLAN_MULTIPLE_MYELOMA_PCA1_UP | 92 | 0.483428 | 1.95568 | 0 | 0.039941 | 0.275 | 2885 | tags = 37%, list = 13%, signal = 42% |
| MORI_PRE_BI_LYMPHOCYTE_DN | 59 | 0.514033 | 1.948411 | 0 | 0.035463 | 0.29 | 5476 | tags = 49%, list = 25%, signal = 65% |
| BENNETT_SYSTEMIC_LUPUS_ERYTHEMATOSUS | 15 | 0.708549 | 1.943889 | 0 | 0.032521 | 0.309 | 1214 | tags = 40%, list = 6%, signal = 42% |
| DIAZ_CHRONIC_MEYLOGENOUS_LEUKEMIA_DN | 93 | 0.46659 | 1.927104 | 0 | 0.036564 | 0.377 | 4481 | tags = 40%, list = 20%, signal = 50% |
| VALK_AML_CLUSTER_13 | 23 | 0.601074 | 1.888098 | 0 | 0.05322 | 0.546 | 2951 | tags = 30%, list = 13%, signal = 35% |
| LEE_DIFFERENTIATING_T_LYMPHOCYTE | 108 | 0.453179 | 1.885657 | 0 | 0.049074 | 0.553 | 6782 | tags = 53%, list = 31%, signal = 76% |
| SHIPP_DLBCL_VS_FOLLICULAR_LYMPHOMA_DN | 37 | 0.531142 | 1.841607 | 0.001667 | 0.078602 | 0.748 | 3348 | tags = 41%, list = 15%, signal = 48% |
| KOBAYASHI_EGFR_SIGNALING_24HR_UP | 74 | 0.468195 | 1.834232 | 0 | 0.078615 | 0.774 | 6106 | tags = 55%, list = 28%, signal = 77% |
| TAKEDA_TARGETS_OF_NUP98_HOXA9_FUSION_8D_UP | 116 | 0.431239 | 1.832117 | 0 | 0.074563 | 0.783 | 3846 | tags = 34%, list = 18%, signal = 41% |
| KIM_LRRC3B_TARGETS | 17 | 0.646053 | 1.821081 | 0.001905 | 0.077972 | 0.824 | 2963 | tags = 41%, list = 14%, signal = 48% |
| FARMER_BREAST_CANCER_CLUSTER_1 | 30 | 0.552833 | 1.813877 | 0.001718 | 0.079269 | 0.844 | 3680 | tags = 43%, list = 17%, signal = 52% |

TABLE 1-continued

| NAME | SIZE | ES | NES | NOM p-val | FDR q-val | FWER p-val | RANK AT MAX | LEADING EDGE |
|---|---|---|---|---|---|---|---|---|
| BROWNE_INTERFERON_RESPONSIVE_GENES | 51 | 0.485545 | 1.804869 | 0 | 0.081404 | 0.867 | 4417 | tags = 43%, list = 20%, signal = 54% |
| LIAN_LIPA_TARGETS_6M | 78 | 0.448416 | 1.799782 | 0.00159 | 0.081092 | 0.885 | 2866 | tags = 37%, list = 13%, signal = 43% |
| FLECHNER_BIOPSY_KIDNEY_TRANSPLANT_REJECTED_VS_OK_UP | 76 | 0.448979 | 1.798828 | 0 | 0.077551 | 0.889 | 5328 | tags = 43%, list = 24%, signal = 57% |
| EINAV_INTERFERON_SIGNATURE_IN_CANCER | 18 | 0.610528 | 1.781675 | 0.003617 | 0.08978 | 0.927 | 5629 | tags = 61%, list = 26%, signal = 82% |
| YU_MYC_TARGETS_DN | 53 | 0.478017 | 1.767861 | 0.001698 | 0.098859 | 0.952 | 5167 | tags = 47%, list = 24%, signal = 62% |
| BOYLAN_MULTIPLE_MYELOMA_C_D_DN | 247 | 0.37653 | 1.761921 | 0 | 0.100015 | 0.96 | 4439 | tags = 36%, list = 20%, signal = 45% |
| RODRIGUES_DCC_TARGETS_DN | 105 | 0.420315 | 1.75343 | 0 | 0.103495 | 0.971 | 2763 | tags = 28%, list = 13%, signal = 31% |
| ZHANG_INTERFERON_RESPONSE | 15 | 0.639616 | 1.753212 | 0.003697 | 0.099156 | 0.971 | 3609 | tags = 47%, list = 16%, signal = 56% |
| ZHAN_MULTIPLE_MYELOMA_PR_DN | 35 | 0.51926 | 1.7504 | 0.001757 | 0.097936 | 0.973 | 3855 | tags = 49%, list = 18%, signal = 59% |
| ODONNELL_TARGETS_OF_MYC_AND_TFRC_UP | 54 | 0.467824 | 1.749903 | 0.001757 | 0.094416 | 0.973 | 5445 | tags = 54%, list = 25%, signal = 71% |
| WIELAND_UP_BY_HBV_INFECTION | 75 | 0.438772 | 1.740891 | 0 | 0.099804 | 0.979 | 2632 | tags = 24%, list = 12%, signal = 27% |
| LIU_VAV3_PROSTATE_CARCINOGENESIS_UP | 78 | 0.435901 | 1.721277 | 0 | 0.117502 | 0.994 | 6060 | tags = 50%, list = 28%, signal = 69% |
| MORI_MATURE_B_LYMPHOCYTE_UP | 72 | 0.439127 | 1.718323 | 0.001658 | 0.116508 | 0.995 | 4855 | tags = 38%, list = 22%, signal = 48% |
| DAUER_STAT3_TARGETS_DN | 28 | 0.536905 | 1.715527 | 0.00726 | 0.11592 | 0.996 | 4417 | tags = 57%, list = 20%, signal = 71% |
| HOFFMANN_IMMATURE_TO_MATURE_B_LYMPHOCYTE_UP | 26 | 0.540776 | 1.714734 | 0.009259 | 0.113128 | 0.996 | 1683 | tags = 31%, list = 8%, signal = 33% |
| ICHIBA_GRAFT_VERSUS_HOST_DISEASE_D7_UP | 105 | 0.410042 | 1.713352 | 0 | 0.111118 | 0.996 | 6418 | tags = 48%, list = 29%, signal = 67% |
| TAKEDA_TARGETS_OF_NUP98_HOXA9_FUSION_10D_UP | 133 | 0.385752 | 1.691537 | 0 | 0.133156 | 0.999 | 4645 | tags = 36%, list = 21%, signal = 46% |
| ZIRN_TRETINOIN_RESPONSE_WT1_UP | 17 | 0.591184 | 1.689255 | 0.013283 | 0.132356 | 1 | 5401 | tags = 59%, list = 25%, signal = 78% |
| MCCABE_HOXC6_TARGETS_DN | 17 | 0.586301 | 1.683937 | 0.010772 | 0.13554 | 1 | 3036 | tags = 35%, list = 14%, signal = 41% |
| YAO_TEMPORAL_RESPONSE_TO_PROGESTERONE_CLUSTER_3 | 16 | 0.58783 | 1.675209 | 0.009191 | 0.143467 | 1 | 1698 | tags = 25%, list = 8%, signal = 27% |
| WIKMAN_ASBESTOS_LUNG_CANCER_DN | 22 | 0.535219 | 1.668022 | 0.024074 | 0.149581 | 1 | 2001 | tags = 32%, list = 9%, signal = 35% |
| WINTER_HYPOXIA_DN | 40 | 0.472244 | 1.664049 | 0 | 0.150173 | 1 | 4581 | tags = 48%, list = 21%, signal = 60% |
| SMID_BREAST_CANCER_NORMAL_LIKE_UP | 362 | 0.3405 | 1.6616 | 0 | 0.149654 | 1 | 4626 | tags = 33%, list = 21%, signal = 42% |
| LIAN_LIPA_TARGETS_3M | 65 | 0.434176 | 1.661359 | 0.001672 | 0.146133 | 1 | 3112 | tags = 35%, list = 14%, signal = 41% |
| CAIRO_HEPATOBLASTOMA_CLASSES_DN | 172 | 0.367863 | 1.659135 | 0 | 0.145556 | 1 | 5734 | tags = 37%, list = 26%, signal = 50% |

TABLE 1-continued

| NAME | SIZE | ES | NES | NOM p-val | FDR q-val | FWER p-val | RANK AT MAX | LEADING EDGE |
|---|---|---|---|---|---|---|---|---|
| ROSS_AML_WITH_CBFB_MYH11_FUSION | 43 | 0.464084 | 1.658638 | 0.003559 | 0.142786 | 1 | 5542 | tags = 51%, list = 25%, signal = 68% |
| YAO_TEMPORAL_RESPONSE_TO_PROGESTERONE_CLUSTER_0 | 71 | 0.417113 | 1.646051 | 0 | 0.15584 | 1 | 5708 | tags = 52%, list = 26%, signal = 70% |
| HADDAD_T_LYMPHOCYTE_AND_NK_PROGENITOR_DN | 55 | 0.436019 | 1.64187 | 0.00659 | 0.1582 | 1 | 1281 | tags = 25%, list = 6%, signal = 27% |
| HESS_TARGETS_OF_HOXA9_AND_MEIS1_DN | 76 | 0.41417 | 1.631702 | 0.007874 | 0.169431 | 1 | 5960 | tags = 51%, list = 27%, signal = 70% |
| DUNNE_TARGETS_OF_AML1_MTG8_FUSION_UP | 36 | 0.478438 | 1.629428 | 0.010582 | 0.168833 | 1 | 2167 | tags = 28%, list = 10%, signal = 31% |
| YAO_TEMPORAL_RESPONSE_TO_PROGESTERONE_CLUSTER_1 | 71 | 0.409811 | 1.621562 | 0.001692 | 0.176764 | 1 | 5217 | tags = 38%, list = 24%, signal = 50% |
| ST_ADRENERGIC | 31 | 0.488004 | 1.61073 | 0.019097 | 0.190594 | 1 | 4284 | tags = 29%, list = 20%, signal = 36% |
| RAMALHO_STEMNESS_DN | 69 | 0.409625 | 1.609626 | 0.007092 | 0.188375 | 1 | 5444 | tags = 36%, list = 25%, signal = 48% |
| YANG_BREAST_CANCER_ESR1_BULK_UP | 15 | 0.570111 | 1.608223 | 0.022642 | 0.186854 | 1 | 4987 | tags = 33%, list = 23%, signal = 43% |
| GUTIERREZ_CHRONIC_LYMPHOCYTIC_LEUKEMIA_DN | 46 | 0.444619 | 1.606409 | 0.014363 | 0.185868 | 1 | 4049 | tags = 35%, list = 18%, signal = 43% |
| MARKEY_RB1_ACUTE_LOF_UP | 215 | 0.342148 | 1.601109 | 0 | 0.1904 | 1 | 6081 | tags = 40%, list = 28%, signal = 55% |
| REACTOME_CD28_CO_STIMULATION | 25 | 0.509357 | 1.592281 | 0.014519 | 0.201624 | 1 | 4052 | tags = 28%, list = 19%, signal = 34% |
| SEITZ_NEOPLASTIC_TRANSFORMATION_BY_8P_DELETION_UP | 60 | 0.417038 | 1.581352 | 0.011419 | 0.216585 | 1 | 5045 | tags = 42%, list = 23%, signal = 54% |
| RIZ_ERYTHROID_DIFFERENTIATION_12HR | 41 | 0.447639 | 1.580376 | 0.017575 | 0.214328 | 1 | 4839 | tags = 32%, list = 22%, signal = 41% |
| CHUNG_BLISTER_CYTOTOXICITY_DN | 28 | 0.484896 | 1.579003 | 0.016129 | 0.212803 | 1 | 4644 | tags = 46%, list = 21%, signal = 59% |
| YANG_BREAST_CANCER_ESR1_UP | 19 | 0.540089 | 1.575191 | 0.024528 | 0.215073 | 1 | 4051 | tags = 37%, list = 19%, signal = 45% |
| FULCHER_INFLAMMATORY_RESPONSE_LECTIN_VS_LPS_DN | 318 | 0.326276 | 1.568222 | 0 | 0.223651 | 1 | 5907 | tags = 36%, list = 27%, signal = 49% |
| ZUCCHI_METASTASIS_UP | 20 | 0.531876 | 1.565082 | 0.023636 | 0.22572 | 1 | 3847 | tags = 30%, list = 18%, signal = 36% |
| CHARAFE_BREAST_CANCER_BASAL_VS_MESENCHYMAL_DN | 39 | 0.452651 | 1.563495 | 0.015652 | 0.224905 | 1 | 1668 | tags = 23%, list = 8%, signal = 25% |
| ZHAN_MULTIPLE_MYELOMA_DN | 25 | 0.496399 | 1.556541 | 0.022887 | 0.234662 | 1 | 2712 | tags = 28%, list = 12%, signal = 32% |
| WEST_ADRENOCORTICAL_CARCINOMA_VS_ADENOMA_DN | 17 | 0.551168 | 1.548203 | 0.025194 | 0.246394 | 1 | 2788 | tags = 29%, list = 13%, signal = 34% |
| LIANG_HEMATOPOIESIS_STEM_CELL_NUMBER_SMALL_VS_HUGE_DN | 30 | 0.477597 | 1.547156 | 0.021016 | 0.244334 | 1 | 5927 | tags = 43%, list = 27%, signal = 59% |
| NEWMAN_ERCC6_TARGETS_UP | 19 | 0.514551 | 1.546377 | 0.032143 | 0.242099 | 1 | 3307 | tags = 47%, list = 15%, signal = 56% |
| TAKEDA_TARGETS_OF_NUP98_HOXA9_FUSION_16D_UP | 124 | 0.363496 | 1.544956 | 0.003257 | 0.240995 | 1 | 3846 | tags = 30%, list = 18%, signal = 36% |
| GARGALOVIC_RESPONSE_TO_OXIDIZED_PHOSPHOLIPIDS_RED_DN | 17 | 0.547073 | 1.537267 | 0.033028 | 0.252503 | 1 | 2897 | tags = 29%, list = 13%, signal = 34% |

TABLE 1-continued

| NAME | SIZE | ES | NES | NOM p-val | FDR q-val | FWER p-val | RANK AT MAX | LEADING EDGE |
|---|---|---|---|---|---|---|---|---|
| ZHANG_ANTIVIRAL_RESPONSE_TO_RIBAVIRIN_UP | 22 | 0.511479 | 1.536626 | 0.028725 | 0.249823 | 1 | 2272 | tags = 27%, list = 10%, signal = 30% |
| ICHIBA_GRAFT_VERSUS_HOST_DISEASE_35D_UP | 128 | 0.353342 | 1.533823 | 0.004992 | 0.25164 | 1 | 3262 | tags = 25%, list = 15%, signal = 29% |
| XU_GH1_EXOGENOUS_TARGETS_DN | 71 | 0.387572 | 1.527815 | 0.010017 | 0.259812 | 1 | 5208 | tags = 41%, list = 24%, signal = 53% |
| NAKAJIMA_MAST_CELL | 28 | 0.475146 | 1.527363 | 0.036649 | 0.256969 | 1 | 1422 | tags = 25%, list = 6%, signal = 27% |
| RADAEVA_RESPONSE_TO_IFNA1_UP | 28 | 0.475943 | 1.525465 | 0.025 | 0.257156 | 1 | 1652 | tags = 21%, list = 8%, signal = 23% |
| TAKEDA_TARGETS_OF_NUP98_HOXA9_FUSION_8D_DN | 142 | 0.346459 | 1.525141 | 0.003145 | 0.254247 | 1 | 5601 | tags = 39%, list = 26%, signal = 53% |
| ROY_WOUND_BLOOD_VESSEL_UP | 41 | 0.439538 | 1.520434 | 0.028881 | 0.260229 | 1 | 3701 | tags = 32%, list = 17%, signal = 38% |
| KRASNOSELSKAYA_ILF3_TARGETS_UP | 22 | 0.4992 | 1.514133 | 0.02852 | 0.269079 | 1 | 1532 | tags = 27%, list = 7%, signal = 29% |
| BIOCARTA_IL7_PATHWAY | 17 | 0.529018 | 1.513342 | 0.054104 | 0.266965 | 1 | 6967 | tags = 59%, list = 32%, signal = 86% |
| SEKI_INFLAMMATORY_RESPONSE_LPS_DN | 22 | 0.50008 | 1.513179 | 0.028829 | 0.263809 | 1 | 5462 | tags = 50%, list = 25%, signal = 67% |
| CHEOK_RESPONSE_TO_HD_MTX_UP | 15 | 0.54034 | 1.505168 | 0.052533 | 0.276692 | 1 | 4411 | tags = 60%, list = 20%, signal = 75% |
| REACTOME_GENERATION_OF_SECOND_MESSENGER_MOLECULES | 20 | 0.503759 | 1.503832 | 0.046632 | 0.275974 | 1 | 7129 | tags = 55%, list = 33%, signal = 81% |
| LIANG_SILENCED_BY_METHYLATION_2 | 26 | 0.476262 | 1.498888 | 0.036269 | 0.283112 | 1 | 2867 | tags = 31%, list = 13%, signal = 35% |
| GNATENKO_PLATELET_SIGNATURE | 28 | 0.452962 | 1.495195 | 0.038321 | 0.287571 | 1 | 1177 | tags = 7%, list = 5%, signal = 8% |
| WALLACE_PROSTATE_CANCER_RACE_UP | 213 | 0.324127 | 1.487432 | 0.003017 | 0.301274 | 1 | 3262 | tags = 25%, list = 15%, signal = 29% |

TABLE 2

| NAME | SIZE | ES | NES | NOM p-val | FDR q-val | FWER p-val | RANK AT MAX | LEADING EDGE |
|---|---|---|---|---|---|---|---|---|
| MANALO_HYPOXIA_DN | 233 | -0.6248 | -3.10267 | 0 | 0 | 0 | 5952 | tags = 75%, list = 27%, signal = 102% |
| SHEDDEN_LUNG_CANCER_POOR_SURVIVAL_A6 | 363 | -0.5568 | -2.90709 | 0 | 0 | 0 | 6869 | tags = 67%, list = 31%, signal = 96% |
| ROSTY_CERVICAL_CANCER_PROLIFERATION_CLUSTER | 119 | -0.63271 | -2.88451 | 0 | 0 | 0 | 5413 | tags = 68%, list = 25%, signal = 90% |
| CAIRO_HEPATOBLASTOMA_CLASSES_UP | 491 | -0.52038 | -2.80827 | 0 | 0 | 0 | 6692 | tags = 62%, list = 31%, signal = 87% |
| SOTIRIOU_BREAST_CANCER_GRADE_1_VS_3_UP | 119 | -0.61776 | -2.79674 | 0 | 0 | 0 | 6027 | tags = 73%, list = 28%, signal = 100% |
| KOBAYASHI_EGFR_SIGNALING_24HR_DN | 210 | -0.56625 | -2.76693 | 0 | 0 | 0 | 4922 | tags = 61%, list = 22%, signal = 78% |
| FOURNIER_ACINAR_DEVELOPMENT_LATE_2 | 234 | -0.54704 | -2.72639 | 0 | 0 | 0 | 6692 | tags = 60%, list = 31%, signal = 86% |
| BERENJENO_TRANSFORMED_BY_RHOA_UP | 474 | -0.50701 | -2.724 | 0 | 0 | 0 | 6265 | tags = 61%, list = 29%, signal = 83% |
| WONG_EMBRYONIC_STEM_CELL_CORE | 294 | -0.52557 | -2.72324 | 0 | 0 | 0 | 6153 | tags = 58%, list = 28%, signal = 80% |
| YAO_TEMPORAL_RESPONSE_TO_PROGESTERONE_CLUSTER_11 | 94 | -0.61381 | -2.66053 | 0 | 0 | 0 | 5876 | tags = 67%, list = 27%, signal = 91% |
| CRONQUIST_IL6_DEPRIVATION_DN | 70 | -0.63924 | -2.65141 | 0 | 0 | 0 | 6153 | tags = 80%, list = 28%, signal = 111% |
| HOFFMANN_LARGE_TO_SMALL_PRE_BII_LYMPHOCYTE_UP | 89 | -0.60027 | -2.58164 | 0 | 0 | 0 | 4901 | tags = 64%, list = 22%, signal = 82% |
| U_MYC_TARGETS_UP | 37 | -0.71553 | -2.55861 | 0 | 0 | 0 | 5413 | tags = 89%, list = 25%, signal = 118% |
| ODONNELL_TARGETS_OF_MYC_AND_TFRC_DN | 33 | -0.72466 | -2.55781 | 0 | 0 | 0 | 5292 | tags = 91%, list = 24%, signal = 120% |
| WINNEPENNINCKX_MELANOMA_METASTASIS_UP | 119 | -0.56021 | -2.55758 | 0 | 0 | 0 | 6951 | tags = 73%, list = 32%, signal = 107% |
| YAO_TEMPORAL_RESPONSE_TO_PROGESTERONE_CLUSTER_14 | 115 | -0.56693 | -2.5469 | 0 | 0 | 0 | 7004 | tags = 70%, list = 32%, signal = 102% |
| RODRIGUES_THYROID_CARCINOMA_POORLY_DIFFERENTIATED_UP | 489 | -0.46802 | -2.53179 | 0 | 0 | 0 | 5968 | tags = 51%, list = 27%, signal = 68% |
| FUJII_YBX1_TARGETS_DN | 125 | -0.54196 | -2.49594 | 0 | 0 | 0 | 4939 | tags = 53%, list = 23%, signal = 68% |
| CRONQUIST_NRAS_SIGNALING_DN | 54 | -0.63419 | -2.48885 | 0 | 0 | 0 | 6153 | tags = 76%, list = 28%, signal = 105% |
| GRAHAM_NORMAL_QUIESCENT_VS_NORMAL_DIVIDING_DN | 70 | -0.60518 | -2.48278 | 0 | 0 | 0 | 6063 | tags = 76%, list = 28%, signal = 104% |
| REACTOME_LATE_PHASE_OF_HIV_LIFE_CYCLE | 87 | -0.5748 | -2.47952 | 0 | 0 | 0 | 8431 | tags = 80%, list = 39%, signal = 130% |
| KAUFFMANN_MELANOMA_RELAPSE_UP | 54 | -0.62378 | -2.47485 | 0 | 0 | 0 | 5554 | tags = 59%, list = 25%, signal = 79% |
| SCHUHMACHER_MYC_TARGETS_UP | 61 | -0.61714 | -2.471 | 0 | 0 | 0 | 5506 | tags = 64%, list = 25%, signal = 85% |
| REACTOME_CELL_CYCLE_MITOTIC | 262 | -0.48339 | -2.46512 | 0 | 0 | 0 | 6909 | tags = 56%, list = 32%, signal = 81% |

TABLE 2-continued

| NAME | SIZE | ES | NES | NOM p-val | FDR q-val | FWER p-val | RANK AT MAX | LEADING EDGE |
|---|---|---|---|---|---|---|---|---|
| KAUFFMANN_DNA_REPAIR_GENES | 187 | −0.50159 | −2.46045 | 0 | 0 | 0 | 6218 | tags = 55%, list = 28%, signal = 76% |
| PUJANA_BRCA_CENTERED_NETWORK | 89 | −0.56638 | −2.45856 | 0 | 0 | 0 | 7277 | tags = 73%, list = 33%, signal = 109% |
| REACTOME_MITOTIC_M_M_G1_PHASES | 135 | −0.53123 | −2.44983 | 0 | 0 | 0 | 6909 | tags = 60%, list = 32%, signal = 87% |
| REACTOME_SNRNP_ASSEMBLY | 45 | −0.65052 | −2.44495 | 0 | 0 | 0 | 6439 | tags = 76%, list = 29%, signal = 107% |
| BASAKI_YBX1_TARGETS_UP | 222 | −0.49822 | −2.44417 | 0 | 0 | 0 | 5554 | tags = 57%, list = 25%, signal = 75% |
| ODONNELL_TFRC_TARGETS_DN | 97 | −0.55664 | −2.43787 | 0 | 0 | 0 | 6126 | tags = 68%, list = 28%, signal = 94% |
| FRASOR_RESPONSE_TO_SERM_OR_FULVESTRANT_DN | 41 | −0.65506 | −2.42734 | 0 | 0 | 0 | 4941 | tags = 66%, list = 23%, signal = 85% |
| REACTOME_HIV_LIFE_CYCLE | 100 | −0.54912 | −2.4228 | 0 | 0 | 0 | 5861 | tags = 59%, list = 27%, signal = 80% |
| MUELLER_PLURINET | 259 | −0.47566 | −2.41338 | 0 | 0 | 0 | 6395 | tags = 54%, list = 29%, signal = 75% |
| PUJANA_XPRSS_INT_NETWORK | 140 | −0.51444 | −2.40556 | 0 | 0 | 0 | 7526 | tags = 65%, list = 34%, signal = 98% |
| RUIZ_TNC_TARGETS_DN | 119 | −0.53597 | −2.40153 | 0 | 0 | 0 | 4777 | tags = 51%, list = 22%, signal = 65% |
| REACTOME_DNA_REPAIR | 94 | −0.55297 | −2.39978 | 0 | 0 | 0 | 5861 | tags = 61%, list = 27%, signal = 82% |
| REACTOME_S_PHASE | 96 | −0.54082 | −2.37791 | 0 | 0 | 0 | 6833 | tags = 60%, list = 31%, signal = 87% |
| BIDUS_METASTASIS_UP | 158 | −0.51165 | −2.37316 | 0 | 0 | 0 | 7136 | tags = 63%, list = 33%, signal = 93% |
| WHITEFORD_PEDIATRIC_CANCER_MARKERS | 86 | −0.54806 | −2.36761 | 0 | 3.93E−05 | 0.001 | 7069 | tags = 72%, list = 32%, signal = 106% |
| REACTOME_G2_M_CHECKPOINTS | 40 | −0.63598 | −2.36258 | 0 | 3.83E−05 | 0.001 | 5555 | tags = 70%, list = 25%, signal = 94% |
| REACTOME_METABOLISM_OF_RNA | 87 | −0.54929 | −2.35909 | 0 | 3.74E−05 | 0.001 | 7211 | tags = 69%, list = 33%, signal = 102% |
| NAKAMURA_CANCER_MICROENVIRONMENT_DN | 41 | −0.63668 | −2.35679 | 0 | 3.65E−05 | 0.001 | 3730 | tags = 56%, list = 17%, signal = 67% |
| BENPORATH_PROLIFERATION | 116 | −0.51614 | −2.35319 | 0 | 3.56E−05 | 0.001 | 6389 | tags = 59%, list = 29%, signal = 82% |
| LINDGREN_BLADDER_CANCER_CLUSTER_3_UP | 251 | −0.46393 | −2.34652 | 0 | 3.48E−05 | 0.001 | 6686 | tags = 54%, list = 31%, signal = 77% |
| WAKASUGI_HAVE_ZNF143_BINDING_SITES | 53 | −0.59959 | −2.3417 | 0 | 3.40E−05 | 0.001 | 5772 | tags = 68%, list = 26%, signal = 92% |
| SCHLOSSER_MYC_TARGETS_REPRESSED_BY_SERUM | 121 | −0.51909 | −2.34105 | 0 | 3.33E−05 | 0.001 | 6356 | tags = 57%, list = 29%, signal = 80% |
| REACTOME_SYNTHESIS_OF_DNA | 83 | −0.54736 | −2.30879 | 0 | 1.32E−04 | 0.004 | 8423 | tags = 77%, list = 38%, signal = 125% |
| REACTOME_TRANSPORT_OF_MATURE_MRNA_DERIVED_FROM_AN_INTRON_CONTAINING_TRANSCRIPT | 49 | −0.59175 | −2.29609 | 0 | 1.30E−04 | 0.004 | 7817 | tags = 78%, list = 36%, signal = 120% |
| REACTOME_MITOTIC_PROMETAPHASE | 71 | −0.55579 | −2.2958 | 0 | 1.27E−04 | 0.004 | 6280 | tags = 59%, list = 29%, signal = 83% |

TABLE 2-continued

| NAME | SIZE | ES | NES | NOM p-val | FDR q-val | FWER p-val | RANK AT MAX | LEADING EDGE |
|---|---|---|---|---|---|---|---|---|
| GRAHAM_CML_DIVIDING_VS_NORMAL_QUIESCENT_UP | 152 | −0.48848 | −2.29571 | 0 | 1.24E-04 | 0.004 | 6063 | tags = 65%, list = 28%, signal = 89% |
| REACTOME_HIV_INFECTION | 175 | −0.47404 | −2.29196 | 0 | 1.22E-04 | 0.004 | 8431 | tags = 68%, list = 39%, signal = 110% |
| REACTOME_DNA_REPLICATION_PRE_INITIATION | 72 | −0.54465 | −2.28201 | 0 | 1.20E-04 | 0.004 | 8423 | tags = 76%, list = 38%, signal = 124% |
| MARKEY_RB1_ACUTE_LOF_DN | 213 | −0.46076 | −2.27719 | 0 | 1.17E-04 | 0.004 | 5479 | tags = 51%, list = 25%, signal = 67% |
| REN_BOUND_BY_E2F | 46 | −0.60126 | −2.27011 | 0 | 1.15E-04 | 0.004 | 6811 | tags = 78%, list = 31%, signal = 113% |
| BLUM_RESPONSE_TO_SALIRASIB_DN | 307 | −0.43985 | −2.26538 | 0 | 1.42E-04 | 0.005 | 6203 | tags = 50%, list = 28%, signal = 69% |
| GARCIA_TARGETS_OF_FLI1_AND_DAX1_DN | 110 | −0.50543 | −2.26225 | 0 | 1.68E-04 | 0.006 | 4187 | tags = 47%, list = 19%, signal = 58% |
| REACTOME_RNA_POLYMERASE_II_TRANSCRIPTION | 86 | −0.52681 | −2.26175 | 0 | 1.65E-04 | 0.006 | 9169 | tags = 80%, list = 42%, signal = 138% |
| HESS_TARGETS_OF_HOXA9_AND_MEIS1_UP | 61 | −0.56804 | −2.2611 | 0 | 1.62E-04 | 0.006 | 6153 | tags = 69%, list = 28%, signal = 96% |
| REACTOME_CELL_CYCLE_CHECKPOINTS | 105 | −0.51244 | −2.26088 | 0 | 1.59E-04 | 0.006 | 8446 | tags = 72%, list = 39%, signal = 117% |
| TOYOTA_TARGETS_OF_MIR34B_AND_MIR34C | 302 | −0.43657 | −2.25848 | 0 | 1.83E-04 | 0.007 | 5294 | tags = 47%, list = 24%, signal = 62% |
| LE_EGR2_TARGETS_UP | 99 | −0.50456 | −2.24365 | 0 | 2.57E-04 | 0.01 | 5571 | tags = 60%, list = 25%, signal = 80% |
| WELCSH_BRCA1_TARGETS_1_DN | 103 | −0.50022 | −2.24119 | 0 | 2.53E-04 | 0.01 | 5398 | tags = 49%, list = 25%, signal = 64% |
| ZHAN_MULTIPLE_MYELOMA_PR_UP | 30 | −0.66657 | −2.23876 | 0 | 2.49E-04 | 0.01 | 5457 | tags = 73%, list = 25%, signal = 98% |
| SCHLOSSER_MYC_TARGETS_AND_SERUM_RESPONSE_UP | 42 | −0.5993 | −2.23838 | 0 | 2.45E-04 | 0.01 | 7170 | tags = 79%, list = 33%, signal = 117% |
| KANG_DOXORUBICIN_RESISTANCE_UP | 42 | −0.60911 | −2.23058 | 0 | 2.41E-04 | 0.01 | 6063 | tags = 79%, list = 28%, signal = 108% |
| REACTOME_TRANSCRIPTION_OF_THE_HIV_GENOME | 56 | −0.55479 | −2.22406 | 0 | 2.37E-04 | 0.01 | 8431 | tags = 77%, list = 39%, signal = 125% |
| YAO_TEMPORAL_RESPONSE_TO_PROGESTERONE_CLUSTER_17 | 162 | −0.46632 | −2.22323 | 0 | 2.34E-04 | 0.01 | 8156 | tags = 58%, list = 37%, signal = 92% |
| KEGG_AMINOACYL_TRNA_BIOSYNTHESIS | 29 | −0.65833 | −2.22232 | 0 | 2.30E-04 | 0.01 | 5501 | tags = 76%, list = 25%, signal = 101% |
| BIOCARTA_CYTOKINE_PATHWAY | 19 | −0.73463 | −2.22217 | 0 | 2.27E-04 | 0.01 | 1999 | tags = 58%, list = 9%, signal = 64% |
| VECCHI_GASTRIC_CANCER_EARLY_UP | 312 | −0.43099 | −2.22032 | 0 | 2.24E-04 | 0.01 | 5572 | tags = 49%, list = 25%, signal = 65% |
| FINETTI_BREAST_CANCER_KINOME_RED | 15 | −0.77765 | −2.22007 | 0 | 2.21E-04 | 0.01 | 3773 | tags = 80%, list = 17%, signal = 97% |
| SONG_TARGETS_OF_IE86_CMV_PROTEIN | 42 | −0.59892 | −2.2135 | 0 | 2.61E-04 | 0.011 | 6296 | tags = 69%, list = 29%, signal = 97% |
| FINETTI_BREAST_CANCER_BASAL_VS_LUMINAL | 15 | −0.77765 | −2.21228 | 0 | 2.58E-04 | 0.011 | 3773 | tags = 80%, list = 17%, signal = 97% |
| FERREIRA_EWINGS_SARCOMA_UNSTABLE_VS_STABLE_UP | 110 | −0.48933 | −2.21168 | 0 | 2.54E-04 | 0.011 | 6401 | tags = 62%, list = 29%, signal = 87% |

TABLE 2-continued

| NAME | SIZE | ES | NES | NOM p-val | FDR q-val | FWER p-val | RANK AT MAX | LEADING EDGE |
|---|---|---|---|---|---|---|---|---|
| REACTOME_ACTIVATION_OF_ATR_IN_RESPONSE_TO_REPLICATION_STRESS | 35 | -0.63192 | -2.21151 | 0 | 2.51E-04 | 0.011 | 6833 | tags = 80%, list = 31%, signal = 116% |
| REACTOME_TRNA_AMINOACYLATION | 28 | -0.65329 | -2.20926 | 0 | 2.47E-04 | 0.011 | 5918 | tags = 79%, list = 27%, signal = 108% |
| REACTOME_REV_MEDIATED_NUCLEAR_EXPORT_OF_HIV1_RNA | 31 | -0.63725 | -2.2092 | 0 | 2.44E-04 | 0.011 | 6272 | tags = 74%, list = 29%, signal = 104% |
| PUJANA_BRCA2_PCC_NETWORK | 354 | -0.42091 | -2.19518 | 0 | 3.01E-04 | 0.014 | 6984 | tags = 55%, list = 32%, signal = 80% |
| PUJANA_BREAST_CANCER_WITH_BRCA1_MUTATED_UP | 48 | -0.57048 | -2.19223 | 0 | 2.97E-04 | 0.014 | 7650 | tags = 69%, list = 35%, signal = 105% |
| BENPORATH_CYCLING_GENES | 487 | -0.40496 | -2.18482 | 0 | 2.94E-04 | 0.014 | 6063 | tags = 47%, list = 28%, signal = 63% |
| TARTE_PLASMA_CELL_VS_PLASMABLAST_DN | 264 | -0.43192 | -2.18475 | 0 | 2.90E-04 | 0.014 | 6794 | tags = 50%, list = 31%, signal = 72% |
| ZHANG_BREAST_CANCER_PROGENITORS_UP | 356 | -0.41639 | -2.18359 | 0 | 2.86E-04 | 0.014 | 5110 | tags = 39%, list = 23%, signal = 50% |
| MOLENAAR_TARGETS_OF_CCND1_AND_CDK4_DN | 38 | -0.59147 | -2.18357 | 0 | 2.83E-04 | 0.014 | 5413 | tags = 68%, list = 25%, signal = 91% |
| CHEMNITZ_RESPONSE_TO_PROSTAGLANDIN_E2_UP | 105 | -0.49243 | -2.18272 | 0 | 2.80E-04 | 0.014 | 5603 | tags = 53%, list = 26%, signal = 71% |
| CHIANG_LIVER_CANCER_SUBCLASS_PROLIFERATION_UP | 126 | -0.48551 | -2.17998 | 0 | 2.94E-04 | 0.015 | 6037 | tags = 59%, list = 28%, signal = 81% |
| MORI_IMMATURE_B_LYMPHOCYTE_DN | 51 | -0.56172 | -2.17923 | 0 | 3.09E-04 | 0.016 | 4901 | tags = 55%, list = 22%, signal = 71% |
| LI_WILMS_TUMOR_VS_FETAL_KIDNEY_1_DN | 143 | -0.47552 | -2.17785 | 0 | 3.58E-04 | 0.019 | 6032 | tags = 57%, list = 28%, signal = 79% |
| REACTOME_G1_S_TRANSITION | 95 | -0.49882 | -2.16889 | 0 | 4.24E-04 | 0.023 | 8423 | tags = 76%, list = 38%, signal = 123% |
| REACTOME_ORC1_REMOVAL_FROM_CHROMATIN | 62 | -0.53445 | -2.16413 | 0 | 4.19E-04 | 0.023 | 8423 | tags = 76%, list = 38%, signal = 123% |
| REACTOME_VPR_MEDIATED_NUCLEAR_IMPORT_OF_PICS | 31 | -0.62822 | -2.16243 | 0 | 4.31E-04 | 0.024 | 6272 | tags = 71%, list = 29%, signal = 99% |
| MARZEC_IL2_SIGNALING_UP | 95 | -0.5007 | -2.1622 | 0 | 4.27E-04 | 0.024 | 3897 | tags = 46%, list = 18%, signal = 56% |
| LEE_EARLY_T_LYMPHOCYTE_UP | 62 | -0.53445 | -2.16142 | 0 | 4.22E-04 | 0.024 | 6063 | tags = 66%, list = 28%, signal = 91% |
| BOYAULT_LIVER_CANCER_SUBCLASS_G3_UP | 141 | -0.46084 | -2.1547 | 0 | 4.17E-04 | 0.024 | 7315 | tags = 61%, list = 33%, signal = 91% |
| REACTOME_TRANSPORT_OF_THE_SLBP_INDEPENDENT_MATURE_MRNA | 31 | -0.62469 | -2.1546 | 0 | 4.13E-04 | 0.024 | 6272 | tags = 71%, list = 29%, signal = 99% |
| REACTOME_M_G1_TRANSITION | 60 | -0.53293 | -2.15376 | 0 | 4.09E-04 | 0.024 | 8423 | tags = 75%, list = 38%, signal = 122% |
| REACTOME_FORMATION_AND_MATURATION_OF_MRNA_TRANSCRIPT | 124 | -0.46416 | -2.14877 | 0 | 4.04E-04 | 0.024 | 7557 | tags = 61%, list = 35%, signal = 93% |
| CROONQUIST_NRAS_VS_STROMAL_STIMULATION_DN | 67 | -0.52518 | -2.14495 | 0 | 4.00E-04 | 0.024 | 4737 | tags = 52%, list = 22%, signal = 66% |
| REACTOME_ACTIVATION_OF_THE_PRE_REPLICATIVE_COMPLEX | 27 | -0.64535 | -2.13937 | 0 | 4.43E-04 | 0.027 | 6833 | tags = 85%, list = 31%, signal = 124% |
| FURUKAWA_DUSP6_TARGETS_PCI35_DN | 53 | -0.54107 | -2.13646 | 0 | 4.70E-04 | 0.029 | 5506 | tags = 64%, list = 25%, signal = 86% |

TABLE 2-continued

| NAME | SIZE | ES | NES | NOM p-val | FDR q-val | FWER p-val | RANK AT MAX | LEADING EDGE |
|---|---|---|---|---|---|---|---|---|
| REACTOME_NEP_NS2_INTERACTS_WITH_THE_CELLULAR_EXPORT_MACHINERY | 29 | −0.63219 | −2.13521 | 0 | 4.65E-04 | 0.029 | 6272 | tags = 72%, list = 29%, signal = 101% |
| SARRIO_EPITHELIAL_MESENCHYMAL_TRANSITION_UP | 15 | −0.73215 | −2.13413 | 0 | 4.61E-04 | 0.029 | 5555 | tags = 93%, list = 25%, signal = 125% |
| KEGG_HOMOLOGOUS_RECOMBINATION | 26 | −0.65195 | −2.13209 | 0 | 4.71E-04 | 0.03 | 4302 | tags = 54%, list = 20%, signal = 67% |
| REACTOME_TRANSPORT_OF_RIBONUCLEOPROTEINS_INTO_THE_HOST_NUCLEUS | 29 | −0.62504 | −2.12057 | 0 | 5.88E-04 | 0.038 | 7635 | tags = 83%, list = 35%, signal = 127% |
| REACTOME_TRANSCRIPTION_COUPLED_NER | 44 | −0.55892 | −2.11943 | 0 | 5.82E-04 | 0.038 | 8892 | tags = 86%, list = 41%, signal = 145% |
| REACTOME_NUCLEAR_IMPORT_OF_REV_PROTEIN | 30 | −0.63441 | −2.11724 | 0 | 5.77E-04 | 0.038 | 7635 | tags = 87%, list = 35%, signal = 133% |
| KAUFFMANN_DNA_REPLICATION_GENES | 122 | −0.46254 | −2.11386 | 0 | 6.28E-04 | 0.042 | 6879 | tags = 54%, list = 31%, signal = 78% |
| MITSIADES_RESPONSE_TO_APLIDIN_DN | 203 | −0.4327 | −2.11313 | 0 | 6.22E-04 | 0.042 | 6448 | tags = 51%, list = 29%, signal = 71% |
| MOOTHA_HUMAN_MITODB_6_2002 | 390 | −0.40354 | −2.11231 | 0 | 6.17E-04 | 0.042 | 6758 | tags = 46%, list = 31%, signal = 66% |
| REACTOME_PROCESSING_OF_CAPPED_INTRON_CONTAINING_PRE_MRNA | 112 | −0.48203 | −2.11184 | 0 | 6.11E-04 | 0.042 | 7635 | tags = 64%, list = 35%, signal = 98% |
| PENG_GLUTAMINE_DEPRIVATION_DN | 70 | −0.51196 | −2.11181 | 0 | 6.05E-04 | 0.042 | 6354 | tags = 59%, list = 29%, signal = 82% |
| REACTOME_HIV1_TRANSCRIPTION_INITIATION | 39 | −0.57113 | −2.1081 | 0 | 6.28E-04 | 0.044 | 8247 | tags = 79%, list = 38%, signal = 127% |
| RHODES_UNDIFFERENTIATED_CANCER | 57 | −0.52455 | −2.10806 | 0 | 6.22E-04 | 0.044 | 7746 | tags = 67%, list = 35%, signal = 103% |
| TANG_SENESCENCE_TP53_TARGETS_DN | 35 | −0.57539 | −2.10783 | 0 | 6.17E-04 | 0.044 | 5348 | tags = 63%, list = 24%, signal = 83% |
| BIOCARTA_ATRBRCA_PATHWAY | 20 | −0.67215 | −2.10398 | 0 | 6.38E-04 | 0.046 | 5247 | tags = 70%, list = 24%, signal = 92% |
| MORI_LARGE_PRE_BII_LYMPHOCYTE_UP | 53 | −0.54205 | −2.10142 | 0 | 6.47E-04 | 0.047 | 7289 | tags = 72%, list = 33%, signal = 107% |
| TIEN_INTESTINE_PROBIOTICS_24HR_UP | 455 | −0.39298 | −2.0885 | 0 | 8.14E-04 | 0.058 | 7207 | tags = 53%, list = 33%, signal = 77% |
| KEGG_BASAL_TRANSCRIPTION_FACTORS | 31 | −0.59988 | −2.08011 | 0 | 8.59E-04 | 0.062 | 5796 | tags = 68%, list = 26%, signal = 92% |
| PODAR_RESPONSE_TO_ADAPHOSTIN_DN | 16 | −0.7055 | −2.07696 | 0 | 9.04E-04 | 0.065 | 3479 | tags = 63%, list = 16%, signal = 74% |
| REACTOME_REGULATION_OF_GLUCOKINASE_BY_GLUCOKINASE_REGULATORY_PROTEIN | 29 | −0.60978 | −2.0751 | 0 | 9.22E-04 | 0.067 | 6272 | tags = 72%, list = 29%, signal = 101% |
| AMUNDSON_GAMMA_RADIATION_RESPONSE | 32 | −0.59312 | −2.07276 | 0 | 9.40E-04 | 0.069 | 6032 | tags = 66%, list = 28%, signal = 90% |
| MISSIAGLIA_REGULATED_BY_METHYLATION_DN | 89 | −0.48206 | −2.07014 | 0 | 9.84E-04 | 0.073 | 6873 | tags = 58%, list = 31%, signal = 85% |
| SHAFFER_IRF4_TARGETS_IN_ACTIVATED_B_LYMPHOCYTE | 74 | −0.49013 | −2.06892 | 0 | 9.75E-04 | 0.073 | 4857 | tags = 49%, list = 22%, signal = 62% |
| REACTOME_EXTENSION_OF_TELOMERES | 23 | −0.65295 | −2.066 | 0 | 0.001017 | 0.076 | 5837 | tags = 74%, list = 27%, signal = 101% |
| DIRMEIER_LMP1_RESPONSE_LATE_UP | 42 | −0.5521 | −2.05234 | 0 | 0.001257 | 0.092 | 5294 | tags = 45%, list = 24%, signal = 60% |

TABLE 2-continued

| NAME | SIZE | ES | NES | NOM p-val | FDR q-val | FWER p-val | RANK AT MAX | LEADING EDGE |
|---|---|---|---|---|---|---|---|---|
| KEGG_DNA_REPLICATION | 32 | −0.60017 | −2.05097 | 0 | 0.001259 | 0.093 | 6929 | tags = 72%, list = 32%, signal = 105% |
| GARY_CD5_TARGETS_DN | 341 | −0.39679 | −2.04839 | 0 | 0.001286 | 0.096 | 7114 | tags = 55%, list = 32%, signal = 81% |
| MARSON_FOXP3_TARGETS_DN | 39 | −0.551 | −2.04432 | 0 | 0.001348 | 0.101 | 4412 | tags = 46%, list = 20%, signal = 58% |
| MORI_EMU_MYC_LYMPHOMA_BY_ONSET_TIME_UP | 96 | −0.47001 | −2.04192 | 0 | 0.001362 | 0.103 | 6328 | tags = 55%, list = 29%, signal = 77% |
| GARGALOVIC_RESPONSE_TO_OXIDIZED_PHOSPHOLIPIDS_TURQUOISE_DN | 37 | −0.56283 | −2.03863 | 0 | 0.001422 | 0.109 | 4401 | tags = 59%, list = 20%, signal = 74% |
| KEGG_ASTHMA | 15 | −0.71208 | −2.03735 | 0 | 0.001518 | 0.118 | 1999 | tags = 47%, list = 9%, signal = 51% |
| EGUCHI_CELL_CYCLE_RB1_TARGETS | 18 | −0.68811 | −2.03727 | 0 | 0.001506 | 0.118 | 4559 | tags = 72%, list = 21%, signal = 91% |
| SCHLOSSER_MYC_TARGETS_AND_SERUM_RESPONSE_DN | 40 | −0.55101 | −2.03688 | 0 | 0.001507 | 0.119 | 5731 | tags = 60%, list = 26%, signal = 81% |
| ELVIDGE_HYPOXIA_DN | 117 | −0.45344 | −2.0311 | 0 | 0.001622 | 0.128 | 5371 | tags = 47%, list = 25%, signal = 62% |
| REACTOME_DNA_STRAND_ELONGATION | 26 | −0.62331 | −2.031 | 0.002198 | 0.001622 | 0.129 | 6770 | tags = 77%, list = 31%, signal = 111% |
| REACTOME_TRANSCRIPTION | 140 | −0.43535 | −2.03019 | 0 | 0.001621 | 0.129 | 7557 | tags = 60%, list = 35%, signal = 91% |
| MOOTHA_MITOCHONDRIA | 402 | −0.38548 | −2.02633 | 0 | 0.001758 | 0.141 | 6758 | tags = 46%, list = 31%, signal = 65% |
| DANG_MYC_TARGETS_UP | 109 | −0.45162 | −2.02125 | 0 | 0.001857 | 0.15 | 7245 | tags = 55%, list = 33%, signal = 82% |
| DANG_REGULATED_BY_MYC_UP | 59 | −0.5127 | −2.02065 | 0 | 0.001843 | 0.15 | 6439 | tags = 59%, list = 29%, signal = 84% |
| REACTOME_HOST_INTERACTIONS_OF_HIV_FACTORS | 115 | −0.44796 | −2.01819 | 0 | 0.001851 | 0.152 | 8903 | tags = 68%, list = 41%, signal = 114% |
| ZHANG_RESPONSE_TO_CANTHARIDIN_DN | 49 | −0.52917 | −2.01757 | 0 | 0.001838 | 0.152 | 6558 | tags = 59%, list = 30%, signal = 84% |
| TONG_INTERACT_WITH_PTTG1 | 39 | −0.54688 | −2.01355 | 0 | 0.001933 | 0.159 | 5056 | tags = 49%, list = 23%, signal = 63% |
| BIOCARTA_INFLAM_PATHWAY | 25 | −0.61727 | −2.0126 | 0 | 0.001942 | 0.16 | 1999 | tags = 40%, list = 9%, signal = 44% |
| REACTOME_CDT1_ASSOCIATION_WITH_THE_CDC6_ORC_ORIGIN_COMPLEX | 51 | −0.51868 | −2.0036 | 0 | 0.00208 | 0.173 | 8423 | tags = 73%, list = 38%, signal = 118% |
| KEGG_PYRIMIDINE_METABOLISM | 86 | −0.46227 | −1.99674 | 0 | 0.002332 | 0.19 | 4372 | tags = 44%, list = 20%, signal = 55% |
| RHEIN_ALL_GLUCOCORTICOID_THERAPY_DN | 315 | −0.38684 | −1.99663 | 0 | 0.002316 | 0.19 | 7650 | tags = 54%, list = 35%, signal = 82% |
| BENPORATH_ES_1 | 299 | −0.38787 | −1.9956 | 0 | 0.002343 | 0.193 | 5302 | tags = 41%, list = 24%, signal = 54% |
| LY_AGING_OLD_DN | 43 | −0.53325 | −1.99505 | 0 | 0.002348 | 0.194 | 5064 | tags = 56%, list = 23%, signal = 72% |
| REACTOME_REGULATION_OF_APC_ACTIVATORS_BETWEEN_G1_S_AND_EARLY_ANAPHASE | 67 | −0.48117 | −1.99433 | 0 | 0.002342 | 0.195 | 8903 | tags = 72%, list = 41%, signal = 120% |
| MARTORIATI_MDM4_TARGETS_NEUROEPITHELIUM_UP | 89 | −0.46873 | −1.99372 | 0 | 0.002347 | 0.197 | 4616 | tags = 35%, list = 21%, signal = 44% |

TABLE 2-continued

| NAME | SIZE | ES | NES | NOM p-val | FDR q-val | FWER p-val | RANK AT MAX | LEADING EDGE |
|---|---|---|---|---|---|---|---|---|
| CHIANG_LIVER_CANCER_SUBCLASS_UNANNOTATED_DN | 142 | −0.42418 | −1.99351 | 0 | 0.002352 | 0.199 | 6920 | tags = 49%, list = 32%, signal = 72% |
| REACTOME_CYCLIN_E_ASSOCIATED_EVENTS_DURING_G1_S_TRANSITION | 56 | −0.50105 | −1.99109 | 0 | 0.002428 | 0.208 | 8423 | tags = 70%, list = 38%, signal = 113% |
| CHANG_CYCLING_GENES | 37 | −0.55801 | −1.98899 | 0 | 0.002473 | 0.214 | 4106 | tags = 59%, list = 19%, signal = 73% |
| RICKMAN_METASTASIS_UP | 224 | −0.39927 | −1.97561 | 0 | 0.003032 | 0.258 | 5792 | tags = 42%, list = 26%, signal = 56% |
| DAIRKEE_TERT_TARGETS_UP | 254 | −0.3908 | −1.9717 | 0 | 0.003174 | 0.271 | 5075 | tags = 33%, list = 23%, signal = 42% |
| ZHAN_MULTIPLE_MYELOMA_SUBGROUPS | 26 | −0.60061 | −1.96794 | 0.002353 | 0.003313 | 0.283 | 6794 | tags = 62%, list = 31%, signal = 89% |
| UDAYAKUMAR_MED1_TARGETS_UP | 108 | −0.44358 | −1.96757 | 0 | 0.003312 | 0.285 | 4110 | tags = 38%, list = 19%, signal = 47% |
| BORCZUK_MALIGNANT_MESOTHELIOMA_UP | 258 | −0.39069 | −1.96646 | 0 | 0.003388 | 0.294 | 7491 | tags = 48%, list = 34%, signal = 72% |
| STEIN_ESRRA_TARGETS_RESPONSIVE_TO_ESTROGEN_DN | 36 | −0.54912 | −1.9664 | 0.002242 | 0.003377 | 0.295 | 4568 | tags = 50%, list = 21%, signal = 63% |
| NADERI_BREAST_CANCER_PROGNOSIS_UP | 33 | −0.56192 | −1.96618 | 0 | 0.003365 | 0.296 | 3686 | tags = 52%, list = 17%, signal = 62% |
| MOREAUX_MULTIPLE_MYELOMA_BY_TACI_DN | 102 | −0.44369 | −1.96265 | 0 | 0.003508 | 0.306 | 7245 | tags = 54%, list = 33%, signal = 80% |
| REACTOME_CYTOSOLIC_TRNA_AMINOACYLATION | 18 | −0.65663 | −1.95881 | 0.002132 | 0.003581 | 0.314 | 5918 | tags = 83%, list = 27%, signal = 114% |
| BOYLAN_MULTIPLE_MYELOMA_C_D_UP | 110 | −0.43955 | −1.95861 | 0 | 0.003559 | 0.314 | 6352 | tags = 49%, list = 29%, signal = 69% |
| GRADE_COLON_AND_RECTAL_CANCER_UP | 203 | −0.39763 | −1.95855 | 0 | 0.003537 | 0.314 | 6949 | tags = 50%, list = 32%, signal = 73% |
| FAELT_B_CLL_WITH_VH3_21_UP | 37 | −0.5493 | −1.95553 | 0 | 0.003591 | 0.32 | 6063 | tags = 57%, list = 28%, signal = 78% |
| KEGG_SPLICEOSOME | 92 | −0.44834 | −1.95543 | 0 | 0.003588 | 0.321 | 7655 | tags = 62%, list = 35%, signal = 95% |
| KIM_WT1_TARGETS_DN | 359 | −0.37271 | −1.95293 | 0 | 0.003679 | 0.33 | 4941 | tags = 35%, list = 23%, signal = 44% |
| PENG_RAPAMYCIN_RESPONSE_DN | 55 | −0.49874 | −1.94479 | 0 | 0.003932 | 0.35 | 7835 | tags = 65%, list = 36%, signal = 102% |
| GOLDRATH_ANTIGEN_RESPONSE | 329 | −0.3714 | −1.94272 | 0 | 0.004009 | 0.36 | 4135 | tags = 33%, list = 19%, signal = 41% |
| FOURNIER_ACINAR_DEVELOPMENT_LATE_DN | 18 | −0.64974 | −1.9417 | 0.002242 | 0.004049 | 0.364 | 4508 | tags = 56%, list = 21%, signal = 70% |
| REACTOME_GENE_EXPRESSION | 333 | −0.37499 | −1.9391 | 0 | 0.004245 | 0.378 | 7581 | tags = 49%, list = 35%, signal = 74% |
| SMITH_TERT_TARGETS_UP | 117 | −0.42979 | −1.9385 | 0 | 0.004229 | 0.378 | 5561 | tags = 41%, list = 25%, signal = 55% |
| REACTOME_RNA_POLYMERASE_III_TRANSCRIPTION_INITIATION | 27 | −0.57971 | −1.93649 | 0 | 0.00432 | 0.385 | 7276 | tags = 85%, list = 33%, signal = 127% |
| WEST_ADRENOCORTICAL_TUMOR_UP | 251 | −0.38353 | −1.9344 | 0 | 0.004402 | 0.392 | 6315 | tags = 46%, list = 29%, signal = 64% |
| MONNIER_POSTRADIATION_TUMOR_ESCAPE_UP | 347 | −0.37413 | −1.93378 | 0 | 0.004395 | 0.393 | 5548 | tags = 43%, list = 25%, signal = 56% |

TABLE 2-continued

| NAME | SIZE | ES | NES | NOM p-val | FDR q-val | FWER p-val | RANK AT MAX | LEADING EDGE |
|---|---|---|---|---|---|---|---|---|
| REACTOME_ELONGATION_AND_PROCESSING_OF_CAPPED_TRANSCRIPTS | 106 | -0.4328 | -1.93342 | 0 | 0.004388 | 0.395 | 9169 | tags = 74%, list = 42%, signal = 126% |
| REACTOME_SCF_SKP2_MEDIATED_DEGRADATION_OF_P27_P21 | 50 | -0.50927 | -1.93218 | 0 | 0.004389 | 0.398 | 8903 | tags = 76%, list = 41%, signal = 128% |
| REACTOME_HIV1_TRANSCRIPTION_ELONGATION | 38 | -0.53048 | -1.93192 | 0 | 0.004399 | 0.401 | 8812 | tags = 79%, list = 40%, signal = 132% |
| POMEROY_MEDULLOBLASTOMA_PROGNOSIS_DN | 37 | -0.53422 | -1.93093 | 0.002433 | 0.004427 | 0.403 | 4941 | tags = 38%, list = 23%, signal = 49% |
| MOREAUX_B_LYMPHOCYTE_MATURATION_BY_TACI_DN | 33 | -0.54589 | -1.93023 | 0 | 0.004427 | 0.404 | 7463 | tags = 73%, list = 34%, signal = 110% |
| KEGG_ALLOGRAFT_REJECTION | 16 | -0.66098 | -1.92958 | 0 | 0.004412 | 0.405 | 1560 | tags = 44%, list = 7%, signal = 47% |
| REACTOME_RNA_POLYMERASE_III_TRANSCRIPTION_INITIATION_FROM_TYPE_2_PROMOTER | 19 | -0.6396 | -1.92587 | 0 | 0.004549 | 0.412 | 6903 | tags = 84%, list = 32%, signal = 123% |
| REACTOME_INFLUENZA_LIFE_CYCLE | 120 | -0.42562 | -1.92572 | 0 | 0.004533 | 0.413 | 7779 | tags = 37%, list = 36%, signal = 57% |
| REACTOME_GLUCOSE_TRANSPORT | 38 | -0.53865 | -1.92421 | 0 | 0.004568 | 0.416 | 6272 | tags = 66%, list = 29%, signal = 92% |
| LASTOWSKA_NEUROBLASTOMA_COPY_NUMBER_UP | 138 | -0.41264 | -1.92201 | 0 | 0.004635 | 0.425 | 6262 | tags = 48%, list = 29%, signal = 67% |
| SCIAN_CELL_CYCLE_TARGETS_OF_TP53_AND_TP73_DN | 22 | -0.61497 | -1.92181 | 0 | 0.004627 | 0.426 | 6653 | tags = 77%, list = 30%, signal = 111% |
| JAIN_NFKB_SIGNALING | 64 | -0.48498 | -1.92171 | 0 | 0.004602 | 0.426 | 5141 | tags = 44%, list = 23%, signal = 57% |
| HORIUCHI_WTAP_TARGETS_DN | 244 | -0.38519 | -1.92097 | 0 | 0.00461 | 0.428 | 6174 | tags = 50%, list = 28%, signal = 68% |
| LY_AGING_MIDDLE_DN | 15 | -0.67338 | -1.91334 | 0 | 0.005071 | 0.456 | 4941 | tags = 73%, list = 23%, signal = 95% |
| BERENJENO_TRANSFORMED_BY_RHOA_FOREVER_DN | 29 | -0.55886 | -1.90259 | 0 | 0.005696 | 0.496 | 3614 | tags = 38%, list = 17%, signal = 45% |
| BLUM_RESPONSE_TO_SALIRASIB_UP | 211 | -0.38676 | -1.90016 | 0 | 0.005837 | 0.508 | 3107 | tags = 26%, list = 14%, signal = 30% |
| MARITORIATI_MDM4_TARGETS_FETAL_LIVER_UP | 91 | -0.43519 | -1.89764 | 0 | 0.005936 | 0.515 | 3944 | tags = 31%, list = 18%, signal = 37% |
| REACTOME_DOUBLE_STRAND_BREAK_REPAIR | 20 | -0.62559 | -1.89719 | 0.004255 | 0.005929 | 0.516 | 5837 | tags = 70%, list = 27%, signal = 95% |
| KIM_GASTRIC_CANCER_CHEMOSENSITIVITY | 78 | -0.44364 | -1.89423 | 0 | 0.006027 | 0.522 | 3650 | tags = 38%, list = 17%, signal = 46% |
| SCHLOSSER_MYC_AND_SERUM_RESPONSE_SYNERGY | 29 | -0.54597 | -1.88921 | 0 | 0.006411 | 0.546 | 4807 | tags = 48%, list = 22%, signal = 62% |
| REACTOME_DUAL_INCISION_REACTION_IN_TC_NER | 28 | -0.55454 | -1.88646 | 0 | 0.006559 | 0.556 | 8812 | tags = 86%, list = 40%, signal = 143% |
| RICKMAN_TUMOR_DIFFERENTIATED_MODERATELY_VS_POORLY_DN | 31 | -0.53885 | -1.87914 | 0 | 0.006947 | 0.577 | 5365 | tags = 58%, list = 25%, signal = 77% |
| WONG_MITOCHONDRIA_GENE_MODULE | 199 | -0.38573 | -1.87702 | 0 | 0.007099 | 0.587 | 7076 | tags = 44%, list = 32%, signal = 64% |
| MARTINEZ_RESPONSE_TO_TRABECTEDIN_DN | 194 | -0.38764 | -1.87447 | 0 | 0.00732 | 0.603 | 7218 | tags = 45%, list = 33%, signal = 66% |
| DAZARD_UV_RESPONSE_CLUSTER_G2 | 17 | -0.6373 | -1.87043 | 0 | 0.007678 | 0.624 | 3340 | tags = 53%, list = 15%, signal = 62% |

TABLE 2-continued

| NAME | SIZE | ES | NES | NOM p-val | FDR q-val | FWER p-val | RANK AT MAX | LEADING EDGE |
|---|---|---|---|---|---|---|---|---|
| BIOCARTA_ATM_PATHWAY | 19 | -0.61513 | -1.86847 | 0 | 0.007825 | 0.636 | 4235 | tags = 53%, list = 19%, signal = 65% |
| RAMALHO_STEMNESS_UP | 185 | -0.3878 | -1.86734 | 0 | 0.00787 | 0.641 | 6413 | tags = 49%, list = 29%, signal = 68% |
| REACTOME_CDC20_PHOSPHO_APC_MEDIATED_DEGRADATION_OF_CYCLIN_A | 60 | -0.46466 | -1.8658 | 0 | 0.007931 | 0.644 | 8446 | tags = 65%, list = 39%, signal = 106% |
| RICKMAN_TUMOR_DIFFERENTIATED_MODERATELY_VS_POORLY_UP | 31 | -0.53885 | -1.86463 | 0 | 0.008065 | 0.655 | 5365 | tags = 58%, list = 25%, signal = 77% |
| REACTOME_FORMATION_OF_THE_EARLY_ELONGATION_COMPLEX | 29 | -0.54611 | -1.86136 | 0.002342 | 0.008358 | 0.668 | 8812 | tags = 83%, list = 40%, signal = 138% |
| FARMER_BREAST_CANCER_CLUSTER_2 | 29 | -0.54068 | -1.85871 | 0.006757 | 0.00861 | 0.677 | 6868 | tags = 76%, list = 31%, signal = 110% |
| KEGG_CELL_CYCLE | 117 | -0.4118 | -1.85676 | 0 | 0.008755 | 0.685 | 6324 | tags = 46%, list = 29%, signal = 65% |
| REACTOME_LAGGING_STRAND_SYNTHESIS | 18 | -0.61461 | -1.85531 | 0.002288 | 0.008883 | 0.696 | 5837 | tags = 67%, list = 27%, signal = 91% |
| BIOCARTA_G2_PATHWAY | 23 | -0.58922 | -1.85412 | 0.002198 | 0.008988 | 0.704 | 2092 | tags = 39%, list = 10%, signal = 43% |
| VERNELL_RETINOBLASTOMA_PATHWAY_UP | 35 | -0.51946 | -1.85328 | 0 | 0.009063 | 0.709 | 4507 | tags = 46%, list = 21%, signal = 57% |
| KEGG_RNA_POLYMERASE | 25 | -0.57055 | -1.85044 | 0.006711 | 0.009299 | 0.719 | 8812 | tags = 88%, list = 40%, signal = 147% |
| REACTOME_SCF_BETA_TRCP_MEDIATED_DEGRADATION_OF_EMI1 | 46 | -0.48745 | -1.85016 | 0.002347 | 0.009277 | 0.72 | 8903 | tags = 74%, list = 41%, signal = 124% |
| REACTOME_RNA_POL_II_CTD_PHOSPHORYLATION_AND_INTERACTION_WITH_CE | 26 | -0.55486 | -1.84559 | 0.002247 | 0.009719 | 0.736 | 8812 | tags = 85%, list = 40%, signal = 141% |
| REACTOME_NUCLEOTIDE_EXCISION_REPAIR | 49 | -0.47111 | -1.84298 | 0 | 0.009977 | 0.751 | 5861 | tags = 53%, list = 27%, signal = 72% |
| KOKKINAKIS_METHIONINE_DEPRIVATION_48HR_DN | 58 | -0.46731 | -1.84273 | 0 | 0.009966 | 0.753 | 1826 | tags = 21%, list = 8%, signal = 23% |
| REACTOME_PHOSPHOLIPASE_CMEDIATED_CASCADE | 22 | -0.56055 | -1.83603 | 0 | 0.010787 | 0.791 | 2299 | tags = 32%, list = 11%, signal = 36% |
| LINDGREN_BLADDER_CANCER_CLUSTER_1_DN | 307 | -0.35516 | -1.83076 | 0 | 0.011328 | 0.801 | 6296 | tags = 45%, list = 29%, signal = 62% |
| CHANG_CORE_SERUM_RESPONSE_UP | 56 | -0.46454 | -1.82947 | 0.002315 | 0.011397 | 0.807 | 4678 | tags = 39%, list = 21%, signal = 50% |
| REACTOME_CHOLESTEROL_BIOSYNTHESIS | 20 | -0.5839 | -1.82928 | 0.002183 | 0.011366 | 0.808 | 5072 | tags = 55%, list = 23%, signal = 72% |
| ROYLANCE_BREAST_CANCER_16Q_COPY_NUMBER_UP | 29 | -0.53691 | -1.82878 | 0.004577 | 0.01137 | 0.81 | 4716 | tags = 48%, list = 22%, signal = 61% |
| BENPORATH_ES_2 | 27 | -0.55087 | -1.81839 | 0.004484 | 0.01288 | 0.856 | 5302 | tags = 59%, list = 24%, signal = 78% |
| AMIT_EGF_RESPONSE_120_HELA | 55 | -0.46762 | -1.81837 | 0 | 0.012822 | 0.856 | 4950 | tags = 42%, list = 23%, signal = 54% |
| COLDREN_GEFITINIB_RESISTANCE_UP | 59 | -0.45676 | -1.81786 | 0 | 0.012833 | 0.859 | 5037 | tags = 49%, list = 23%, signal = 64% |
| TIAN_TNF_SIGNALING_VIA_NFKB | 20 | -0.59467 | -1.81746 | 0.008584 | 0.012824 | 0.86 | 2350 | tags = 30%, list = 11%, signal = 34% |
| REACTOME_P53_INDEPENDENT_DNA_DAMAGE_RESPONSE | 42 | -0.47587 | -1.80875 | 0.006993 | 0.013778 | 0.877 | 8903 | tags = 71%, list = 41%, signal = 120% |

TABLE 2-continued

| NAME | SIZE | ES | NES | NOM p-val | FDR q-val | FWER p-val | RANK AT MAX | LEADING EDGE |
|---|---|---|---|---|---|---|---|---|
| MOREIRA_RESPONSE_TO_TSA_UP | 26 | −0.54433 | −1.80792 | 0 | 0.013807 | 0.879 | 8222 | tags = 73%, list = 38%, signal = 117% |
| PUJANA_BREAST_CANCER_LIT_INT_NETWORK | 93 | −0.42623 | −1.80673 | 0 | 0.013938 | 0.883 | 5554 | tags = 45%, list = 25%, signal = 60% |
| BONOME_OVARIAN_CANCER_POOR_SURVIVAL_DN | 15 | −0.63225 | −1.80075 | 0.004494 | 0.014705 | 0.895 | 4297 | tags = 47%, list = 20%, signal = 58% |
| REACTOME_FGFR_LIGAND_BINDING_AND_ACTIVATION | 26 | −0.54964 | −1.80033 | 0.002141 | 0.014709 | 0.896 | 2299 | tags = 31%, list = 11%, signal = 34% |
| REACTOME_SIGNALING_BY_WNT | 56 | −0.45072 | −1.79818 | 0 | 0.015068 | 0.902 | 8903 | tags = 63%, list = 41%, signal = 105% |
| SENGUPTA_NASOPHARYNGEAL_CARCINOMA_UP | 212 | −0.37124 | −1.79813 | 0 | 0.015003 | 0.902 | 5102 | tags = 42%, list = 23%, signal = 54% |
| REACTOME_RNA_POLYMERASE_III_TRANSCRIPTION_INITIATION_FROM_TYPE_3_PROMOTER | 20 | −0.58695 | −1.79724 | 0.002247 | 0.015046 | 0.904 | 5861 | tags = 75%, list = 27%, signal = 102% |
| HOFMANN_CELL_LYMPHOMA_UP | 35 | −0.51003 | −1.79645 | 0 | 0.015047 | 0.904 | 5796 | tags = 51%, list = 26%, signal = 70% |
| REACTOME_TAT_MEDIATED_HIV1_ELONGATION_ARREST_AND_RECOVERY | 28 | −0.53564 | −1.79353 | 0.002179 | 0.015392 | 0.912 | 8812 | tags = 79%, list = 40%, signal = 131% |
| REACTOME_E2F_MEDIATED_REGULATION_OF_DNA_REPLICATION | 29 | −0.53228 | −1.7906 | 0 | 0.015682 | 0.918 | 3495 | tags = 52%, list = 16%, signal = 61% |
| IVANOVA_HEMATOPOIESIS_EARLY_PROGENITOR | 104 | −0.40837 | −1.7891 | 0 | 0.015873 | 0.919 | 5399 | tags = 43%, list = 25%, signal = 57% |
| ELVIDGE_HIF1A_AND_HIF2A_TARGETS_UP | 33 | −0.51171 | −1.78889 | 0 | 0.015819 | 0.919 | 4163 | tags = 45%, list = 19%, signal = 56% |
| KEGG_NUCLEOTIDE_EXCISION_REPAIR | 43 | −0.47622 | −1.78586 | 0.002342 | 0.01618 | 0.922 | 5837 | tags = 51%, list = 27%, signal = 70% |
| RICKMAN_TUMOR_DIFFERENTIATED_WELL_VS_MODERATELY_DN | 84 | −0.41982 | −1.78206 | 0 | 0.016747 | 0.929 | 2380 | tags = 26%, list = 11%, signal = 29% |
| REACTOME_RNA_POLYMERASE_I_TRANSCRIPTION_INITIATION | 21 | −0.56692 | −1.78095 | 0.006787 | 0.016864 | 0.929 | 3988 | tags = 43%, list = 18%, signal = 52% |
| NAKAYAMA_SOFT_TISSUE_TUMORS_PCA2_UP | 75 | −0.43046 | −1.78083 | 0 | 0.016807 | 0.929 | 5413 | tags = 51%, list = 25%, signal = 67% |
| YAO_TEMPORAL_RESPONSE_TO_PROGESTERONE_CLUSTER_16 | 70 | −0.42897 | −1.77415 | 0 | 0.018068 | 0.942 | 6043 | tags = 53%, list = 28%, signal = 73% |
| HOFFMANN_IMMATURE_TO_MATURE_B_LYMPHOCYTE_DN | 27 | −0.53522 | −1.77305 | 0.002174 | 0.018146 | 0.943 | 2076 | tags = 33%, list = 9%, signal = 37% |
| KEGG_PROTEASOME | 42 | −0.47505 | −1.77153 | 0 | 0.018324 | 0.947 | 8666 | tags = 69%, list = 40%, signal = 114% |
| REACTOME_MRNA_3_END_PROCESSING | 30 | −0.52256 | −1.77128 | 0.006356 | 0.018337 | 0.947 | 9277 | tags = 83%, list = 42%, signal = 144% |
| REACTOME_MICRORNA_BIOGENESIS | 18 | −0.58374 | −1.77095 | 0.004184 | 0.018324 | 0.947 | 8812 | tags = 94%, list = 40%, signal = 158% |
| ELVIDGE_HIF1A_TARGETS_UP | 51 | −0.46192 | −1.77012 | 0 | 0.018407 | 0.95 | 4807 | tags = 47%, list = 22%, signal = 60% |
| REACTOME_TELOMERE_MAINTENANCE | 35 | −0.49494 | −1.76955 | 0.002309 | 0.018463 | 0.95 | 5837 | tags = 63%, list = 27%, signal = 86% |
| GARGALOVIC_RESPONSE_TO_OXIDIZED_PHOSPHOLIPIDS_BLUE_UP | 88 | −0.40513 | −1.76935 | 0 | 0.018438 | 0.951 | 5516 | tags = 41%, list = 25%, signal = 54% |
| BRUECKNER_TARGETS_OF_MIRLET7A3_DN | 58 | −0.44814 | −1.76909 | 0 | 0.018383 | 0.951 | 4542 | tags = 33%, list = 21%, signal = 41% |

TABLE 2-continued

| NAME | SIZE | ES | NES | NOM p-val | FDR q-val | FWER p-val | RANK AT MAX | LEADING EDGE |
|---|---|---|---|---|---|---|---|---|
| HENDRICKS_SMARCA4_TARGETS_UP | 37 | −0.49018 | −1.76748 | 0 | 0.018566 | 0.953 | 3413 | tags = 32%, list = 16%, signal = 38% |
| KEGG_BASE_EXCISION_REPAIR | 31 | −0.51872 | −1.76719 | 0.007407 | 0.01856 | 0.953 | 5913 | tags = 58%, list = 27%, signal = 79% |
| ELVIDGE_HYPOXIA_BY_DMOG_DN | 48 | −0.45245 | −1.76658 | 0.002387 | 0.018647 | 0.955 | 4662 | tags = 46%, list = 21%, signal = 58% |
| KRIGE_AMINO_ACID_DEPRIVATION | 24 | −0.53613 | −1.75146 | 0.002203 | 0.021451 | 0.971 | 2795 | tags = 38%, list = 13%, signal = 43% |
| GRAHAM_CML_QUIESCENT_VS_CML_DIVIDING_UP | 18 | −0.59264 | −1.75123 | 0.004376 | 0.021433 | 0.971 | 3128 | tags = 44%, list = 14%, signal = 52% |
| REACTOME_MRNA_SPLICING | 81 | −0.42193 | −1.75088 | 0 | 0.021433 | 0.971 | 9158 | tags = 75%, list = 42%, signal = 129% |
| SCIBETTA_KDM5B_TARGETS_DN | 62 | −0.4322 | −1.74733 | 0.00232 | 0.021984 | 0.974 | 6859 | tags = 60%, list = 31%, signal = 87% |
| WEST_ADRENOCORTICAL_TUMOR_MARKERS_UP | 19 | −0.57446 | −1.74619 | 0.004525 | 0.022091 | 0.975 | 6004 | tags = 79%, list = 27%, signal = 109% |
| NAGASHIMA_EGF_SIGNALING_UP | 51 | −0.4524 | −1.74565 | 0.002326 | 0.022148 | 0.975 | 4328 | tags = 41%, list = 20%, signal = 51% |
| LY_AGING_PREMATURE_DN | 22 | −0.54918 | −1.74559 | 0.006303 | 0.02208 | 0.975 | 5064 | tags = 55%, list = 23%, signal = 71% |
| REACTOME_VIF_MEDIATED_DEGRADATION_OF_APOBEC3G | 45 | −0.45878 | −1.74448 | 0.002273 | 0.02225 | 0.975 | 8903 | tags = 69%, list = 41%, signal = 116% |
| WANG_SMARCE1_TARGETS_DN | 268 | −0.34773 | −1.74421 | 0 | 0.022213 | 0.975 | 4223 | tags = 29%, list = 19%, signal = 35% |
| REACTOME_RNA_POLYMERASE_I_III_AND_MITOCHONDRIAL_TRANSCRIPTION | 69 | −0.42423 | −1.74093 | 0 | 0.022727 | 0.978 | 6005 | tags = 52%, list = 27%, signal = 72% |
| BUYTAERT_PHOTODYNAMIC_THERAPY_STRESS_DN | 485 | −0.32386 | −1.74085 | 0 | 0.022653 | 0.978 | 5555 | tags = 36%, list = 25%, signal = 47% |
| BROWNE_HCMV_INFECTION_24HR_UP | 133 | −0.37862 | −1.74079 | 0 | 0.022578 | 0.978 | 6153 | tags = 46%, list = 28%, signal = 63% |
| REACTOME_SHCMEDIATED_CASCADE | 21 | −0.55619 | −1.74072 | 0.00883 | 0.022505 | 0.978 | 2299 | tags = 29%, list = 11%, signal = 32% |
| BIOCARTA_SPRY_PATHWAY | 18 | −0.57942 | −1.74034 | 0.006623 | 0.022501 | 0.978 | 1759 | tags = 28%, list = 8%, signal = 30% |
| REACTOME_ABORTIVE_ELONGATION_OF_HIV1_TRANSCRIPT_IN_THE_ABSENCE_OF_TAT | 20 | −0.5675 | −1.74029 | 0.013575 | 0.022422 | 0.978 | 9169 | tags = 90%, list = 42%, signal = 155% |
| KEGG_MISMATCH_REPAIR | 22 | −0.55825 | −1.73989 | 0.006522 | 0.022408 | 0.978 | 8892 | tags = 86%, list = 41%, signal = 145% |
| REACTOME_BASE_EXCISION_REPAIR | 16 | −0.59901 | −1.73733 | 0.011287 | 0.022865 | 0.979 | 6552 | tags = 69%, list = 30%, signal = 98% |
| DOANE_BREAST_CANCER_CLASSES_DN | 29 | −0.50954 | −1.73694 | 0.006579 | 0.022861 | 0.98 | 2768 | tags = 28%, list = 13%, signal = 32% |
| LIU_SOX4_TARGETS_DN | 241 | −0.3473 | −1.7365 | 0 | 0.022884 | 0.982 | 6368 | tags = 39%, list = 29%, signal = 54% |
| BOYLAN_MULTIPLE_MYELOMA_D_UP | 83 | −0.4079 | −1.73612 | 0 | 0.022886 | 0.982 | 5005 | tags = 40%, list = 23%, signal = 51% |
| ZHANG_RESPONSE_TO_IKK_INHIBITOR_AND_TNF_DN | 69 | −0.41797 | −1.73513 | 0.005249 | 0.023017 | 0.983 | 2419 | tags = 29%, list = 11%, signal = 32% |
| SHIPP_DLBCL_VS_FOLLICULAR_LYMPHOMA_UP | 41 | −0.47072 | −1.73454 | 0.008511 | 0.023047 | 0.983 | 7538 | tags = 76%, list = 34%, signal = 115% |

TABLE 2-continued

| NAME | SIZE | ES | NES | NOM p-val | FDR q-val | FWER p-val | RANK AT MAX | LEADING EDGE |
|---|---|---|---|---|---|---|---|---|
| AMIT_EGF_RESPONSE_120_MCF10A | 38 | -0.4803 | -1.7334 | 0.009412 | 0.023187 | 0.983 | 6027 | tags = 53%, list = 28%, signal = 73% |
| BILD_MYC_ONCOGENIC_SIGNATURE | 144 | -0.37447 | -1.73285 | 0 | 0.023232 | 0.983 | 4645 | tags = 42%, list = 21%, signal = 53% |
| SHEPARD_BMYB_TARGETS | 58 | -0.43562 | -1.73142 | 0.004762 | 0.023477 | 0.983 | 6032 | tags = 57%, list = 28%, signal = 78% |
| REACTOME_AUTODEGRADATION_OF_CDH1_BY_CDH1_APC | 55 | -0.44901 | -1.72632 | 0 | 0.024594 | 0.988 | 8446 | tags = 64%, list = 39%, signal = 103% |
| REACTOME_STABILIZATION_OF_P53 | 45 | -0.45328 | -1.72463 | 0.00232 | 0.02485 | 0.988 | 9592 | tags = 76%, list = 44%, signal = 134% |
| NAGASHIMA_NRG1_SIGNALING_UP | 151 | -0.36805 | -1.72373 | 0 | 0.024899 | 0.988 | 3705 | tags = 31%, list = 17%, signal = 37% |
| KANNAN_TP53_TARGETS_DN | 15 | -0.60828 | -1.72134 | 0.010593 | 0.025342 | 0.988 | 3065 | tags = 40%, list = 14%, signal = 46% |
| PAL_PRMT5_TARGETS_UP | 183 | -0.35915 | -1.72133 | 0 | 0.025257 | 0.988 | 6733 | tags = 49%, list = 31%, signal = 70% |
| CHEN_HOXA5_TARGETS_9HR_DN | 35 | -0.4805 | -1.72092 | 0.002203 | 0.02525 | 0.988 | 5285 | tags = 46%, list = 24%, signal = 60% |
| CHEOK_RESPONSE_TO_MERCAPTOPURINE_AND_HD_MTX_DN | 21 | -0.56181 | -1.71985 | 0.008696 | 0.025352 | 0.989 | 5476 | tags = 43%, list = 25%, signal = 57% |
| BHATT_G2M_ARREST_BY_2METHOXYESTRADIOL_UP | 92 | -0.40056 | -1.71724 | 0.002577 | 0.025853 | 0.989 | 6433 | tags = 47%, list = 29%, signal = 66% |
| REACTOME_REPAIR_SYNTHESIS_OF_PATCH_27_30_BASES_LONG_BY_DNA_POLYMERASE | 15 | -0.60537 | -1.71296 | 0.01559 | 0.026861 | 0.991 | 5554 | tags = 60%, list = 25%, signal = 80% |
| REACTOME_RNA_POLYMERASE_I_PROMOTER_ESCAPE | 18 | -0.56795 | -1.70974 | 0.008909 | 0.027568 | 0.993 | 3988 | tags = 44%, list = 18%, signal = 54% |
| KEGG_GALACTOSE_METABOLISM | 25 | -0.52012 | -1.70892 | 0.00907 | 0.02767 | 0.993 | 4099 | tags = 40%, list = 19%, signal = 49% |
| BOYLAN_MULTIPLE_MYELOMA_C_CLUSTER_UP | 29 | -0.50959 | -1.70656 | 0.008969 | 0.028226 | 0.993 | 2991 | tags = 41%, list = 14%, signal = 48% |
| LEE_METASTASIS_AND_RNA_PROCESSING_UP | 15 | -0.58996 | -1.70655 | 0.022936 | 0.028129 | 0.993 | 8075 | tags = 80%, list = 37%, signal = 127% |
| AMIT_SERUM_RESPONSE_480_MCF10A | 30 | -0.49537 | -1.70219 | 0.009009 | 0.029016 | 0.993 | 3413 | tags = 37%, list = 16%, signal = 43% |
| MOOTHA_PGC | 307 | -0.33049 | -1.70183 | 0 | 0.029001 | 0.993 | 7069 | tags = 46%, list = 32%, signal = 67% |
| REACTOME_MRNA_PROCESSING | 30 | -0.49898 | -1.70076 | 0.002494 | 0.029224 | 0.994 | 8812 | tags = 80%, list = 40%, signal = 134% |
| BIOCARTA_DC_PATHWAY | 22 | -0.5261 | -1.6975 | 0.011876 | 0.029891 | 0.994 | 1999 | tags = 32%, list = 9%, signal = 35% |
| WILCOX_RESPONSE_TO_PROGESTERONE_UP | 112 | -0.38162 | -1.69573 | 0 | 0.030222 | 0.994 | 5072 | tags = 45%, list = 23%, signal = 58% |
| BIOCARTA_P53_PATHWAY | 16 | -0.57249 | -1.69552 | 0.010707 | 0.030177 | 0.994 | 4124 | tags = 56%, list = 19%, signal = 69% |
| DAZARD_RESPONSE_TO_UV_SCC_UP | 72 | -0.41147 | -1.69456 | 0 | 0.030338 | 0.994 | 3974 | tags = 32%, list = 18%, signal = 39% |
| GRAHAM_CML_QUIESCENT_VS_NORMAL_QUIESCENT_UP | 72 | -0.40487 | -1.69363 | 0 | 0.030502 | 0.994 | 6001 | tags = 57%, list = 27%, signal = 78% |
| LANDIS_ERBB2_BREAST_TUMORS_324_UP | 139 | -0.36646 | -1.69319 | 0 | 0.030545 | 0.994 | 4710 | tags = 34%, list = 22%, signal = 43% |

TABLE 2-continued

| NAME | SIZE | ES | NES | NOM p-val | FDR q-val | FWER p-val | RANK AT MAX | LEADING EDGE |
|---|---|---|---|---|---|---|---|---|
| CHIARADONNA_NEOPLASTIC_TRANSFORMATION_KRAS_UP | 119 | −0.37042 | −1.69273 | 0 | 0.030552 | 0.994 | 5970 | tags = 45%, list = 27%, signal = 62% |
| KEGG_ONE_CARBON_POOL_BY_FOLATE | 15 | −0.59992 | −1.69119 | 0.018947 | 0.030866 | 0.996 | 4791 | tags = 73%, list = 22%, signal = 94% |
| DOUGLAS_BMI1_TARGETS_UP | 442 | −0.31592 | −1.68759 | 0 | 0.031609 | 0.996 | 4215 | tags = 29%, list = 19%, signal = 35% |
| OLSSON_E2F3_TARGETS_DN | 22 | −0.53086 | −1.68742 | 0.011737 | 0.03154 | 0.996 | 4086 | tags = 50%, list = 19%, signal = 61% |
| WILLIAMS_ESR1_TARGETS_UP | 19 | −0.55372 | −1.68326 | 0.010504 | 0.032535 | 0.999 | 4662 | tags = 47%, list = 21%, signal = 60% |
| PENG_LEUCINE_DEPRIVATION_DN | 41 | −0.45777 | −1.681 | 0.009153 | 0.033002 | 0.999 | 8257 | tags = 68%, list = 38%, signal = 109% |
| KEGG_FC_EPSILON_RI_SIGNALING_PATHWAY | 76 | −0.40196 | −1.68074 | 0.002577 | 0.03295 | 0.999 | 1999 | tags = 14%, list = 9%, signal = 16% |
| RHODES_CANCER_META_SIGNATURE | 52 | −0.43623 | −1.67879 | 0.004926 | 0.033501 | 0.999 | 8353 | tags = 65%, list = 38%, signal = 105% |
| BROWNE_HCMV_INFECTION_14HR_UP | 123 | −0.36371 | −1.67858 | 0 | 0.033458 | 0.999 | 6904 | tags = 49%, list = 32%, signal = 71% |
| SPIELMAN_LYMPHOBLAST_EUROPEAN_VS_ASIAN_UP | 406 | −0.3221 | −1.6748 | 0 | 0.034351 | 0.999 | 6365 | tags = 38%, list = 29%, signal = 53% |
| DIRMEIER_LMP1_RESPONSE_EARLY | 49 | −0.43597 | −1.67219 | 0.00241 | 0.0349 | 0.999 | 5795 | tags = 43%, list = 26%, signal = 58% |
| KEGG_CYTOKINE_CYTOKINE_RECEPTOR_INTERACTION | 202 | −0.34329 | −1.67194 | 0 | 0.034846 | 0.999 | 3494 | tags = 29%, list = 16%, signal = 34% |
| BOYAULT_LIVER_CANCER_SUBCLASS_G12_UP | 35 | −0.47501 | −1.67121 | 0.011628 | 0.034991 | 0.999 | 3831 | tags = 37%, list = 18%, signal = 45% |
| REACTOME_PREFOLDIN_MEDIATED_TRANSFER_OF_SUBSTRATE_TO_CCT_TRIC | 21 | −0.53257 | −1.66687 | 0.013857 | 0.036009 | 0.999 | 7425 | tags = 67%, list = 34%, signal = 101% |
| GINESTIER_BREAST_CANCER_ZNF217_AMPLIFIED_DN | 226 | −0.33501 | −1.66503 | 0 | 0.036448 | 0.999 | 6641 | tags = 39%, list = 30%, signal = 55% |
| REACTOME_EGFR_DOWNREGULATION | 23 | −0.51833 | −1.66296 | 0.020548 | 0.036971 | 0.999 | 5650 | tags = 35%, list = 26%, signal = 47% |
| REACTOME_PYRIMIDINE_METABOLISM | 20 | −0.53158 | −1.66003 | 0.013274 | 0.037713 | 0.999 | 1826 | tags = 40%, list = 8%, signal = 44% |
| VANTVEER_BREAST_CANCER_BRCA1_UP | 25 | −0.51733 | −1.65758 | 0.019313 | 0.038342 | 0.999 | 5293 | tags = 44%, list = 24%, signal = 58% |
| KEGG_GLYCINE_SERINE_AND_THREONINE_METABOLISM | 25 | −0.52385 | −1.65415 | 0.017021 | 0.039205 | 1 | 3223 | tags = 40%, list = 15%, signal = 47% |
| CHAUHAN_RESPONSE_TO_METHOXYESTRADIOL_UP | 44 | −0.4478 | −1.65346 | 0.009174 | 0.03929 | 1 | 7597 | tags = 66%, list = 35%, signal = 101% |
| ACEVEDO_LIVER_CANCER_WITH_H3K9ME3_DN | 57 | −0.41475 | −1.65304 | 0 | 0.039293 | 1 | 5071 | tags = 44%, list = 23%, signal = 57% |
| PARENT_MTOR_SIGNALING_DN | 34 | −0.4655 | −1.65233 | 0.018265 | 0.039453 | 1 | 3138 | tags = 32%, list = 14%, signal = 38% |
| ACEVEDO_NORMAL_TISSUE_ADJACENT_TO_LIVER_TUMOR_DN | 278 | −0.32185 | −1.65157 | 0 | 0.03953 | 1 | 5186 | tags = 31%, list = 24%, signal = 40% |
| AMUNDSON_GENOTOXIC_SIGNATURE | 76 | −0.39026 | −1.64944 | 0.002632 | 0.040202 | 1 | 2400 | tags = 26%, list = 11%, signal = 29% |
| WANG_METHYLATED_IN_BREAST_CANCER | 28 | −0.48962 | −1.64877 | 0.004556 | 0.040307 | 1 | 5766 | tags = 50%, list = 26%, signal = 68% |

TABLE 2-continued

| NAME | SIZE | ES | NES | NOM p-val | FDR q-val | FWER p-val | RANK AT MAX | LEADING EDGE |
|---|---|---|---|---|---|---|---|---|
| SHEPARD_CRUSH_AND_BURN_MUTANT_DN | 138 | −0.36039 | −1.64233 | 0 | 0.042291 | 1 | 6287 | tags = 46%, list = 29%, signal = 65% |
| TONKS_TARGETS_OF_RUNX1_RUNX1T1_FUSION_MONOCYTE_UP | 160 | −0.34785 | −1.64217 | 0 | 0.042209 | 1 | 5564 | tags = 44%, list = 25%, signal = 58% |
| SMIRNOV_CIRCULATING_ENDOTHELIOCYTES_IN_CANCER_UP | 134 | −0.35747 | −1.64134 | 0 | 0.042323 | 1 | 1881 | tags = 22%, list = 9%, signal = 24% |
| GEORGES_CELL_CYCLE_MIR192_TARGETS | 55 | −0.41585 | −1.63727 | 0.009009 | 0.043643 | 1 | 6178 | tags = 51%, list = 28%, signal = 71% |
| VANHARANTA_UTERINE_FIBROID_WITH_7Q_DELETION_UP | 55 | −0.42177 | −1.63642 | 0.005464 | 0.043819 | 1 | 8221 | tags = 60%, list = 38%, signal = 96% |
| DACOSTA_UV_RESPONSE_VIA_ERCC3_UP | 263 | −0.327 | −1.63636 | 0 | 0.043695 | 1 | 6170 | tags = 39%, list = 28%, signal = 54% |
| REACTOME_GLOBAL_GENOMIC_NER | 33 | −0.46089 | −1.63605 | 0.01171 | 0.043666 | 1 | 5837 | tags = 55%, list = 27%, signal = 74% |
| REACTOME_SYNTHESIS_OF_GPI_ANCHORED_PROTEINS | 23 | −0.50984 | −1.63599 | 0.015556 | 0.043558 | 1 | 5332 | tags = 39%, list = 24%, signal = 52% |
| KEGG_PORPHYRIN_AND_CHLOROPHYLL_METABOLISM | 23 | −0.50638 | −1.63489 | 0.013793 | 0.043736 | 1 | 2880 | tags = 39%, list = 13%, signal = 45% |
| TURASHVILI_BREAST_NORMAL_DUCTAL_VS_LOBULAR_UP | 43 | −0.44105 | −1.63472 | 0.002347 | 0.043678 | 1 | 4159 | tags = 30%, list = 19%, signal = 37% |
| HSC_MATURE_FETAL | 21 | −0.52771 | −1.63326 | 0.020548 | 0.044137 | 1 | 6006 | tags = 57%, list = 27%, signal = 79% |
| STEIN_ESRRA_TARGETS_RESPONSIVE_TO_ESTROGEN_UP | 21 | −0.51886 | −1.63258 | 0.027957 | 0.044203 | 1 | 1226 | tags = 33%, list = 6%, signal = 35% |
| SHEPARD_CRUSH_AND_BURN_MUTANT_UP | 125 | −0.35859 | −1.62825 | 0.002755 | 0.045705 | 1 | 4532 | tags = 39%, list = 21%, signal = 49% |
| REACTOME_METABOLISM_OF_VITAMINS_AND_COFACTORS | 40 | −0.44337 | −1.62546 | 0.016129 | 0.046522 | 1 | 3969 | tags = 40%, list = 18%, signal = 49% |
| VANTVEER_BREAST_CANCER_ESR1_DN | 176 | −0.33964 | −1.62501 | 0.00277 | 0.046595 | 1 | 4524 | tags = 31%, list = 21%, signal = 38% |
| REACTOME_METABOLISM_OF_NUCLEOTIDES | 64 | −0.40412 | −1.62145 | 0 | 0.047924 | 1 | 4372 | tags = 42%, list = 20%, signal = 53% |
| SUNG_METASTASIS_STROMA_UP | 89 | −0.37528 | −1.62073 | 0.007895 | 0.048055 | 1 | 5198 | tags = 43%, list = 24%, signal = 56% |
| WEIGEL_OXIDATIVE_STRESS_BY_HNE_AND_H2O2 | 34 | −0.44773 | −1.61991 | 0.009524 | 0.048239 | 1 | 5259 | tags = 32%, list = 24%, signal = 43% |
| BIOCARTA_PROTEASOME_PATHWAY | 18 | −0.54104 | −1.61938 | 0.019523 | 0.048296 | 1 | 9592 | tags = 83%, list = 44%, signal = 148% |
| KEGG_AMINO_SUGAR_AND_NUCLEOTIDE_SUGAR_METABOLISM | 41 | −0.44482 | −1.61843 | 0.015038 | 0.048492 | 1 | 4255 | tags = 37%, list = 19%, signal = 45% |
| PELLICCIOTTA_HDAC_IN_ANTIGEN_PRESENTATION_UP | 57 | −0.40746 | −1.61747 | 0.004751 | 0.048706 | 1 | 8257 | tags = 53%, list = 38%, signal = 84% |
| LANDIS_ERBB2_BREAST_PRENEOPLASTIC_UP | 21 | −0.52713 | −1.61628 | 0.03304 | 0.049018 | 1 | 5507 | tags = 48%, list = 25%, signal = 64% |
| SHEPARD_BMYB_MORPHOLINO_DN | 151 | −0.34543 | −1.61546 | 0 | 0.04917 | 1 | 4797 | tags = 38%, list = 22%, signal = 49% |
| YEGNASUBRAMANIAN_PROSTATE_CANCER | 91 | −0.3681 | −1.61505 | 0.00241 | 0.049198 | 1 | 5394 | tags = 38%, list = 25%, signal = 51% |
| KIM_WT1_TARGETS_UP | 183 | −0.34191 | −1.61475 | 0 | 0.049181 | 1 | 4812 | tags = 33%, list = 22%, signal = 42% |

TABLE 2-continued

| NAME | SIZE | ES | NES | NOM p-val | FDR q-val | FWER p-val | RANK AT MAX | LEADING EDGE |
|---|---|---|---|---|---|---|---|---|
| MOHANKUMAR_TLX1_TARGETS_UP | 325 | −0.31306 | −1.61407 | 0 | 0.049308 | 1 | 5689 | tags = 37%, list = 26%, signal = 49% |
| AMUNDSON_RESPONSE_TO_ARSENITE | 159 | −0.34303 | −1.61281 | 0 | 0.049661 | 1 | 5229 | tags = 31%, list = 24%, signal = 41% |
| KEGG_PANTOTHENATE_AND_COA_BIOSYNTHESIS | 15 | −0.55962 | −1.61174 | 0.034014 | 0.049863 | 1 | 1891 | tags = 27%, list = 9%, signal = 29% |
| KEGG_P53_SIGNALING_PATHWAY | 61 | −0.40197 | −1.60772 | 0.002494 | 0.051363 | 1 | 5516 | tags = 46%, list = 25%, signal = 61% |
| RIZ_ERYTHROID_DIFFERENTIATION_CCNE1 | 38 | −0.44707 | −1.60742 | 0.016827 | 0.051366 | 1 | 4135 | tags = 39%, list = 19%, signal = 49% |
| HAHTOLA_MYCOSIS_FUNGOIDES_CD4_UP | 52 | −0.41002 | −1.60651 | 0.00907 | 0.051599 | 1 | 2819 | tags = 27%, list = 13%, signal = 31% |
| MAHAJAN_RESPONSE_TO_IL1A_DN | 53 | −0.41564 | −1.60627 | 0.006834 | 0.051554 | 1 | 4977 | tags = 34%, list = 23%, signal = 44% |
| KORKOLA_EMBRYONIC_CARCINOMA_VS_SEMINOMA_UP | 19 | −0.52884 | −1.60556 | 0.017131 | 0.051738 | 1 | 2193 | tags = 37%, list = 10%, signal = 41% |
| REACTOME_RNA_POLYMERASE_III_TRANSCRIPTION | 32 | −0.45961 | −1.60364 | 0.013986 | 0.052373 | 1 | 6005 | tags = 66%, list = 27%, signal = 90% |
| KEGG_RNA_DEGRADATION | 50 | −0.42032 | −1.60343 | 0.009153 | 0.052308 | 1 | 7202 | tags = 64%, list = 33%, signal = 95% |
| CHEN_HOXA5_TARGETS_9HR_UP | 157 | −0.33909 | −1.60172 | 0 | 0.052912 | 1 | 6240 | tags = 38%, list = 29%, signal = 53% |
| NAKAMURA_METASTASIS | 35 | −0.45954 | −1.60126 | 0.014563 | 0.052967 | 1 | 4215 | tags = 34%, list = 19%, signal = 42% |
| MORI_MATURE_B_LYMPHOCYTE_DN | 56 | −0.41156 | −1.60091 | 0.00905 | 0.052991 | 1 | 4737 | tags = 41%, list = 22%, signal = 52% |
| REACTOME_METABOLISM_OF_MRNA | 42 | −0.43055 | −1.60047 | 0.009132 | 0.053032 | 1 | 7211 | tags = 60%, list = 33%, signal = 89% |
| KEGG_N_GLYCAN_BIOSYNTHESIS | 40 | −0.4325 | −1.59985 | 0.015801 | 0.053124 | 1 | 6311 | tags = 50%, list = 29%, signal = 70% |
| JEON_SMAD6_TARGETS_DN | 18 | −0.54236 | −1.59558 | 0.026786 | 0.054948 | 1 | 5348 | tags = 50%, list = 24%, signal = 66% |
| CLASPER_LYMPHATIC_VESSELS_DURING_METASTASIS_UP | 17 | −0.55069 | −1.59427 | 0.030568 | 0.055381 | 1 | 2913 | tags = 41%, list = 13%, signal = 47% |
| AMIT_EGF_RESPONSE_480_HELA | 136 | −0.34576 | −1.59203 | 0.002591 | 0.056209 | 1 | 3870 | tags = 29%, list = 18%, signal = 36% |
| THEILGAARD_NEUTROPHIL_AT_SKIN_WOUND_UP | 65 | −0.38845 | −1.59076 | 0.004762 | 0.056647 | 1 | 5493 | tags = 37%, list = 25%, signal = 49% |
| MILL_PSEUDOPODIA_HAPTOTAXIS_UP | 438 | −0.29623 | −1.58848 | 0 | 0.057541 | 1 | 6731 | tags = 38%, list = 31%, signal = 54% |
| KEGG_SELENOAMINO_ACID_METABOLISM | 20 | −0.52272 | −1.5861 | 0.026144 | 0.058513 | 1 | 7217 | tags = 65%, list = 33%, signal = 97% |
| KORKOLA_EMBRYONAL_CARCINOMA_UP | 36 | −0.44176 | −1.58582 | 0.011601 | 0.058493 | 1 | 6328 | tags = 47%, list = 29%, signal = 66% |
| FONTAINE_FOLLICULAR_THYROID_ADENOMA_UP | 57 | −0.40056 | −1.58505 | 0.015345 | 0.058613 | 1 | 3065 | tags = 30%, list = 14%, signal = 35% |
| RIZ_ERYTHROID_DIFFERENTIATION | 71 | −0.38675 | −1.58081 | 0.009592 | 0.060491 | 1 | 4993 | tags = 37%, list = 23%, signal = 47% |
| REACTOME_PYRUVATE_METABOLISM_AND_TCA_CYCLE | 32 | −0.44675 | −1.57427 | 0.021378 | 0.06352 | 1 | 7132 | tags = 53%, list = 33%, signal = 79% |

TABLE 2-continued

| NAME | SIZE | ES | NES | NOM p-val | FDR q-val | FWER p-val | RANK AT MAX | LEADING EDGE |
|---|---|---|---|---|---|---|---|---|
| WANG_RESPONSE_TO_ANDROGEN_UP | 23 | −0.48805 | −1.57297 | 0.024943 | 0.063962 | 1 | 6045 | tags = 61%, list = 28%, signal = 84% |
| KEGG_STEROID_BIOSYNTHESIS | 16 | −0.54002 | −1.57091 | 0.027254 | 0.064832 | 1 | 5329 | tags = 56%, list = 24%, signal = 74% |
| JAEGER_METASTASIS_UP | 37 | −0.43504 | −1.57013 | 0.01087 | 0.065086 | 1 | 3001 | tags = 30%, list = 14%, signal = 34% |
| LEONARD_HYPOXIA | 29 | −0.46322 | −1.56924 | 0.017699 | 0.065355 | 1 | 2233 | tags = 28%, list = 10%, signal = 31% |
| STEIN_ESRRA_TARGETS | 401 | −0.29457 | −1.56577 | 0 | 0.066972 | 1 | 5116 | tags = 30%, list = 23%, signal = 39% |
| JIANG_TIP30_TARGETS_DN | 23 | −0.49545 | −1.56502 | 0.028889 | 0.067216 | 1 | 5302 | tags = 52%, list = 24%, signal = 69% |
| KEGG_AUTOIMMUNE_THYROID_DISEASE | 23 | −0.49272 | −1.56463 | 0.030905 | 0.06723 | 1 | 1694 | tags = 30%, list = 8%, signal = 33% |
| BIOCARTA_INTEGRIN_PATHWAY | 38 | −0.42913 | −1.56369 | 0.014354 | 0.06759 | 1 | 5869 | tags = 32%, list = 27%, signal = 43% |
| CREIGHTON_ENDOCRINE_THERAPY_RESISTANCE_2 | 255 | −0.30936 | −1.56175 | 0 | 0.06838 | 1 | 4105 | tags = 28%, list = 19%, signal = 34% |
| HEDENFALK_BREAST_CANCER_BRCA1_VS_BRCA2 | 25 | −0.47245 | −1.55993 | 0.033097 | 0.069118 | 1 | 3574 | tags = 40%, list = 16%, signal = 48% |
| MAHADEVAN_IMATINIB_RESISTANCE_UP | 16 | −0.54102 | −1.55993 | 0.042827 | 0.068943 | 1 | 3130 | tags = 38%, list = 14%, signal = 44% |
| MUELLER_METHYLATED_IN_GLIOBLASTOMA | 30 | −0.45712 | −1.5577 | 0.020737 | 0.069831 | 1 | 3426 | tags = 40%, list = 16%, signal = 47% |
| BOYAULT_LIVER_CANCER_SUBCLASS_G23_UP | 42 | −0.42862 | −1.5574 | 0.011601 | 0.069814 | 1 | 6673 | tags = 60%, list = 30%, signal = 85% |
| REACTOME_RNA_POLYMERASE_I_PROMOTER_CLEARANCE | 33 | −0.43867 | −1.55657 | 0.021505 | 0.070054 | 1 | 3988 | tags = 36%, list = 18%, signal = 44% |
| BIOCARTA_MCM_PATHWAY | 18 | −0.51775 | −1.55555 | 0.030043 | 0.070423 | 1 | 7652 | tags = 89%, list = 35%, signal = 137% |
| CASTELLANO_NRAS_TARGETS_UP | 66 | −0.37914 | −1.55523 | 0.009662 | 0.070421 | 1 | 1258 | tags = 15%, list = 6%, signal = 16% |
| BILD_E2F3_ONCOGENIC_SIGNATURE | 172 | −0.32638 | −1.55522 | 0 | 0.070248 | 1 | 3202 | tags = 24%, list = 15%, signal = 28% |
| WEINMANN_ADAPTATION_TO_HYPOXIA_DN | 32 | −0.43747 | −1.55424 | 0.032407 | 0.070646 | 1 | 2418 | tags = 38%, list = 11%, signal = 42% |
| KAPOSI_LIVER_CANCER_POOR_SURVIVAL_UP | 16 | −0.54639 | −1.55257 | 0.043573 | 0.071408 | 1 | 4016 | tags = 31%, list = 18%, signal = 38% |
| PASQUALUCCI_LYMPHOMA_BY_GC_STAGE_UP | 246 | −0.31478 | −1.55237 | 0 | 0.071317 | 1 | 3587 | tags = 26%, list = 16%, signal = 30% |
| REACTOME_POST_TRANSLATIONAL_PROTEIN_MODIFICATION | 37 | −0.43412 | −1.55172 | 0.017279 | 0.071446 | 1 | 6520 | tags = 46%, list = 30%, signal = 65% |
| CAFFAREL_RESPONSE_TO_THC_DN | 21 | −0.50052 | −1.5485 | 0.030702 | 0.073139 | 1 | 5819 | tags = 52%, list = 27%, signal = 71% |
| REACTOME_G2_M_TRANSITION | 71 | −0.36948 | −1.5485 | 0.013123 | 0.072959 | 1 | 8210 | tags = 52%, list = 38%, signal = 83% |
| GAJATE_RESPONSE_TO_TRABECTEDIN_DN | 15 | −0.53965 | −1.54414 | 0.046709 | 0.075117 | 1 | 7028 | tags = 67%, list = 32%, signal = 98% |
| STEIN_ESRRA_TARGETS_UP | 298 | −0.3001 | −1.54387 | 0 | 0.075021 | 1 | 4541 | tags = 27%, list = 21%, signal = 33% |

TABLE 2-continued

| NAME | SIZE | ES | NES | NOM p-val | FDR q-val | FWER p-val | RANK AT MAX | LEADING EDGE |
|---|---|---|---|---|---|---|---|---|
| MOOTHA_VOXPHOS | 79 | −0.37294 | −1.54361 | 0.009975 | 0.074979 | 1 | 9439 | tags = 54%, list = 43%, signal = 95% |
| SWEET_KRAS_TARGETS_UP | 17 | −0.52812 | −1.5415 | 0.03397 | 0.075917 | 1 | 3664 | tags = 29%, list = 17%, signal = 35% |
| KERLEY_RESPONSE_TO_CISPLATIN_UP | 35 | −0.43382 | −1.53987 | 0.021028 | 0.076598 | 1 | 1839 | tags = 29%, list = 8%, signal = 31% |
| WINTER_HYPOXIA_UP | 70 | −0.37486 | −1.5381 | 0.012658 | 0.077262 | 1 | 2904 | tags = 29%, list = 13%, signal = 33% |
| HELLER_HDAC_TARGETS_DN | 222 | −0.30689 | −1.53637 | 0 | 0.077987 | 1 | 2837 | tags = 22%, list = 13%, signal = 25% |
| NAKAMURA_METASTASIS_MODEL_UP | 32 | −0.43733 | −1.5362 | 0.021786 | 0.077897 | 1 | 3784 | tags = 31%, list = 17%, signal = 38% |
| TSENG_IRS1_TARGETS_UP | 110 | −0.3502 | −1.53609 | 0.00542 | 0.077758 | 1 | 5390 | tags = 42%, list = 25%, signal = 55% |
| SAGIV_CD24_TARGETS_DN | 36 | −0.42214 | −1.53213 | 0.014706 | 0.079849 | 1 | 2265 | tags = 25%, list = 10%, signal = 28% |
| ONDER_CDH1_TARGETS_1_DN | 127 | −0.33147 | −1.53188 | 0.005249 | 0.079797 | 1 | 4540 | tags = 31%, list = 21%, signal = 40% |
| REACTOME_RNA_POLYMERASE_I_CHAIN_ELONGATION | 21 | −0.50165 | −1.53108 | 0.041394 | 0.080008 | 1 | 8169 | tags = 62%, list = 37%, signal = 99% |
| SLEBOS_HEAD_AND_NECK_CANCER_WITH_HPV_UP | 59 | −0.38344 | −1.53046 | 0.009732 | 0.080164 | 1 | 6770 | tags = 54%, list = 31%, signal = 78% |
| GENTILE_UV_LOW_DOSE_DN | 17 | −0.50817 | −1.52488 | 0.054622 | 0.083273 | 1 | 3800 | tags = 47%, list = 17%, signal = 57% |
| DACOSTA_UV_RESPONSE_VIA_ERCC3_COMMON_UP | 48 | −0.40433 | −1.52453 | 0.030952 | 0.08328 | 1 | 3115 | tags = 29%, list = 14%, signal = 34% |
| GUTIERREZ_MULTIPLE_MYELOMA_DN | 29 | −0.44814 | −1.52383 | 0.025806 | 0.083507 | 1 | 6150 | tags = 52%, list = 28%, signal = 72% |
| NAKAMURA_TUMOR_ZONE_PERIPHERAL_VS_CENTRAL_UP | 209 | −0.31195 | −1.52226 | 0 | 0.084241 | 1 | 6207 | tags = 41%, list = 28%, signal = 57% |
| GENTILE_UV_LOW_DOSE_UP | 17 | −0.50817 | −1.5203 | 0.045977 | 0.085253 | 1 | 3800 | tags = 47%, list = 17%, signal = 57% |
| KEGG_MELANOMA | 70 | −0.37406 | −1.51908 | 0.020202 | 0.085739 | 1 | 3471 | tags = 21%, list = 16%, signal = 25% |
| GAZDA_DIAMOND_BLACKFAN_ANEMIA_PROGENITOR_DN | 48 | −0.39891 | −1.51767 | 0.011547 | 0.086379 | 1 | 7491 | tags = 65%, list = 34%, signal = 98% |
| HEDENFALK_BREAST_CANCER_BRACX_UP | 15 | −0.53281 | −1.51618 | 0.04186 | 0.087139 | 1 | 4411 | tags = 33%, list = 20%, signal = 42% |
| PYEON_CANCER_HEAD_AND_NECK_VS_CERVICAL_UP | 129 | −0.32837 | −1.51464 | 0.002833 | 0.087896 | 1 | 5555 | tags = 40%, list = 25%, signal = 54% |
| BOHN_PRIMARY_IMMUNODEFICIENCY_SYNDROM_UP | 30 | −0.44959 | −1.5146 | 0.035088 | 0.087709 | 1 | 6557 | tags = 60%, list = 30%, signal = 86% |
| KEGG_PRION_DISEASES | 31 | −0.43419 | −1.50972 | 0.029724 | 0.090708 | 1 | 3648 | tags = 29%, list = 17%, signal = 35% |
| SHAFFER_IRF4_TARGETS_IN_ACTIVATED_DENDRITIC_CELL | 59 | −0.37847 | −1.50914 | 0.010127 | 0.090858 | 1 | 3877 | tags = 34%, list = 18%, signal = 41% |
| REACTOME_FRS2MEDIATED_CASCADE | 26 | −0.45398 | −1.50573 | 0.034884 | 0.092953 | 1 | 2299 | tags = 27%, list = 11%, signal = 30% |
| REACTOME_METABOLISM_OF_PROTEINS | 168 | −0.31495 | −1.50419 | 0.00271 | 0.093745 | 1 | 7289 | tags = 32%, list = 33%, signal = 47% |

TABLE 2-continued

| NAME | SIZE | ES | NES | NOM p-val | FDR q-val | FWER p-val | RANK AT MAX | LEADING EDGE |
|---|---|---|---|---|---|---|---|---|
| SENESE_HDAC3_TARGETS_DN | 380 | −0.28679 | −1.50414 | 0 | 0.09355 | 1 | 4912 | tags = 31%, list = 22%, signal = 39% |
| SHAFFER_IRF4_TARGETS_IN_MYELOMA_VS_MATURE_B_LYMPHOCYTE | 92 | −0.34437 | −1.50159 | 0.002457 | 0.094919 | 1 | 6045 | tags = 42%, list = 28%, signal = 58% |
| VANTVEER_BREAST_CANCER_METASTASIS_DN | 87 | −0.34766 | −1.5009 | 0.005277 | 0.095133 | 1 | 6885 | tags = 47%, list = 31%, signal = 68% |
| BROWNE_HCMV_INFECTION_18HR_UP | 150 | −0.32006 | −1.5001 | 0 | 0.095376 | 1 | 5934 | tags = 39%, list = 27%, signal = 53% |
| CHO_NR4A1_TARGETS | 21 | −0.48094 | −1.4997 | 0.03908 | 0.095394 | 1 | 2408 | tags = 24%, list = 11%, signal = 27% |
| LANDIS_ERBB2_BREAST_TUMORS_65_UP | 21 | −0.47553 | −1.49725 | 0.041943 | 0.096736 | 1 | 180 | tags = 14%, list = 1%, signal = 14% |
| SUNG_METASTASIS_STROMA_DN | 37 | −0.42164 | −1.49584 | 0.033019 | 0.097521 | 1 | 4568 | tags = 46%, list = 21%, signal = 58% |
| KEGG_GLIOMA | 60 | −0.37437 | −1.49578 | 0.028986 | 0.097335 | 1 | 3471 | tags = 22%, list = 16%, signal = 26% |
| LOCKWOOD_AMPLIFIED_IN_LUNG_CANCER | 146 | −0.32124 | −1.49433 | 0.005181 | 0.098139 | 1 | 8242 | tags = 52%, list = 38%, signal = 83% |
| SANA_RESPONSE_TO_IFNG_DN | 69 | −0.3646 | −1.49259 | 0.012077 | 0.099073 | 1 | 6606 | tags = 46%, list = 30%, signal = 66% |
| GARGALOVIC_RESPONSE_TO_OXIDIZED_PHOSPHOLIPIDS_RED_UP | 15 | −0.54264 | −1.49204 | 0.044681 | 0.09925 | 1 | 4810 | tags = 60%, list = 22%, signal = 77% |
| WONG_PROTEASOME_GENE_MODULE | 45 | −0.39346 | −1.49194 | 0.023981 | 0.099068 | 1 | 6478 | tags = 44%, list = 30%, signal = 63% |
| REACTOME_SIGNALLING_TO_RAS | 25 | −0.45679 | −1.49192 | 0.027778 | 0.098842 | 1 | 5189 | tags = 28%, list = 24%, signal = 37% |
| HOFFMANN_PRE_BI_TO_LARGE_PRE_BII_LYMPHOCYTE_UP | 18 | −0.4987 | −1.49113 | 0.04157 | 0.099205 | 1 | 3181 | tags = 44%, list = 15%, signal = 52% |
| KOKKINAKIS_METHIONINE_DEPRIVATION_96HR_DN | 68 | −0.35949 | −1.48846 | 0.006928 | 0.100901 | 1 | 4780 | tags = 32%, list = 22%, signal = 41% |
| FLECHNER_BIOPSY_KIDNEY_TRANSPLANT_OK_VS_DONOR_DN | 20 | −0.48691 | −1.48792 | 0.058275 | 0.101095 | 1 | 3648 | tags = 45%, list = 17%, signal = 54% |
| FULCHER_INFLAMMATORY_RESPONSE_LECTIN_VS_LPS_UP | 425 | −0.27997 | −1.48736 | 0 | 0.101318 | 1 | 4807 | tags = 31%, list = 22%, signal = 39% |
| ALONSO_METASTASIS_UP | 139 | −0.3209 | −1.48195 | 0 | 0.10495 | 1 | 6027 | tags = 37%, list = 28%, signal = 51% |
| SEKI_INFLAMMATORY_RESPONSE_LPS_UP | 75 | −0.35431 | −1.4819 | 0.015584 | 0.104744 | 1 | 2819 | tags = 25%, list = 13%, signal = 29% |
| ROZANOV_MMP14_TARGETS_SUBSET | 31 | −0.43222 | −1.48066 | 0.03125 | 0.105382 | 1 | 3313 | tags = 35%, list = 15%, signal = 42% |
| LIU_TARGETS_OF_VMYB_VS_CMYB_DN | 36 | −0.42063 | −1.48011 | 0.039312 | 0.105606 | 1 | 1816 | tags = 28%, list = 8%, signal = 30% |
| YAO_TEMPORAL_RESPONSE_TO_PROGESTERONE_CLUSTER_5 | 28 | −0.44457 | −1.48001 | 0.045662 | 0.105435 | 1 | 1428 | tags = 21%, list = 7%, signal = 23% |
| NAM_FXYD5_TARGETS_DN | 15 | −0.51417 | −1.47977 | 0.051282 | 0.105388 | 1 | 6150 | tags = 53%, list = 28%, signal = 74% |
| HAMAI_APOPTOSIS_VIA_TRAIL_DN | 110 | −0.33103 | −1.47919 | 0.005376 | 0.105494 | 1 | 4416 | tags = 29%, list = 20%, signal = 36% |
| ZHOU_INFLAMMATORY_RESPONSE_LIVE_UP | 337 | −0.28625 | −1.47794 | 0 | 0.106193 | 1 | 4884 | tags = 31%, list = 22%, signal = 39% |

TABLE 2-continued

| NAME | SIZE | ES | NES | NOM p-val | FDR q-val | FWER p-val | RANK AT MAX | LEADING EDGE |
|---|---|---|---|---|---|---|---|---|
| ENK_UV_RESPONSE_EPIDERMIS_UP | 247 | −0.29261 | −1.47656 | 0 | 0.107043 | 1 | 4059 | tags = 30%, list = 19%, signal = 36% |
| JAERVINEN_AMPLIFIED_IN_LARYNGEAL_CANCER | 31 | −0.43216 | −1.47452 | 0.038278 | 0.108221 | 1 | 4458 | tags = 42%, list = 20%, signal = 53% |
| REACTOME_METABOLISM_OF_CARBOHYDRATES | 107 | −0.3253 | −1.47395 | 0.002584 | 0.108405 | 1 | 6272 | tags = 43%, list = 29%, signal = 60% |
| REACTOME_RNA_POLYMERASE_I_TRANSCRIPTION_TERMINATION | 19 | −0.49033 | −1.47272 | 0.037209 | 0.109075 | 1 | 5229 | tags = 42%, list = 24%, signal = 55% |
| BIOCARTA_NKT_PATHWAY | 27 | −0.45331 | −1.47259 | 0.046296 | 0.108961 | 1 | 1001 | tags = 26%, list = 5%, signal = 27% |
| CHIN_BREAST_CANCER_COPY_NUMBER_UP | 19 | −0.48619 | −1.46993 | 0.056277 | 0.110731 | 1 | 4901 | tags = 47%, list = 22%, signal = 61% |
| BHATI_G2M_ARREST_BY_2METHOXYESTRADIOL_DN | 93 | −0.33428 | −1.46694 | 0.010959 | 0.112645 | 1 | 5711 | tags = 38%, list = 26%, signal = 51% |
| KEGG_PURINE_METABOLISM | 144 | −0.31203 | −1.46666 | 0.00271 | 0.112641 | 1 | 6525 | tags = 46%, list = 30%, signal = 65% |
| KEGG_CYSTEINE_AND_METHIONINE_METABOLISM | 30 | −0.43055 | −1.46474 | 0.041284 | 0.113858 | 1 | 4170 | tags = 33%, list = 19%, signal = 41% |
| KORKOLA_YOLK_SAC_TUMOR_UP | 16 | −0.49958 | −1.46269 | 0.05977 | 0.115226 | 1 | 7367 | tags = 50%, list = 34%, signal = 75% |
| SCHLOSSER_SERUM_RESPONSE_AUGMENTED_BY_MYC | 89 | −0.33937 | −1.46002 | 0.016043 | 0.116993 | 1 | 8503 | tags = 63%, list = 39%, signal = 102% |
| BIOCARTA_P53HYPOXIA_PATHWAY | 21 | −0.4684 | −1.45891 | 0.05794 | 0.117743 | 1 | 4235 | tags = 43%, list = 19%, signal = 53% |
| NUNODA_RESPONSE_TO_DASATINIB_IMATINIB_UP | 28 | −0.43895 | −1.45731 | 0.060046 | 0.118697 | 1 | 3952 | tags = 39%, list = 18%, signal = 48% |
| LEE_LIVER_CANCER_SURVIVAL_DN | 105 | −0.33219 | −1.45577 | 0.010811 | 0.119604 | 1 | 7770 | tags = 49%, list = 35%, signal = 75% |
| SHAFFER_IRF4_TARGETS_IN_PLASMA_CELL_VS_MATURE_B_LYMPHOCYTE | 62 | −0.36088 | −1.45474 | 0.021635 | 0.120228 | 1 | 4008 | tags = 31%, list = 18%, signal = 37% |
| PYEON_HPV_POSITIVE_TUMORS_UP | 58 | −0.36375 | −1.45304 | 0.026005 | 0.121441 | 1 | 6468 | tags = 48%, list = 30%, signal = 68% |
| LINDGREN_BLADDER_CANCER_WITH_LOH_IN_CHR9Q | 87 | −0.33999 | −1.45283 | 0.009732 | 0.121316 | 1 | 7167 | tags = 49%, list = 33%, signal = 73% |
| ENK_UV_RESPONSE_KERATINOCYTE_UP | 442 | −0.27461 | −1.45076 | 0 | 0.122851 | 1 | 6664 | tags = 36%, list = 30%, signal = 50% |
| MCCLUNG_DELTA_FOSB_TARGETS_2WK | 43 | −0.39175 | −1.4494 | 0.042056 | 0.123754 | 1 | 4790 | tags = 37%, list = 22%, signal = 48% |
| VARELA_ZMPSTE24_TARGETS_UP | 38 | −0.39554 | −1.44606 | 0.033493 | 0.126183 | 1 | 3737 | tags = 37%, list = 17%, signal = 44% |
| ZHAN_MULTIPLE_MYELOMA_MS_UP | 34 | −0.41283 | −1.44598 | 0.04119 | 0.125977 | 1 | 836 | tags = 18%, list = 4%, signal = 18% |
| ZUCCHI_METASTASIS_DN | 21 | −0.45835 | −1.44406 | 0.056948 | 0.127368 | 1 | 3297 | tags = 29%, list = 15%, signal = 34% |
| TOOKER_GEMCITABINE_RESISTANCE_DN | 108 | −0.32502 | −1.44285 | 0.01897 | 0.128182 | 1 | 5342 | tags = 41%, list = 24%, signal = 54% |
| WEIGEL_OXIDATIVE_STRESS_RESPONSE | 25 | −0.44035 | −1.44226 | 0.061834 | 0.128403 | 1 | 6203 | tags = 48%, list = 28%, signal = 67% |
| REACTOME_MRNA_SPLICING_MINOR_PATHWAY | 36 | −0.40293 | −1.44226 | 0.035 | 0.128133 | 1 | 8812 | tags = 72%, list = 40%, signal = 121% |

TABLE 2-continued

| NAME | SIZE | ES | NES | NOM p-val | FDR q-val | FWER p-val | RANK AT MAX | LEADING EDGE |
|---|---|---|---|---|---|---|---|---|
| SCIAN_INVERSED_TARGETS_OF_TP53_AND_TP73_DN | 24 | -0.44228 | -1.43996 | 0.050847 | 0.129878 | 1 | 2384 | tags = 25%, list = 11%, signal = 28% |
| YAO_TEMPORAL_RESPONSE_TO_PROGESTERONE_CLUSTER_10 | 62 | -0.35741 | -1.43816 | 0.039216 | 0.13116 | 1 | 8291 | tags = 58%, list = 38%, signal = 93% |
| GESERICK_TERT_TARGETS_DN | 19 | -0.46809 | -1.43387 | 0.063877 | 0.134421 | 1 | 5445 | tags = 58%, list = 25%, signal = 77% |
| SYED_ESTRADIOL_RESPONSE | 15 | -0.50256 | -1.43354 | 0.075688 | 0.134435 | 1 | 1119 | tags = 27%, list = 5%, signal = 28% |
| REACTOME_CITRIC_ACID_CYCLE | 18 | -0.48351 | -1.43321 | 0.072072 | 0.134449 | 1 | 9447 | tags = 78%, list = 43%, signal = 137% |
| GARGALOVIC_RESPONSE_TO_OXIDIZED_PHOSPHOLIPIDS_MAGENTA_UP | 19 | -0.46937 | -1.43264 | 0.072893 | 0.134647 | 1 | 5056 | tags = 47%, list = 23%, signal = 62% |
| CAFFAREL_RESPONSE_TO_THC_24HR_5_UP | 23 | -0.44394 | -1.43258 | 0.067834 | 0.134415 | 1 | 6027 | tags = 48%, list = 28%, signal = 66% |
| TOOKER_RESPONSE_TO_BEXAROTENE_UP | 108 | -0.32502 | -1.4324 | 0.017413 | 0.134261 | 1 | 5342 | tags = 41%, list = 24%, signal = 54% |
| NIKOLSKY_BREAST_CANCER_17Q11_Q21_AMPLICON | 74 | -0.34376 | -1.43141 | 0.029851 | 0.134823 | 1 | 4558 | tags = 32%, list = 21%, signal = 41% |
| DACOSTA_UV_RESPONSE_VIA_ERCC3_XPCS_UP | 15 | -0.49893 | -1.42982 | 0.079523 | 0.136028 | 1 | 2092 | tags = 20%, list = 10%, signal = 22% |
| ZHOU_INFLAMMATORY_RESPONSE_FIMA_UP | 363 | -0.27303 | -1.4289 | 0 | 0.136663 | 1 | 4767 | tags = 28%, list = 22%, signal = 36% |
| FONTAINE_PAPILLARY_THYROID_CARCINOMA_DN | 61 | -0.35621 | -1.42837 | 0.039443 | 0.136889 | 1 | 3080 | tags = 25%, list = 14%, signal = 29% |
| REACTOME_E2F_TRANSCRIPTIONAL_TARGETS_AT_G1_S | 19 | -0.47601 | -1.42739 | 0.053991 | 0.137516 | 1 | 3495 | tags = 47%, list = 16%, signal = 56% |
| LUND_SILENCED_BY_METHYLATION | 15 | -0.49663 | -1.42579 | 0.081678 | 0.138766 | 1 | 3242 | tags = 27%, list = 15%, signal = 31% |
| WANG_RESPONSE_TO_FORSKOLIN_UP | 17 | -0.48715 | -1.42558 | 0.071111 | 0.138668 | 1 | 6045 | tags = 59%, list = 28%, signal = 81% |
| SESTO_RESPONSE_TO_UV_C4 | 17 | -0.47406 | -1.42534 | 0.088167 | 0.138601 | 1 | 6342 | tags = 65%, list = 29%, signal = 91% |
| STARK_PREFRONTAL_CORTEX_22Q11_DELETION_DN | 438 | -0.27075 | -1.42474 | 0 | 0.138849 | 1 | 6692 | tags = 36%, list = 31%, signal = 51% |
| BHATTACHARYA_EMBRYONIC_STEM_CELL | 62 | -0.35682 | -1.42423 | 0.040189 | 0.138977 | 1 | 2402 | tags = 24%, list = 11%, signal = 27% |
| BIOCARTA_SHH_PATHWAY | 15 | -0.4984 | -1.42376 | 0.077778 | 0.139189 | 1 | 1205 | tags = 27%, list = 6%, signal = 28% |
| REACTOME_CONVERSION_FROM_APC_CDC20_TO_APC_CDH1_IN_LATE_ANAPHASE | 16 | -0.48592 | -1.4233 | 0.087527 | 0.139328 | 1 | 7138 | tags = 56%, list = 33%, signal = 83% |
| RICKMAN_TUMOR_DIFFERENTIATED_WELL_VS_POORLY_DN | 269 | -0.2814 | -1.42256 | 0.003311 | 0.139667 | 1 | 2935 | tags = 19%, list = 13%, signal = 22% |
| ABE_VEGFA_TARGETS_2HR | 16 | -0.49199 | -1.42146 | 0.078125 | 0.14043 | 1 | 3857 | tags = 31%, list = 18%, signal = 38% |
| MULLIGHAN_MLL_SIGNATURE_1_DN | 190 | -0.2899 | -1.41882 | 0.002933 | 0.142577 | 1 | 3575 | tags = 25%, list = 16%, signal = 29% |
| NIKOLSKY_BREAST_CANCER_11Q12_Q14_AMPLICON | 116 | -0.31321 | -1.41616 | 0.014205 | 0.144815 | 1 | 5767 | tags = 38%, list = 26%, signal = 51% |
| RICKMAN_HEAD_AND_NECK_CANCER_D | 21 | -0.46169 | -1.41475 | 0.077803 | 0.145862 | 1 | 2856 | tags = 33%, list = 13%, signal = 38% |

TABLE 2-continued

| NAME | SIZE | ES | NES | NOM p-val | FDR q-val | FWER p-val | RANK AT MAX | LEADING EDGE |
|---|---|---|---|---|---|---|---|---|
| HELLER_SILENCED_BY_METHYLATION_DN | 82 | −0.32818 | −1.41447 | 0.040865 | 0.145871 | 1 | 3138 | tags = 24%, list = 14%, signal = 28% |
| REACTOME_LOSS_OF_NLP_FROM_MITOTIC_CENTROSOMES | 52 | −0.36399 | −1.41391 | 0.045564 | 0.146124 | 1 | 7600 | tags = 44%, list = 35%, signal = 68% |
| GAUSSMANN_MLL_AF4_FUSION_TARGETS_D_UP | 29 | −0.4174 | −1.41092 | 0.06422 | 0.148574 | 1 | 125 | tags = 10%, list = 1%, signal = 10% |
| LIAO_HAVE_SOX4_BINDING_SITES | 34 | −0.39227 | −1.40797 | 0.050239 | 0.151067 | 1 | 3422 | tags = 29%, list = 16%, signal = 35% |
| REACTOME_G1_PHASE | 15 | −0.49867 | −1.40719 | 0.067982 | 0.151451 | 1 | 5167 | tags = 47%, list = 24%, signal = 61% |
| KEGG_HUNTINGTONS_DISEASE | 151 | −0.29949 | −1.40388 | 0.019126 | 0.15437 | 1 | 9317 | tags = 54%, list = 43%, signal = 94% |
| DUTTA_APOPTOSIS_VIA_NFKB | 27 | −0.42005 | −1.40305 | 0.067146 | 0.154958 | 1 | 5445 | tags = 44%, list = 25%, signal = 59% |
| ZHANG_ANTIVIRAL_RESPONSE_TO_RIBAVIRIN_DN | 38 | −0.38083 | −1.40241 | 0.062053 | 0.155326 | 1 | 611 | tags = 13%, list = 3%, signal = 14% |
| CHUNG_BLISTER_CYTOTOXICITY_UP | 103 | −0.31972 | −1.40192 | 0.023316 | 0.155473 | 1 | 6392 | tags = 48%, list = 29%, signal = 67% |
| STREICHER_LSM1_TARGETS_DN | 16 | −0.47911 | −1.40091 | 0.081818 | 0.156243 | 1 | 3808 | tags = 44%, list = 17%, signal = 53% |
| GAL_LEUKEMIC_STEM_CELL_DN | 179 | −0.28739 | −1.39983 | 0.006042 | 0.156978 | 1 | 5413 | tags = 37%, list = 25%, signal = 49% |
| KANG_CISPLATIN_RESISTANCE_UP | 15 | −0.48395 | −1.39942 | 0.091667 | 0.157037 | 1 | 4105 | tags = 40%, list = 19%, signal = 49% |
| KEGG_JAK_STAT_SIGNALING_PATHWAY | 125 | −0.30333 | −1.39847 | 0.014535 | 0.157726 | 1 | 2071 | tags = 17%, list = 9%, signal = 18% |
| NATSUME_RESPONSE_TO_INTERFERON_BETA_UP | 60 | −0.34866 | −1.39702 | 0.027842 | 0.158946 | 1 | 2299 | tags = 20%, list = 11%, signal = 22% |
| MULLIGHAN_MLL_SIGNATURE_2_DN | 222 | −0.28409 | −1.39699 | 0.003086 | 0.158673 | 1 | 3580 | tags = 25%, list = 16%, signal = 29% |
| GARGALOVIC_RESPONSE_TO_OXIDIZED_PHOSPHOLIPIDS_GREEN_UP | 16 | −0.49774 | −1.39631 | 0.100877 | 0.159064 | 1 | 3226 | tags = 44%, list = 15%, signal = 51% |
| AMIT_DELAYED_EARLY_GENES | 17 | −0.4758 | −1.39595 | 0.112288 | 0.159133 | 1 | 4812 | tags = 41%, list = 22%, signal = 53% |
| DING_LUNG_CANCER_EXPRESSION_BY_COPY_NUMBER | 87 | −0.32447 | −1.39372 | 0.019048 | 0.16113 | 1 | 7128 | tags = 46%, list = 33%, signal = 68% |
| LIU_CDX2_TARGETS_UP | 34 | −0.38811 | −1.39227 | 0.072687 | 0.162389 | 1 | 1640 | tags = 26%, list = 7%, signal = 29% |
| KEGG_TYPE_I_DIABETES_MELLITUS | 20 | −0.44458 | −1.39179 | 0.072527 | 0.162603 | 1 | 1967 | tags = 30%, list = 9%, signal = 33% |
| CROMER_TUMORIGENESIS_UP | 40 | −0.37638 | −1.39164 | 0.058696 | 0.162456 | 1 | 4323 | tags = 35%, list = 20%, signal = 44% |
| DEURIG_T_CELL_PROLYMPHOCYTIC_LEUKEMIA_UP | 283 | −0.27378 | −1.39152 | 0.008571 | 0.162236 | 1 | 6302 | tags = 40%, list = 29%, signal = 56% |
| HEIDENBLAD_AMPLICON_12P11_12_DN | 20 | −0.45761 | −1.3913 | 0.084821 | 0.162175 | 1 | 4939 | tags = 40%, list = 23%, signal = 52% |
| OUYANG_PROSTATE_CANCER_PROGRESSION_DN | 20 | −0.44637 | −1.3894 | 0.079007 | 0.163869 | 1 | 5543 | tags = 50%, list = 25%, signal = 67% |
| JAZAG_TGFB1_SIGNALING_UP | 87 | −0.32574 | −1.38754 | 0.044554 | 0.165713 | 1 | 3619 | tags = 25%, list = 17%, signal = 30% |

TABLE 2-continued

| NAME | SIZE | ES | NES | NOM p-val | FDR q-val | FWER p-val | RANK AT MAX | LEADING EDGE |
|---|---|---|---|---|---|---|---|---|
| INGA_TP53_TARGETS | 15 | -0.4848 | -1.38524 | 0.10101 | 0.167718 | 1 | 2331 | tags = 40%, list = 11%, signal = 45% |
| MANALO_HYPOXIA_UP | 172 | -0.29333 | -1.3817 | 0.011561 | 0.171048 | 1 | 3766 | tags = 28%, list = 17%, signal = 33% |
| XU_HGF_SIGNALING_NOT_VIA_AKT1_48HR_DN | 16 | -0.48281 | -1.38157 | 0.088795 | 0.170853 | 1 | 5908 | tags = 63%, list = 27%, signal = 86% |
| TURASHVILI_BREAST_LOBULAR_CARCINOMA_VS_DUCTAL_NORMAL_DN | 69 | -0.33538 | -1.37992 | 0.039024 | 0.172203 | 1 | 294 | tags = 10%, list = 1%, signal = 10% |
| NIKOLSKY_BREAST_CANCER_12Q13_Q21_AMPLICON | 34 | -0.3841 | -1.37926 | 0.077803 | 0.172586 | 1 | 4173 | tags = 32%, list = 19%, signal = 40% |
| KEGG_ARGININE_AND_PROLINE_METABOLISM | 47 | -0.3636 | -1.37822 | 0.070776 | 0.173393 | 1 | 3132 | tags = 30%, list = 14%, signal = 35% |
| REACTOME_SYNTHESIS_OF_GLYCOSYLPHOSPHATIDYLINOSITOL | 16 | -0.47441 | -1.37695 | 0.111588 | 0.174442 | 1 | 6172 | tags = 44%, list = 28%, signal = 61% |
| REACTOME_INACTIVATION_OF_APC_VIA_DIRECT_INHIBITION_OF_THE_APCOMPLEX | 17 | -0.46918 | -1.37676 | 0.088838 | 0.174322 | 1 | 7138 | tags = 53%, list = 33%, signal = 78% |
| ST_B_CELL_ANTIGEN_RECEPTOR | 36 | -0.38174 | -1.37647 | 0.05814 | 0.17434 | 1 | 3812 | tags = 28%, list = 17%, signal = 34% |
| GAUSSMANN_MLL_AF4_FUSION_TARGETS_F_DN | 27 | -0.40752 | -1.37623 | 0.095652 | 0.174294 | 1 | 2411 | tags = 30%, list = 11%, signal = 33% |
| KYNG_DNA_DAMAGE_BY_4NQO | 17 | -0.45897 | -1.37587 | 0.107368 | 0.174363 | 1 | 1732 | tags = 24%, list = 8%, signal = 26% |
| SU_TESTIS | 62 | -0.34375 | -1.37581 | 0.046683 | 0.174071 | 1 | 5348 | tags = 42%, list = 24%, signal = 55% |
| BROWNE_HCMV_INFECTION_2HR_UP | 28 | -0.407 | -1.37524 | 0.08204 | 0.174391 | 1 | 3970 | tags = 32%, list = 18%, signal = 39% |
| REACTOME_UNFOLDED_PROTEIN_RESPONSE | 18 | -0.45886 | -1.37523 | 0.115217 | 0.174075 | 1 | 7114 | tags = 50%, list = 32%, signal = 74% |
| IVANOVA_HEMATOPOIESIS_INTERMEDIATE_PROGENITOR | 29 | -0.41056 | -1.37523 | 0.068522 | 0.173752 | 1 | 4404 | tags = 41%, list = 20%, signal = 52% |
| SENESE_HDAC1_TARGETS_UP | 344 | -0.26657 | -1.37487 | 0 | 0.173825 | 1 | 5259 | tags = 31%, list = 24%, signal = 40% |
| KEGG_PRIMARY_IMMUNODEFICIENCY | 35 | -0.39068 | -1.37478 | 0.077694 | 0.1736 | 1 | 3963 | tags = 31%, list = 18%, signal = 38% |
| AMIT_EGF_RESPONSE_60_MCF10A | 33 | -0.38962 | -1.3747 | 0.070953 | 0.173354 | 1 | 4397 | tags = 36%, list = 20%, signal = 45% |
| MORI_PLASMA_CELL_UP | 30 | -0.40091 | -1.3743 | 0.072562 | 0.17349 | 1 | 6311 | tags = 43%, list = 29%, signal = 61% |
| FERRANDO_T_ALL_WITH_MLL_ENL_FUSION_DN | 67 | -0.33108 | -1.37238 | 0.029268 | 0.175255 | 1 | 6337 | tags = 48%, list = 29%, signal = 67% |
| DOANE_RESPONSE_TO_ANDROGEN_DN | 203 | -0.27826 | -1.36984 | 0.011173 | 0.177593 | 1 | 3806 | tags = 27%, list = 17%, signal = 32% |
| SA_TRKA_RECEPTOR | 15 | -0.48644 | -1.36971 | 0.108597 | 0.17744 | 1 | 1839 | tags = 20%, list = 8%, signal = 22% |
| YAMASHITA_LIVER_CANCER_WITH_EPCAM_UP | 38 | -0.37132 | -1.36872 | 0.062791 | 0.178152 | 1 | 5931 | tags = 29%, list = 27%, signal = 40% |
| JAZAG_TGFB1_SIGNALING_VIA_SMAD4_DN | 51 | -0.35582 | -1.36801 | 0.058685 | 0.178675 | 1 | 3297 | tags = 24%, list = 15%, signal = 28% |
| LIAO_METASTASIS | 395 | -0.26093 | -1.36768 | 0 | 0.178704 | 1 | 4016 | tags = 24%, list = 18%, signal = 29% |

TABLE 2-continued

| NAME | SIZE | ES | NES | NOM p-val | FDR q-val | FWER p-val | RANK AT MAX | LEADING EDGE |
|---|---|---|---|---|---|---|---|---|
| CAIRO_HEPATOBLASTOMA_UP | 172 | −0.2862 | −1.3674 | 0.00545 | 0.178707 | 1 | 5649 | tags = 38%, list = 26%, signal = 51% |
| HAHTOLA_SEZARY_SYNDROM_DN | 32 | −0.39169 | −1.36721 | 0.084071 | 0.178597 | 1 | 1716 | tags = 22%, list = 8%, signal = 24% |
| PROVENZANI_METASTASIS_UP | 153 | −0.29047 | −1.3665 | 0.002849 | 0.179207 | 1 | 4855 | tags = 27%, list = 22%, signal = 34% |
| REACTOME_SIGNALLING_TO_ERKS | 32 | −0.39226 | −1.36647 | 0.091981 | 0.178911 | 1 | 5189 | tags = 22%, list = 24%, signal = 29% |
| KEGG_OXIDATIVE_PHOSPHORYLATION | 105 | −0.30522 | −1.36542 | 0.019753 | 0.179829 | 1 | 9520 | tags = 50%, list = 43%, signal = 87% |
| NIKOLSKY_BREAST_CANCER_6P24_P22_AMPLICON | 16 | −0.45905 | −1.36526 | 0.111111 | 0.179648 | 1 | 1518 | tags = 19%, list = 7%, signal = 20% |
| REACTOME_CENTROSOME_MATURATION | 59 | −0.34139 | −1.36439 | 0.042254 | 0.18028 | 1 | 7600 | tags = 44%, list = 35%, signal = 67% |
| GAUSSMANN_MLL_AF4_FUSION_TARGETS_G_DN | 27 | −0.4069 | −1.36369 | 0.089862 | 0.18075 | 1 | 3580 | tags = 33%, list = 16%, signal = 40% |
| REACTOME_ELECTRON_TRANSPORT_CHAIN | 60 | −0.34238 | −1.36326 | 0.048055 | 0.1809 | 1 | 9617 | tags = 52%, list = 44%, signal = 92% |
| PUIFFE_INVASION_INHIBITED_BY_ASCITES_UP | 62 | −0.33929 | −1.36065 | 0.053528 | 0.183487 | 1 | 7069 | tags = 52%, list = 32%, signal = 76% |
| ALCALAY_AML_BY_NPM1_LOCALIZATION_DN | 160 | −0.29008 | −1.35956 | 0.020231 | 0.184411 | 1 | 5407 | tags = 39%, list = 25%, signal = 51% |
| REACTOME_DOWNSTREAM_SIGNALING_OF_ACTIVATED_FGFR | 41 | −0.3687 | −1.35949 | 0.073394 | 0.18419 | 1 | 2299 | tags = 20%, list = 11%, signal = 22% |
| GRADE_COLON_VS_RECTAL_CANCER_DN | 35 | −0.38706 | −1.3576 | 0.092511 | 0.186036 | 1 | 2486 | tags = 26%, list = 11%, signal = 29% |
| REACTOME_ZINC_TRANSPORTATION | 17 | −0.46026 | −1.35645 | 0.112527 | 0.187041 | 1 | 6501 | tags = 65%, list = 30%, signal = 92% |
| REACTOME_CHEMOKINE_RECEPTORS_BIND_CHEMOKINES | 44 | −0.36558 | −1.35641 | 0.069378 | 0.186759 | 1 | 561 | tags = 18%, list = 3%, signal = 19% |
| NOUZOVA_TRETINOIN_AND_H4_ACETYLATION | 97 | −0.31025 | −1.35591 | 0.024691 | 0.186986 | 1 | 6672 | tags = 43%, list = 30%, signal = 62% |
| PUIFFE_INVASION_INHIBITED_BY_ASCITES_DN | 113 | −0.29756 | −1.35527 | 0.032663 | 0.187369 | 1 | 5450 | tags = 29%, list = 25%, signal = 39% |
| IZADPANAH_STEM_CELL_ADIPOSE_VS_BONE_UP | 92 | −0.31369 | −1.35476 | 0.041995 | 0.187571 | 1 | 1854 | tags = 18%, list = 8%, signal = 20% |
| BERENJENO_TRANSFORMED_BY_RHOA_REVERSIBLY_DN | 28 | −0.40651 | −1.35346 | 0.084071 | 0.188776 | 1 | 4723 | tags = 43%, list = 22%, signal = 55% |
| RUGO_RESPONSE_TO_4NQO | 17 | −0.45897 | −1.35286 | 0.121413 | 0.189087 | 1 | 1732 | tags = 24%, list = 8%, signal = 26% |
| ZHAN_V2_LATE_DIFFERENTIATION_GENES | 30 | −0.39762 | −1.35079 | 0.110855 | 0.191172 | 1 | 829 | tags = 13%, list = 4%, signal = 14% |
| KEGG_BLADDER_CANCER | 37 | −0.37393 | −1.3502 | 0.083732 | 0.191564 | 1 | 3471 | tags = 30%, list = 16%, signal = 35% |
| AMIT_SERUM_RESPONSE_40_MCF10A | 26 | −0.4153 | −1.34967 | 0.083333 | 0.19181 | 1 | 3857 | tags = 38%, list = 18%, signal = 47% |
| BASSO_B_LYMPHOCYTE_NETWORK | 117 | −0.29903 | −1.34907 | 0.026455 | 0.192131 | 1 | 5766 | tags = 41%, list = 26%, signal = 55% |
| KEGG_GAP_JUNCTION | 72 | −0.31987 | −1.34898 | 0.057292 | 0.191883 | 1 | 5612 | tags = 31%, list = 26%, signal = 41% |

TABLE 2-continued

| NAME | SIZE | ES | NES | NOM p-val | FDR q-val | FWER p-val | RANK AT MAX | LEADING EDGE |
|---|---|---|---|---|---|---|---|---|
| DAIRKEE_CANCER_PRONE_RESPONSE_BPA | 42 | −0.36551 | −1.34701 | 0.084706 | 0.193933 | 1 | 6558 | tags = 45%, list = 30%, signal = 64% |
| ZHAN_MULTIPLE_MYELOMA_UP | 45 | −0.35975 | −1.34516 | 0.068027 | 0.195909 | 1 | 3138 | tags = 22%, list = 14%, signal = 26% |
| GARGALOVIC_RESPONSE_TO_OXIDIZED_PHOSPHOLIPIDS_GREEN_DN | 20 | −0.43645 | −1.34499 | 0.105376 | 0.195757 | 1 | 4644 | tags = 35%, list = 21%, signal = 44% |
| LI_AMPLIFIED_IN_LUNG_CANCER | 151 | −0.28645 | −1.34477 | 0.032967 | 0.19569 | 1 | 6606 | tags = 36%, list = 30%, signal = 51% |
| NIKOLSKY_BREAST_CANCER_16P13_AMPLICON | 80 | −0.31761 | −1.34287 | 0.041775 | 0.197573 | 1 | 6234 | tags = 35%, list = 28%, signal = 49% |
| DORN_ADENOVIRUS_INFECTION_12HR_DN | 25 | −0.41072 | −1.33962 | 0.115473 | 0.201171 | 1 | 2099 | tags = 24%, list = 10%, signal = 27% |
| MATTIOLI_MGUS_VS_PCL | 80 | −0.31539 | −1.33921 | 0.045685 | 0.20132 | 1 | 8124 | tags = 59%, list = 37%, signal = 93% |
| BROWNE_HCMV_INFECTION_48HR_UP | 152 | −0.28689 | −1.33802 | 0.021918 | 0.202463 | 1 | 3838 | tags = 26%, list = 18%, signal = 31% |
| REACTOME_METAL_ION_SLC_TRANSPORTERS | 23 | −0.41626 | −1.33738 | 0.113527 | 0.202874 | 1 | 6501 | tags = 57%, list = 30%, signal = 80% |
| KEGG_FRUCTOSE_AND_MANNOSE_METABOLISM | 31 | −0.38665 | −1.33501 | 0.095794 | 0.205558 | 1 | 3136 | tags = 29%, list = 14%, signal = 34% |
| ALONSO_METASTASIS_EMT_UP | 28 | −0.39044 | −1.3334 | 0.104019 | 0.207212 | 1 | 5944 | tags = 46%, list = 27%, signal = 64% |
| GAZDA_DIAMOND_BLACKFAN_ANEMIA_MYELOID_UP | 24 | −0.40873 | −1.33216 | 0.120879 | 0.208481 | 1 | 4222 | tags = 38%, list = 19%, signal = 46% |
| DAZARD_RESPONSE_TO_UV_NHEK_UP | 131 | −0.28972 | −1.33138 | 0.032 | 0.209178 | 1 | 3553 | tags = 24%, list = 16%, signal = 29% |
| BROCKE_APOPTOSIS_REVERSED_BY_IL6 | 114 | −0.29444 | −1.33029 | 0.032609 | 0.210268 | 1 | 6301 | tags = 41%, list = 29%, signal = 58% |
| BARIS_THYROID_CANCER_DN | 52 | −0.34946 | −1.33019 | 0.070707 | 0.210052 | 1 | 4070 | tags = 23%, list = 19%, signal = 28% |
| WOOD_EBV_EBNA1_TARGETS_UP | 98 | −0.30448 | −1.32962 | 0.059896 | 0.210401 | 1 | 3669 | tags = 28%, list = 17%, signal = 33% |
| REACTOME_TIGHT_JUNCTION_INTERACTIONS | 28 | −0.38824 | −1.32925 | 0.10274 | 0.210475 | 1 | 3920 | tags = 36%, list = 18%, signal = 43% |
| REACTOME_REGULATION_OF_ORNITHINE_DECARBOXYLASE | 46 | −0.35349 | −1.32563 | 0.09828 | 0.214739 | 1 | 8423 | tags = 63%, list = 38%, signal = 102% |
| GALLUZZI_PERMEABILIZE_MITOCHONDRIA | 35 | −0.36982 | −1.32513 | 0.091723 | 0.214976 | 1 | 6001 | tags = 49%, list = 27%, signal = 67% |
| YAO_TEMPORAL_RESPONSE_TO_PROGESTERONE_CLUSTER_4 | 15 | −0.46388 | −1.32412 | 0.137778 | 0.215918 | 1 | 4888 | tags = 47%, list = 22%, signal = 60% |
| BENPORATH_ES_CORE_NINE_CORRELATED | 91 | −0.30699 | −1.32391 | 0.035806 | 0.21583 | 1 | 6570 | tags = 43%, list = 30%, signal = 61% |
| KEGG_UBIQUITIN_MEDIATED_PROTEOLYSIS | 118 | −0.296 | −1.32145 | 0.033241 | 0.218606 | 1 | 6495 | tags = 36%, list = 30%, signal = 52% |
| TANAKA_METHYLATED_IN_ESOPHAGEAL_CARCINOMA | 75 | −0.31873 | −1.32092 | 0.065823 | 0.218944 | 1 | 4644 | tags = 32%, list = 21%, signal = 40% |
| RUGO_RESPONSE_TO_GAMMA_RADIATION | 39 | −0.36072 | −1.32014 | 0.098558 | 0.219606 | 1 | 1156 | tags = 15%, list = 5%, signal = 16% |

TABLE 2-continued

| NAME | SIZE | ES | NES | NOM p-val | FDR q-val | FWER p-val | RANK AT MAX | LEADING EDGE |
|---|---|---|---|---|---|---|---|---|
| XU_HGF_SIGNALING_NOT_VIA_AKT1_6HR | 22 | -0.42546 | -1.31901 | 0.129386 | 0.220615 | 1 | 4729 | tags = 45%, list = 22%, signal = 58% |
| WATTEL_AUTONOMOUS_THYROID_ADENOMA_UP | 18 | -0.43983 | -1.31832 | 0.138144 | 0.221187 | 1 | 2366 | tags = 33%, list = 11%, signal = 37% |
| ENK_UV_RESPONSE_EPIDERMIS_DN | 439 | -0.24798 | -1.31748 | 0.003802 | 0.221869 | 1 | 4819 | tags = 28%, list = 22%, signal = 35% |
| REACTOME_IRS_RELATED_EVENTS | 71 | -0.32099 | -1.31736 | 0.054502 | 0.22169 | 1 | 2338 | tags = 17%, list = 11%, signal = 19% |
| CREIGHTON_ENDOCRINE_THERAPY_RESISTANCE_1 | 388 | -0.25131 | -1.31344 | 0.006757 | 0.226775 | 1 | 5469 | tags = 32%, list = 25%, signal = 43% |
| OUELLET_OVARIAN_CANCER_INVASIVE_VS_LMP_UP | 105 | -0.29715 | -1.31312 | 0.053571 | 0.226785 | 1 | 7051 | tags = 42%, list = 32%, signal = 62% |
| BIOCARTA_BAD_PATHWAY | 24 | -0.40186 | -1.31268 | 0.121593 | 0.226992 | 1 | 1346 | tags = 13%, list = 6%, signal = 13% |
| REACTOME_SYNTHESIS_AND_INTERCONVERSION_OF_NUCLEOTIDE_DI_AND_TRIPHOSPHATES | 16 | -0.45318 | -1.31235 | 0.145089 | 0.227095 | 1 | 6525 | tags = 63%, list = 30%, signal = 89% |
| WANG_CISPLATIN_RESPONSE_AND_XPC_UP | 106 | -0.29389 | -1.31204 | 0.052219 | 0.227107 | 1 | 5908 | tags = 36%, list = 27%, signal = 49% |
| REACTOME_FURTHER_PLATELET_RELEASATE | 20 | -0.4288 | -1.31183 | 0.12065 | 0.227023 | 1 | 196 | tags = 10%, list = 1%, signal = 10% |
| FLOTHO_PEDIATRIC_ALL_THERAPY_RESPONSE_DN | 20 | -0.43318 | -1.31001 | 0.147609 | 0.22914 | 1 | 3841 | tags = 45%, list = 18%, signal = 55% |
| HAMAI_APOPTOSIS_VIA_TRAIL_UP | 292 | -0.25561 | -1.30972 | 0.006349 | 0.229122 | 1 | 4889 | tags = 30%, list = 22%, signal = 38% |
| REACTOME_PHOSPHORYLATION_OF_THE_APC | 15 | -0.46234 | -1.30877 | 0.120879 | 0.22999 | 1 | 7138 | tags = 53%, list = 33%, signal = 79% |
| MULLIGHAN_NPM1_MUTATED_SIGNATURE_1_UP | 211 | -0.26002 | -1.30758 | 0.012232 | 0.231218 | 1 | 5047 | tags = 29%, list = 23%, signal = 38% |
| SWEET_LUNG_CANCER_KRAS_UP | 442 | -0.24403 | -1.30611 | 0.00365 | 0.232909 | 1 | 4747 | tags = 24%, list = 22%, signal = 30% |
| KYNG_DNA_DAMAGE_BY_GAMMA_RADIATION | 39 | -0.36072 | -1.30513 | 0.123543 | 0.233851 | 1 | 1156 | tags = 15%, list = 5%, signal = 16% |
| SHAFFER_IRF4_MULTIPLE_MYELOMA_PROGRAM | 35 | -0.37016 | -1.30389 | 0.10643 | 0.234189 | 1 | 6001 | tags = 49%, list = 27%, signal = 67% |
| BIOCARTA_PTDINS_PATHWAY | 22 | -0.41198 | -1.30389 | 0.115294 | 0.234737 | 1 | 2241 | tags = 14%, list = 10%, signal = 15% |
| RICKMAN_TUMOR_DIFFERENTIATED_WELL_VS_POORLY_UP | 175 | -0.27162 | -1.30354 | 0.027933 | 0.234776 | 1 | 5781 | tags = 36%, list = 26%, signal = 49% |
| CUL_TCF21_TARGETS_DN | 31 | -0.37395 | -1.30352 | 0.107623 | 0.234418 | 1 | 3639 | tags = 39%, list = 17%, signal = 46% |
| JI_RESPONSE_TO_FSH_DN | 44 | -0.33997 | -1.3032 | 0.098214 | 0.234476 | 1 | 3310 | tags = 23%, list = 15%, signal = 27% |
| CAIRO_LIVER_DEVELOPMENT_UP | 143 | -0.27913 | -1.30278 | 0.025707 | 0.234671 | 1 | 4590 | tags = 29%, list = 21%, signal = 37% |
| REACTOME_BRANCHED_CHAIN_AMINO_ACID_CATABOLISM | 16 | -0.44355 | -1.30278 | 0.1566 | 0.234293 | 1 | 4842 | tags = 38%, list = 22%, signal = 48% |

TABLE 2-continued

| NAME | SIZE | ES | NES | NOM p-val | FDR q-val | FWER p-val | RANK AT MAX | LEADING EDGE |
|---|---|---|---|---|---|---|---|---|
| REACTOME_PYRUVATE_METABOLISM | 15 | −0.46909 | −1.29992 | 0.16309 | 0.238032 | 1 | 7030 | tags = 60%, list = 32%, signal = 88% |
| WINTER_HYPOXIA_METAGENE | 190 | −0.26745 | −1.29969 | 0.017391 | 0.237964 | 1 | 3203 | tags = 23%, list = 15%, signal = 26% |
| CHESLER_BRAIN_QTL_CIS | 68 | −0.31806 | −1.29925 | 0.071253 | 0.238215 | 1 | 4520 | tags = 29%, list = 21%, signal = 37% |
| AIGNER_ZEB1_TARGETS | 28 | −0.38265 | −1.29922 | 0.124711 | 0.237876 | 1 | 1207 | tags = 21%, list = 6%, signal = 23% |
| KYNG_DNA_DAMAGE_UP | 89 | −0.30141 | −1.29871 | 0.082915 | 0.238145 | 1 | 2200 | tags = 18%, list = 10%, signal = 20% |
| WU_APOPTOSIS_BY_CDKN1A_VIA_TP53 | 28 | −0.39139 | −1.29864 | 0.138158 | 0.237897 | 1 | 6063 | tags = 57%, list = 28%, signal = 79% |
| SESTO_RESPONSE_TO_UV_C0 | 95 | −0.30145 | −1.29724 | 0.058824 | 0.23949 | 1 | 8116 | tags = 47%, list = 37%, signal = 75% |
| KEGG_PEROXISOME | 68 | −0.30916 | −1.29473 | 0.070423 | 0.242697 | 1 | 4526 | tags = 32%, list = 21%, signal = 41% |
| MARKEY_RB1_CHRONIC_LOF_UP | 106 | −0.29214 | −1.29443 | 0.045802 | 0.242773 | 1 | 7461 | tags = 51%, list = 34%, signal = 77% |
| SHI_SPARC_TARGETS_UP | 19 | −0.41989 | −1.29379 | 0.129464 | 0.24335 | 1 | 2615 | tags = 26%, list = 12%, signal = 30% |
| REACTOME_GLUCONEOGENESIS | 26 | −0.39437 | −1.29324 | 0.125275 | 0.243803 | 1 | 4616 | tags = 35%, list = 21%, signal = 44% |
| REACTOME_DOWN_STREAM_SIGNAL_TRANSDUCTION | 35 | −0.35619 | −1.29187 | 0.113043 | 0.245395 | 1 | 1359 | tags = 9%, list = 6%, signal = 9% |
| AMUNDSON_POOR_SURVIVAL_AFTER_GAMMA_RADIATION_2G | 127 | −0.28342 | −1.29163 | 0.033613 | 0.245292 | 1 | 4962 | tags = 30%, list = 23%, signal = 38% |

TABLE 3

| Gene Symbol | Gene Title | p value (interaction) | Foxp3Cre Sema/IgG | Nrp1 f/f x Foxp3 Cre Sema/IgG |
|---|---|---|---|---|
| Pf4 | platelet factor 4 | 0.00009599 | 1.545577742 | 1.009665494 |
| Ntn4 | netrin 4 | 0.00000305 | 1.352296007 | 1.172896253 |
| Gbp1 | guanylate binding protein 1 | 6.342E−12 | 1.355007012 | 1.16096399 |
| Sox6 | SRY-box containing gene 6 | 0.0030674 | 1.443495801 | 0.972584119 |
| Zbtb20 | zinc finger and BTB domain containing 20 | 0.000001211 | 1.331835698 | 1.082126493 |
| Zbtb4 | zinc finger and BTB domain containing 4 | 3.64E−09 | 1.255748611 | 1.082036273 |
| S1pr1 | sphingosine-1-phosphate receptor 1 | 2.009E−09 | 1.204529765 | 1.087154433 |
| Selp | selectin, platelet | 0.00203095 | 1.300955862 | 1.043575103 |
| Klf2 | Kruppel-like factor 2 (lung) | 3.671E−10 | 1.285134665 | 1.106060488 |
| Capn3 | calpain 3 | 0.0108324 | 1.269066665 | 1.041143567 |
| P2rx7 | purinergic receptor P2X, ligand-gated ion channel, 7 | 2.507E−09 | 1.254283105 | 1.062555789 |
| Trat1 | T cell receptor associated transmembrane adaptor 1 | 2.002E−08 | 1.247496664 | 1.115014034 |
| Klf3 | Kruppel-like factor 3 (basic) | 5.206E−08 | 1.242062467 | 1.097946279 |
| Irf7 | interferon regulatory factor 7 | 0.00003947 | 1.237559009 | 0.966178546 |
| Sox4 | SRY-box containing gene 4 | 0.00026928 | 1.218840832 | 1.069164455 |
| Socs3 | suppressor of cytokine signaling 3 | 0.000002704 | 1.197338018 | 1.043479784 |
| Ccr2 | chemokine (C-C motif) receptor 2 | 0.00088497 | 1.194479665 | 0.944542178 |
| Cd86 | CD86 antigen | 0.00095436 | 1.15990739 | 1.030515958 |
| Csf1 | colony stimulating factor 1 (macrophage) | 0.00018162 | 1.139043688 | 0.983451169 |
| Tnfrsf22 | tumor necrosis factor receptor superfamily, member 22 | 0.029579 | 1.135265234 | 0.999410833 |
| Sele | selectin, endothelial cell | 0.0611511 | 1.126037378 | 0.944445866 |
| Bcl2 | B-cell leukemia/lymphoma 2 | 0.000001345 | 1.200530854 | 1.036517252 |
| Ikzf2 | IKAROS family zinc finger 2 | 0.00539308 | 1.107958566 | 1.029981749 |
| Gpr83 | G protein-coupled receptor 83 | 7.928E−08 | 1.103769744 | 1.035679639 |
| Nt5e | 5' nucleotidase, ecto | 7.126E−11 | 1.115728599 | 1.042848886 |
| Pias1 | protein inhibitor of activated STAT 1 | 7.054E−07 | 1.229350664 | 1.051712288 |
| Pde2a | phosphodiesterase 2A, cGMP-stimulated | 7.143E−07 | 1.220384964 | 1.136825712 |
| Samhd1 | SAM domain and HD domain, 1 | 8.458E−08 | 1.272371694 | 1.088937279 |
| Rasgrp1 | RAS guanyl releasing protein 1 | 8.266E−10 | 1.132277662 | 1.052465539 |
| Sell | selectin, lymphocyte | 1.864E−08 | 1.119421504 | 1.040753113 |
| Ifngr1 | interferon gamma receptor 1 | 8.769E−10 | 1.139298486 | 1.054594449 |
| Il6st | interleukin 6 signal transducer | 3.242E−08 | 1.124112682 | 1.034980857 |
| Socs2 | suppressor of cytokine signaling 2 | 0.0013229 | 1.165949171 | 1.089333063 |
| Klrc1 | killer cell lectin-like receptor subfamily C, member 1 | 0.0231404 | 0.839384892 | 0.958292103 |
| Il4 | interleukin 4 | 0.0456394 | 0.884948909 | 0.98797694 |
| Il5 | interleukin 5 | 0.0200249 | 0.866258511 | 0.967564087 |
| Il17a | interleukin 17A | 0.0892365 | 0.876784798 | 0.980557686 |
| Irf4 | interferon regulatory factor 4 | 0.00166111 | 0.865581808 | 0.914790588 |
| Irf8 | interferon regulatory factor 8 | 1.627E−07 | 0.815320769 | 0.902639353 |
| Casp3 | caspase 3 | 0.00101569 | 0.768470287 | 0.986386473 |
| Lag3 | lymphocyte-activation gene 3 | 0.00074161 | 0.81582849 | 0.989058591 |
| Pax3 | paired box gene 3 | 0.0100615 | 0.824486955 | 1.028467901 |
| Rorc | RAR-related orphan receptor gamma | 0.0478239 | 0.82459593 | 1.058781462 |
| Eomes | eomesodermin homolog (*Xenopus laevis*) | 0.00329137 | 0.825853154 | 0.958256158 |
| Il9 | interleukin 9 | 0.0597995 | 0.83668632 | 0.99566111 |
| Klf1 | Kruppel-like factor 1 (erythroid) | 0.00007452 | 0.845474592 | 1.076712711 |
| Il17re | interleukin 17 receptor E | 0.037592 | 0.886991987 | 1.012299813 |
| Bcl7c | B-cell CLL/lymphoma 7C | 0.000004747 | 0.894221815 | 1.066003659 |
| Alcam | activated leukocyte cell adhesion molecule | 0.0031076 | 0.793324239 | 0.957458743 |
| Nedd4 | neural precursor cell expressed, developmentally down-regulated 4 | 0.000002309 | 0.807636853 | 1.058385025 |
| Vegfc | vascular endothelial growth factor C | 0.00171024 | 0.769523371 | 1.052111027 |
| Spry2 | sprouty homolog 2 (*Drosophila*) | 0.00029642 | 0.760398934 | 0.91800687 |
| Rgs16 | regulator of G-protein signaling 16 | 0.00002906 | 0.77611906 | 0.915180984 |
| Serpine2 | serine (or cysteine) peptidase inhibitor, clade E, member 2 | 3.332E−09 | 0.69502868 | 0.83449972 |
| Bcat1 | branched chain aminotransferase 1, cytosolic | 0.000004398 | 0.737455065 | 0.96648127 |
| Pdgfb | platelet derived growth factor, B polypeptide | 0.00004784 | 0.656164641 | 0.857934741 |
| Il3 | interleukin 3 | 0.00004922 | 0.594682398 | 0.78279364 |

The invention claimed is:

1. A method of inhibiting a function or decreasing stability of a regulatory T cell (Treg) while maintaining immune homeostasis in a subject, comprising: exposing the Treg in vivo to an anti-neuropilin-1 (NRP-1) antibody or antigen-binding fragment thereof which inhibits a neuropilin-1 (Nrp1): semaphorin-4 axis, wherein the anti-NRP-1 antibody or antigen-binding fragment thereof inhibits interaction between i) a transmembrane semaphorin-4 polypeptide on a cell expressing the transmembrane semaphorin-4 and ii) a NRP-1 polypeptide on the Treg.

2. The method of claim 1, wherein the cell expressing the transmembrane semaphorin-4 is selected from the group consisting of a conventional T cell, a conventional dendritic cell, and a plasmacytoid dendritic cell.

3. The method of claim 1, comprising administering to a human subject suffering from a cancer a pharmaceutical composition comprising an effective amount of the anti-NRP-1 antibody.

4. The method of claim 3, wherein the administering decreases Treg stability in the human subject.

5. The method of claim 1, wherein the anti-NRP-1 antibody is capable of binding to an extracellular domain of the NRP-1 polypeptide.

6. The method of claim 1, wherein the anti-NRP-1 antibody does not affect an interaction between the NRP-1 polypeptide and a vascular endothelial growth factor (VEGF) polypeptide.

7. The method of claim 1, wherein the anti-NRP-1 antibody increases Akt phosphorylation in the Treg.

8. The method of claim 1, wherein the anti-NRP-1 antibody is a monoclonal antibody.

9. The method of claim 1, wherein the Treg is an activated Treg.

10. The method of claim 1, wherein expression of NRP-1 on Tregs is dispensable for the prevention of inflammatory and autoimmune disease that would normally develop in the absence of Tregs.

11. The method of claim 3, wherein the administering does not induce an inflammatory or autoimmune disease in the human subject.

12. The method of claim 3, wherein the administering inhibits suppression of anti-tumor immunity in the human subject.

13. The method of claim 1, wherein the subject is a human subject.

14. The method of claim 13, wherein the human subject is suffering from cancer.

15. The method of claim 1, wherein the antibody is a humanized antibody.

16. The method of claim 1, wherein the antibody or antigen-binding fragment thereof binds to a portion of NRP-1 that is contacted by semaphorin-4.

* * * * *

UNITED STATES PATENT AND TRADEMARK OFFICE
CERTIFICATE OF CORRECTION

PATENT NO. : 9,540,439 B2
APPLICATION NO. : 14/434129
DATED : January 10, 2017
INVENTOR(S) : Dario Vignali et al.

Page 1 of 1

It is certified that error appears in the above-identified patent and that said Letters Patent is hereby corrected as shown below:

In the Specification

Column 1, Line 20-27, after "STATEMENT AS TO FEDERALLY SPONSORED RESEARCH," delete "The United States Government has certain rights to this invention by virtue of funding reserved from Grant Nos. AI091977, AI039480 and AI098383 from the National Institutes of Health and NCI Comprehensive Cancer Center Support CORE grant CA21765." and insert -- This invention was made with government support under grants AI091977, AI039480, AI098383 and CA021765 awarded by the National Institutes of Health. The government has certain rights in the invention. --.

Signed and Sealed this
Twelfth Day of June, 2018

Andrei Iancu
*Director of the United States Patent and Trademark Office*